US011858910B2

(12) United States Patent
Jin et al.

(10) Patent No.: US 11,858,910 B2
(45) Date of Patent: Jan. 2, 2024

(54) PYRIDINYLMETHYLENEPIPERIDINE DERIVATIVES AND USES THEREOF

(71) Applicant: SUNSHINE LAKE PHARMA CO., LTD., Guangdong (CN)

(72) Inventors: Chuanfei Jin, Dongguan (CN); Wenhe Zhong, Dongguan (CN); Yaping Xue, Dongguan (CN)

(73) Assignee: SUNSHINE LAKE PHARMA CO., LTD., Guangdong (CN)

( * ) Notice: Subject to any disclaimer, the term of this patent is extended or adjusted under 35 U.S.C. 154(b) by 550 days.

(21) Appl. No.: 17/263,177

(22) PCT Filed: Aug. 22, 2019

(86) PCT No.: PCT/CN2019/101985
§ 371 (c)(1),
(2) Date: Jan. 26, 2021

(87) PCT Pub. No.: WO2020/038435
PCT Pub. Date: Feb. 27, 2020

(65) Prior Publication Data

US 2021/0188803 A1 Jun. 24, 2021

(30) Foreign Application Priority Data

Aug. 24, 2018 (CN) ......................... 201810969837.5

(51) Int. Cl.
*C07D 401/08* (2006.01)
*C07D 401/14* (2006.01)

(52) U.S. Cl.
CPC ......... *C07D 401/08* (2013.01); *C07D 401/14* (2013.01)

(58) Field of Classification Search
CPC ............................ C07D 401/08; C07D 401/14
See application file for complete search history.

(56) References Cited

U.S. PATENT DOCUMENTS

| | | | |
|---|---|---|---|
| 5,817,671 A | 10/1998 | Filla et al. | |
| 6,133,290 A | 10/2000 | Krushinski, Jr. et al. | |
| 6,777,428 B1 | 8/2004 | Krushinski, Jr. et al. | |
| 7,291,632 B2 | 11/2007 | Blanco-Pillado et al. | |
| 7,312,236 B2 | 12/2007 | Kohlman et al. | |
| 7,423,050 B2 | 9/2008 | Cohen et al. | |
| 7,608,629 B2 | 10/2009 | Blanco-Pillado et al. | |
| 8,044,052 B2 | 10/2011 | Fay et al. | |
| 8,101,614 B2 | 1/2012 | Zhang et al. | |
| 10,023,559 B2 | 7/2018 | Cecere et al. | |
| 10,344,017 B2 * | 7/2019 | Reuillon .............. | C07D 413/14 |

FOREIGN PATENT DOCUMENTS

WO 2013/027001 A1 2/2013

OTHER PUBLICATIONS

Deyi Zhang et al.,Discovery of selective N-[3-(1-methyl-piperidine-4-carbonyl)-phenyl]-benzamide-based 5-HT1F receptor agonists: Evolution from bicyclic to monocyclic cores, Bioorganic & Medicinal Chemistry Letters (2015), 25(19), 4337-4341.
Brian M. Mathes et al., Substituted furo[3,2-b]pyridines: novel bioisosteres of 5-HT1F receptor agonists, Bioorganic & Medicinal Chemistry Letters (2004), 14(1), 167-170.
Nov. 21, 2019 International Search Report issued in International Patent Application No. PCT/CN2019/101985.
Nov. 21, 2019 Written Opinion issued in International Patent Application No. PCT/CN2019/101985.

* cited by examiner

*Primary Examiner* — Samantha L Shterengarts
*Assistant Examiner* — Karen Cheng
(74) *Attorney, Agent, or Firm* — Oliff PLC

(57) ABSTRACT

A pyridinylmethylenepiperidine derivatives and uses thereof, specifically, the present invention relates to a novel pyridinylmethylenepiperidine compound and a pharmaceutical composition containing this compound, which may be used for activating 5-$HT_{1F}$ receptor. The present invention also relates to methods of preparing this compound and pharmaceutical composition, and their use in the manufacture of a medicament for treating a 5-$HT_{1F}$ receptor-related disease, especially migraine.

19 Claims, No Drawings

PYRIDINYLMETHYLENEPIPERIDINE DERIVATIVES AND USES THEREOF

CROSS-REFERENCE TO RELATED APPLICATIONS

This application claims priority to Chinese Patent Application Serial No 201810969837.5, filed on Aug. 24, 2018, which is hereby incorporated by reference in its entirety.

FIELD OF THE INVENTION

The invention pertains to the pharmaceutical field, specifically relates to novel pyridinylmethylenepiperidine derivatives and pharmaceutical compositions containing these compounds, and their usage methods and uses. In particular, the novel pyridinylmethylenepiperidine derivatives disclosed herein may be used for activating 5-$HT_{1F}$ receptor, and for preventing, treating or lessening a 5-$HT_{1F}$ receptor-related disease, especially migraine.

BACKGROUND OF THE INVENTION

Migraine is an episodic and usually unilateral pulsatile headache, often accompanied by nausea and vomiting. It is a common chronic neurovascular disease, occurring mostly in children and adolescence, reaching its peak in middle and young age. Female patients are more common. The proportion of male and female patients is about 1:2-3. The prevalence rate is 5%-10% in the population. The patients often have genetic background.

Although migraine is not a fatal disease, it can seriously affect the social life of the patients. In the United States, the socio-economic burden of migraine is 1 billion to 1.7 billion U.S. dollar. There are also a large number of patients in our country who suffered from migraine, and their work, study and life are affected. With the acceleration pace of life, the incidence of migraine is gradually increasing. A recent survey found that about 5.7% of men and 17.6% of women have migraine more than once a year on average. In addition, there are still many people having a genetic predisposition to migraine.

The pathogenesis of migraine is complicated and various, mainly including vascular origin theory, neurogenesis theory, trigeminal neurovascular theory, biochemical factors and genetic factors. At present, the main drugs used for treating migraine are triptans, 5-$HT_{1B/D}$ receptor agonists. However, triptans will cause contraction of blood vessels, so which are forbidden for patients with cardiovascular and cerebrovascular diseases. Furthermore, triptans have a poor therapeutic effect on migraine for 40% to 70% of the patients, recurrence will often take place in one third of the patients after they underwent initial effective chemotherapy. The curative effect of triptans decreased significantly on moderate to severe headache of patients. In order to overcome these adverse reactions caused by triptans drugs, calcitonin gene-related peptide (CGRP) receptor antagonists and selective 5-$HT_{1F}$ receptor agonists have emerged as the times require. However, CGRP receptor antagonists still have many limitations, such as olcagepant can only be administered intravenously but not orally, long term usage of telcagepant can cause elevated liver enzymes, and clinical development of BI-44370 was stopped due to which can interact with cytochrome P450. Therefore, there is an urgent need to develop novel drugs for acute phase treatment. It is a new promising way to develop selective 5-$HT_{1F}$ receptor agonists as anti-migraine drugs.

Since 1938, Graham and Wolff's researches (Arch. Neurol. Psychiatry, 39:737-63, 1938) have dominated the theories regarding the pathophysiology of migraine. They proposed that the cause of migraine was vasodilation of extracranial vessels. This view was supported by the following evidence that ergot alkaloids and sumatriptan, a hydrophilic 5-$HT_1$ agonist which does not cross the blood-brain barrier, induce contraction of cephalic vascular smooth muscle and are effective in the treatment of migraine (Humphrey, et al., Ann. NY Acad. Sci., 600: 587-600, 1990). Recent work by Moskowitz has shown, however, that the occurrence of migraine headaches is independent of changes in vessel diameter (Cephalalgia, 12: 5-7, 1992).

Moskowitz study group has proposed that currently unknown triggers for pain stimulate trigeminal ganglia that innervate vasculature within the cephalic tissue, giving rise to release of vasoactive neuropeptides from axons on the vasculature. These released neuropeptides then activate a series of events, a consequence of which is pain. This neurogenic inflammation is blocked by ergot alkaloids and sumatriptan, and its blocking mechanism involves 5-HT receptors and is closely related to the 5-$HT_{1D}$ subtype located on the trigeminovascular fibers (Neurology, 43(suppl. 3): S16-S20, 1993). Sumatriptan, in fact, has a high affinity for the 5-$HT_{1B}$ and 5-$HT_{1D}$ receptors, Ki=10.3 nM and 5.1 nM, respectively, which may be indicative of vasoconstrictive activity.

5-Hydroxytryptamine receptors, also known as serotonin receptors or 5-HT receptors, are a group of G protein-coupled receptors occurring in the central of the central nervous system and around peripheral nervous system. They can be divided into seven subfamilies: 5-$HT_1$, 5-$HT_2$, 5-$HT_3$, 5-$HT_4$, 5-$HT_5$, 5-$HT_6$ and 5-$HT_7$, which mediate different physiological activities, respectively. Wherein, 5-$HT_1$ receptor is the largest family of 5-HT receptors. There are five subtypes of 5-$HT_{1A}$, 5-$HT_{1B}$, 5-$HT_{1D}$, 5-$HT_{1E}$ and 5-$HT_{1F}$. Kao's group isolated human gene that express one subtype (called 5-$HT_{1F}$) of 5-HT receptors (Proc. Natl. Acad. Sci. USA, 90: 408-412, 1993). The pharmacological activity of the 5-$HT_{1F}$ receptor is obviously different from that of any serotonin receptor that has been disclosed. They found that in addition for 5-$HT_{1B}$ and 5-$HT_{1D}$ receptors, Sumatriptan also had an affinity for this subtype receptor, with Ki value of about 23 nM. This suggests that 5-$HT_{1F}$ receptor may play a role in migraine.

5-$HT_{1F}$ receptors are mainly expressed in the mesentery, uterus and brain, and also in every part of trigeminal nerve vascular system such as the cerebral vessels, trigeminal ganglion and trigeminal caudal nucleus, as well as cerebellum, hippocampus and neocortex. As other 5-HT receptors, 5-$HT_{1F}$ receptor is expressed not only in neurons, but also in neuroglia cells. The activation of presynaptic 5-$HT_{1F}$ receptor can inhibit the release of calcitonin gene-related peptide (CGRP) and block the signal transduction of neurons in the caudal nucleus of trigeminal nerve, thus producing anti-migraine effect. This selective 5-$HT_{1F}$ receptor activation greatly reduces the side effects of vasoconstriction induced by triptans.

Various 5-$HT_{1F}$ receptor agonists with relative selectivity to 5-$HT_{1F}$ subtype receptor were subsequently developed, and the agonist with this selectivity usually reduces vasoconstrictive activity, which is typical of other compounds used as potential drugs for the treatment of migraine and related diseases. The following patent applications disclosed some compounds as 5-$HT_{1F}$ receptor agonists:

the patent application WO 2003084949 A1 disclosed pyridinoylpiperidines as 5-$HT_{1F}$ receptor agonists, their medicinal acid addition salts and their uses, which can be used to activate 5-$HT_{1F}$ receptors, inhibit neuronal proteins extravasation, and prevent or treat migraine in mammals;

the patent application WO 2000047559 A2 disclosed phenylacyl piperidines as 5-$HT_{1F}$ receptor agonists, their medicinal acid addition salts and their uses, which can be used to activate 5-$HT_{1F}$ receptors, inhibit neuronal proteins extravasation, and prevent or treat migraine in mammals;

the patent application WO 2005035499 A1 disclosed substituted 2-carbonylamino-6-piperidinaminopyridines and substituted 1-carbonylamino-3-piperidinaminobenzenes as 5-$HT_{1F}$ receptor agonists, their medicinal acid addition salts and their uses, which can be used to activate 5-$HT_{1F}$ receptors, inhibit neuronal proteins extravasation, and prevent or treat migraine in mammals;

the patent application WO 2004094380 A1 disclosed (piperidinyloxy)phenyl, (piperidinyloxy)pyridinyl, (piperidinylthio)phenyl and (piperidinylthio)pyridinyl compounds as 5-$HT_{1F}$ receptor agonists, their medicinal acid addition salts and their uses, which can be used to activate 5-$HT_{1F}$ receptors, inhibit neuronal proteins extravasation, and prevent or treat migraine in mammals;

the patent application WO 2005061439 A1 disclosed substituted (4-aminocyclohexen-1-yl)phenyl and (4-aminocyclohexen-1-yl)pyridinyl compounds as 5-$HT_{1F}$ receptor agonists, their medicinal acid addition salts and their uses, which can be used to activate 5-$HT_{1F}$ receptors, inhibit neuronal proteins extravasation, and prevent or treat migraine in mammals.

After continuous efforts, the inventors have obtained an unexpected novel class of selective 5-$HT_{1F}$ agonists with different properties of chemistry and receptor binding, which can inhibit peptide extravasation and avoid obvious vasoconstrictive activity. Therefore, they can be used to treat migraine and other 5-$HT_{1F}$ receptor-related diseases. Moreover, the compound of the invention has good solubility, and therefore has high adaptability in the preferred formulation, such as sublingual, buccal and/or intranasal administration.

SUMMARY OF THE INVENTION

The present invention provides a novel pyridinylmethylenepiperidine derivative as a 5-$HT_{1F}$ receptor agonist, which can be used to activate 5-$HT_{1F}$ receptor and inhibit neuronal protein extravasation. Therefore, it can be used to treat diseases mediated by 5-$HT_{1F}$ receptor, especially migraine. Through experiments, it was found that the pyridinylmethylenepiperidine derivative has stable properties, good safety, favorable pharmacodynamic characteristics and good pharmacokinetic properties, such as good brain/plasma ratio, good bioavailability or good metabolic stability, and so on. Therefore, it has a good clinical application prospect.

The invention also provides a method for preparing the compound and a pharmaceutical composition containing the compound, and uses of the compound and the pharmaceutical composition in the manufacture of a medicament.

In one aspect, provided herein is a compound having Formula (I) or a stereoisomer, a tautomer, an N-oxide, a hydrate, a solvate, a metabolite, a pharmaceutically acceptable salt or a prodrug thereof, (I)

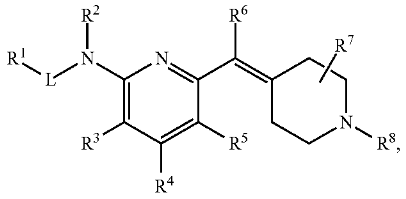

wherein

L is —C(=O)—, —C(=S)— or —S(=O)$_2$—;

$R^1$ is $C_1$-$C_6$ alkyl, $C_3$-$C_8$ cycloalkyl, 3-8 membered heterocyclyl, $C_6$-$C_{10}$ aryl or 5-10 membered heteroaryl, wherein $R^1$ is optionally substituted with 1, 2, 3, 4 or 5 substituents independently selected from $R^{1a}$, $R^{1b}$, $R^{1c}$, $R^{1d}$ and $R^{1e}$;

each $R^{1a}$, $R^{1b}$, $R^{1c}$, $R^{1d}$ and $R^{1e}$ is independently H, F, Cl, Br, I, —CN, —$NO_2$, —$NH_2$, —OH, —SH, —COOH, —C(=O)$NH_2$, —C(=O)$NHCH_3$, —C(=O)N$(CH_3)_2$, —C(=O)—($C_1$-$C_6$ alkyl), —C(=O)—($C_1$-$C_6$ alkoxy), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl or 5-10 membered heteroaryl;

$R^2$ is H, F, Cl, Br, I, —CN, —$NO_2$, —$NH_2$, —OH, —COOH, —C(=O)$NH_2$, $C_1$-$C_6$ alkyl, $C_1$-$C_6$ haloalkyl, $C_1$-$C_6$ alkoxy, $C_1$-$C_6$ haloalkoxy or hydroxy-substituted $C_1$-$C_6$ alkyl;

each of $R^3$, $R^4$ and $R^5$ is independently H, F, Cl, Br, I, —CN, —$NO_2$, —$NH_2$, —OH, —COOH, —C(=O)$NH_2$, $C_1$-$C_6$ alkyl, $C_1$-$C_6$ haloalkyl, $C_1$-$C_6$ alkoxy, $C_1$-$C_6$ haloalkoxy or hydroxy-substituted $C_1$-$C_6$ alkyl;

$R^6$ is H, F, Cl, Br or I;

$R^7$ is H, F, Cl, Br, I, —CN, —$NO_2$, —$NH_2$, —OH, —COOH, —C(=O)$NH_2$, $C_1$-$C_6$ alkyl, $C_1$-$C_6$ haloalkyl, $C_1$-$C_6$ alkoxy, $C_1$-$C_6$ haloalkoxy or hydroxy-substituted $C_1$-$C_6$ alkyl; and $R^8$ is H, F, Cl, Br, I, —CN, —$NO_2$, —$NH_2$, —OH, —SH, —COOH, —C(=O)$NH_2$, —C(=O)$NHCH_3$, —C(=O)N$(CH_3)_2$, —C(=O)—($C_1$-$C_6$ alkyl), —C(=O)—($C_1$-$C_6$ alkoxy), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl or 5-10 membered heteroaryl.

In some embodiments, $R^1$ is $C_1$-$C_4$ alkyl, $C_3$-$C_6$ cycloalkyl, 3-6 membered heterocyclyl, $C_6$-$C_{10}$ aryl or 5-10 membered heteroaryl, wherein $R^1$ is optionally substituted with 1, 2, 3, 4 or 5 substituents independently selected from $R^{1a}$, $R^{1b}$, $R^{1c}$, $R^{1d}$ and $R^{1e}$;

each $R^{1a}$, $R^{1b}$, $R^{1c}$, $R^{1d}$ and $R^{1e}$ is independently H, F, Cl, Br, I, —CN, —$NO_2$, —$NH_2$, —OH, —SH, —COOH, —C(=O)$NH_2$, —C(=O)$NHCH_3$, —C(=O)N$(CH_3)_2$, —C(=O)—($C_1$-$C_4$ alkyl), —C(=O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl.

In other embodiments, wherein $R^1$ is phenyl, indenyl, naphthyl, pyrrolyl, pyrazolyl, imidazolyl, triazolyl, tetrazolyl, furyl, thienyl, thiazolyl, oxazolyl, pyridyl, pyrimidinyl, pyrazinyl, pyridazinyl, benzimidazolyl, indolyl or quinolyl, wherein $R^1$ is optionally substituted with 1, 2, 3, 4 or 5 substituents independently selected from $R^{1a}$, $R^{1b}$, $R^{1c}$, $R^{1d}$ and $R^{1e}$;

each $R^{1a}$, $R^{1b}$, $R^{1c}$, $R^{1d}$ and $R^{1e}$ is independently H, F, Cl, Br, I, —CN, —$NO_2$, —$NH_2$, —OH, —SH, —COOH, —C(=O)$NH_2$, —C(=O)$NHCH_3$, —C(=O)$N(CH_3)_2$, —C(=O)—$CH_3$, —C(=O)—$OCH_3$, methyl, ethyl, n-propyl, i-propyl, allyl, propenyl, propargyl, propinyl, —$CHF_2$, —$CF_3$, —$CHFCH_2F$, —$CF_2CHF_2$, —$CH_2CF_3$, —$CH_2CF_2CHF_2$, methoxy, ethoxy, n-propoxy, i-propoxy, —$OCHF_2$, —$OCF_3$, —$OCHFCH_2F$, —$OCF_2CHF_2$, —$OCH_2CF_3$, —$OCH_2CF_2CHF_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl.

In some embodiments, $R^2$ is H, F, Cl, Br, I, —CN, —$NO_2$, —$NH_2$, —OH, —COOH, —C(=O)$NH_2$, $C_1$-$C_4$ alkyl, $C_1$-$C_4$ haloalkyl, $C_1$-$C_4$ alkoxy, $C_1$-$C_4$ haloalkoxy or hydroxy-substituted $C_1$-$C_4$ alkyl;

each of $R^3$, $R^4$ and $R^5$ is independently H, F, Cl, Br, I, —CN, —$NO_2$, —$NH_2$, —OH, —COOH, —C(=O)$NH_2$, $C_1$-$C_4$ alkyl, $C_1$-$C_4$ haloalkyl, $C_1$-$C_4$ alkoxy, $C_1$-$C_4$ haloalkoxy or hydroxy-substituted $C_1$-$C_4$ alkyl;

$R^7$ is H, F, Cl, Br, I, —CN, —$NO_2$, —$NH_2$, —OH, —COOH, —C(=O)$NH_2$, $C_1$-$C_4$ alkyl, $C_1$-$C_4$ haloalkyl, $C_1$-$C_4$ alkoxy, $C_1$-$C_4$ haloalkoxy or hydroxy-substituted $C_1$-$C_4$ alkyl.

In other embodiments, $R^2$ is H, F, Cl, Br, I, —CN, —$NO_2$, —$NH_2$, —OH, —COOH, —C(=O)$NH_2$, methyl, ethyl, n-propyl, i-propyl, —$CF_3$, —$CH_2CF_3$, methoxy, ethoxy, n-propoxy or i-propoxy;

each of $R^3$, $R^4$ and $R^5$ is independently H, F, Cl, Br, I, —CN, —$NO_2$, —$NH_2$, —OH, —COOH, —C(=O)$NH_2$, methyl, ethyl, n-propyl, i-propyl, —$CF_3$, —$CH_2CF_3$, methoxy, ethoxy, n-propoxy or i-propoxy;

$R^7$ is H, F, Cl, Br, I, —CN, —$NO_2$, —$NH_2$, —OH, —COOH, —C(=O)$NH_2$, methyl, ethyl, n-propyl, i-propyl, —$CF_3$, —$CH_2CF_3$, methoxy, ethoxy, n-propoxy or i-propoxy.

In some embodiments, $R^8$ is H, F, Cl, Br, I, —CN, —$NO_2$, —$NH_2$, —OH, —SH, —COOH, —C(=O)$NH_2$, —C(=O)$NHCH_3$, —C(=O)$N(CH_3)_2$, —C(=O)—($C_1$-$C_4$ alkyl), —C(=O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl.

In other embodiments, wherein $R^8$ is H, F, Cl, Br, I, —CN, —$NO_2$, —$NH_2$, —OH, —SH, —COOH, —C(=O)$NH_2$, —C(=O)$NHCH_3$, —C(=O)$N(CH_3)_2$, —C(=O)—$CH_3$, —C(=O)—$OCH_3$, methyl, ethyl, n-propyl, i-propyl, allyl, propenyl, propargyl, propinyl, —$CHF_2$, —$CF_3$, —$CHFCH_2F$, —$CF_2CHF_2$, —$CH_2CHF_2$, —$CH_2CF_3$, —$CH_2CF_2CHF_2$, methoxy, ethoxy, n-propoxy, i-propoxy, —$OCHF_2$, —$OCF_3$, —$OCHFCH_2F$, —$OCF_2CHF_2$, —$OCH_2CF_3$, —$OCH_2CF_2CHF_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl.

In some embodiments, provided herein is a compound having Formula (II) or a stereoisomer, a tautomer, an N-oxide, a hydrate, a solvate, a metabolite, a pharmaceutically acceptable salt or a prodrug thereof, (II)

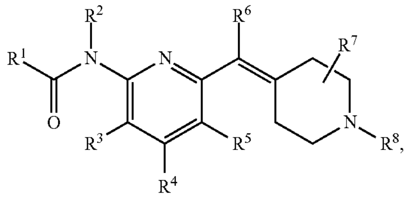

wherein each $R^1$, $R^2$, $R^3$, $R^4$, $R^5$, $R^6$, $R^7$ and $R^8$ is as defined herein.

In other embodiments, provided herein is a compound having Formula (III) or a stereoisomer, a tautomer, an N-oxide, a hydrate, a solvate, a metabolite, a pharmaceutically acceptable salt or a prodrug thereof, (III)

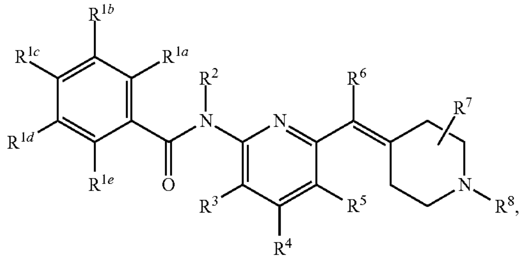

wherein each $R^{1a}$, $R^{1b}$, $R^{1c}$, $R^{1d}$, $R^{1e}$, $R^2$, $R^3$, $R^4$, $R^5$, $R^6$, $R^7$ and $R^8$ is as defined herein.

In still other embodiments, provided herein is a compound having Formula (IVa), Formula (IVb) or Formula (IVc), or a stereoisomer, a tautomer, an N-oxide, a hydrate, a solvate, a metabolite, a pharmaceutically acceptable salt or a prodrug thereof, (IVa)

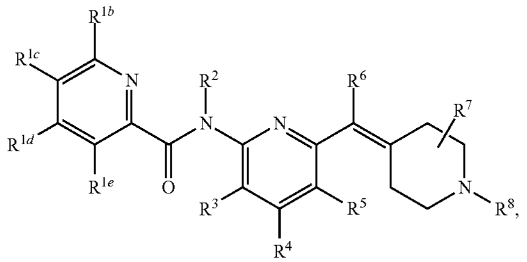

(IVb)

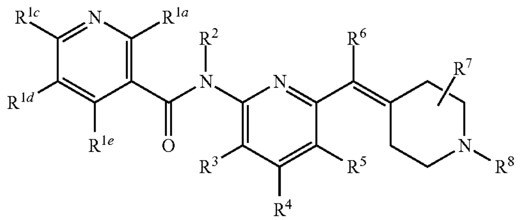

-continued (IVc)

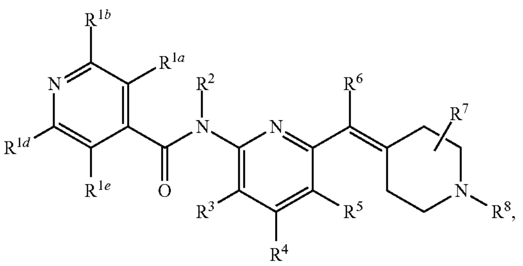

wherein each $R^{1a}$, $R^{1b}$, $R^{1c}$, $R^{1d}$, $R^{1e}$, $R^2$, $R^3$, $R^4$, $R^5$, $R^6$, $R^7$ and $R^8$ is as defined herein.

In yet other embodiments, provided herein is a compound having Formula (V) or a stereoisomer, a tautomer, an N-oxide, a hydrate, a solvate, a metabolite, a pharmaceutically acceptable salt or a prodrug thereof, (V)

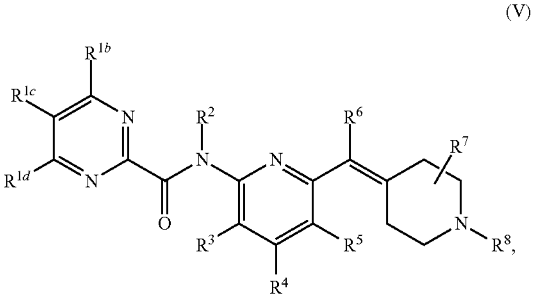

wherein each $R^{1b}$, $R^{1c}$, $R^{1d}$, $R^2$, $R^3$, $R^4$, $R^5$, $R^6$, $R^7$ and $R^8$ is as defined herein.

In other aspect, provided herein is a pharmaceutical composition comprising the compound of Formula (I), (II), (III), (IVa), (IVb), (IVc) or (V).

In some embodiments, the pharmaceutical composition disclosed herein further comprises a pharmaceutically acceptable excipient, a carrier, an adjuvant or a combination thereof.

In other aspect, the present invention relates to use of the compound represented by formula (I), (II), (III), (IVa), (IVb), (IVc) or (V) or the pharmaceutical composition in the manufacture of a medicament for preventing, treating or lessening a 5-$HT_{1F}$ receptor-related disease in a subject.

In some embodiments, wherein the 5-$HT_{1F}$ receptor-related disease is migraine, general pain, trigeminal neuralgia, dental pain or temporomandibular joint dysfunction pain, autism, obsession, phobia, depression, social phobia, anxiety, general anxiety disorder, disorders of sleep, post-traumatic syndrome, chronic fatigue syndrome, premenstrual syndrome or late luteal phase syndrome, borderline personality disorder, disruptive behavior disorders, impulse control disorders, attention deficit hyperactivity disorder, alcoholism, tobacco abuse, mutism, trichotillomania, bulimia, anorexia nervosa, premature ejaculation, erectile dysfunction, memory loss or dementia.

In yet other aspect, the present invention relates to use of the compound represented by formula (I), (II), (III), (IVa), (IVb), (IVc) or (V) or the pharmaceutical composition in the manufacture of a medicament for activating 5-$HT_{1F}$ receptor in a subject.

In other aspect, the present invention relates to the compound represented by formula (I), (II), (III), (IVa), (IVb), (IVc) or (V) or the pharmaceutical composition for use in preventing, treating or lessening a 5-$HT_{1F}$ receptor-related disease in a subject.

In some embodiments, wherein the 5-$HT_{1F}$ receptor-related disease is migraine, general pain, trigeminal neuralgia, dental pain or temporomandibular joint dysfunction pain, autism, obsession, phobia, depression, social phobia, anxiety, general anxiety disorder, disorders of sleep, post-traumatic syndrome, chronic fatigue syndrome, premenstrual syndrome or late luteal phase syndrome, borderline personality disorder, disruptive behavior disorders, impulse control disorders, attention deficit hyperactivity disorder, alcoholism, tobacco abuse, mutism, trichotillomania, bulimia, anorexia nervosa, premature ejaculation, erectile dysfunction, memory loss or dementia.

In yet other aspect, the present invention relates to the compound represented by formula (I), (II), (III), (IVa), (IVb), (IVc) or (V) or the pharmaceutical composition for use in activating 5-$HT_{1F}$ receptor in a subject.

In other aspect, the present invention relates to a method for preventing, treating or lessening a 5-$HT_{1F}$ receptor-related disease in a subject, comprising administering a therapeutically effective amount of the compound represented by formula (I), (II), (III), (IVa), (IVb), (IVc) or (V) or the pharmaceutical composition to the subject.

In some embodiments, wherein the 5-$HT_{1F}$ receptor-related disease is migraine, general pain, trigeminal neuralgia, dental pain or temporomandibular joint dysfunction pain, autism, obsession, phobia, depression, social phobia, anxiety, general anxiety disorder, disorders of sleep, post-traumatic syndrome, chronic fatigue syndrome, premenstrual syndrome or late luteal phase syndrome, borderline personality disorder, disruptive behavior disorders, impulse control disorders, attention deficit hyperactivity disorder, alcoholism, tobacco abuse, mutism, trichotillomania, bulimia, anorexia nervosa, premature ejaculation, erectile dysfunction, memory loss or dementia.

In yet other aspect, the present invention relates to a method for activating 5-$HT_{1F}$ receptor in a subject, comprising administering a therapeutically effective amount of the compound represented by formula (I), (II), (III), (IVa), (IVb), (IVc) or (V) or the pharmaceutical composition to the subject.

In other aspect, provided herein is a method of preparing, separating or purifying the compound of Formula (I), (II), (III), (IVa), (IVb), (IVc) or (V).

The biological test results showed that the compound disclosed herein can activate 5-$HT_{1F}$ receptor, inhibit neuronal protein extravasation, and can be used as a better 5-$HT_{1F}$ receptor agonist.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limited in nature. These aspects and other aspects and embodiments are described more fully below. All references of this specification are incorporated herein by reference in their entirety.

In the event that the incorporated literature differs from this application, this application controls.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry" by Michael B. Smith and Jerry March, John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e., at least one) of the grammatical objects of the article. By way of example, "a component" means one or more components, and thus, possibly, more than one component is contemplated and may be employed or used in an implementation of the described embodiments.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refer to two stereoisomers of a compound which are non-superimposable mirror images of one another.

"Racemate" or "racemic mixture" refers to an equimolar mixture of two enantiomers lacking optical activity.

"Diastereomer" refers to a stereoisomer with two or more centers of chirality and whose molecules are not mirror images of one another. Diastereomers have different physical properties, e.g. melting points, boling points, spectral properties or reactivities. A mixture of diastereomers may be separated under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A mixture of enantiomers with a ratio of 50:50 is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R, S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); *Principles of Asymmetric Synthesis* ($2^{nd}$ Ed. Robert E. Gawley, Jeffrey Aubé, Elsevier, Oxford, UK, 2012); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, IN 1972); Chiral Separation Techniques: A Practical Approach (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g., in solution), a chemical equilibrium of tautomers can be reached. For example, protontautomers (also known as prototropic tautomers) include interconversions via migration of a proton, such as keto-enol and imine-enamine isomerizations.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The terms "optionally substituted with . . . " and "unsubstituted or substituted with" can be used interchangeably, i.e., the structure is unsubstituted or substituted with one or more of the substituents described in the present invention, the substituents disclosed herein include, but are not limited to, D, F, Cl, Br, I, $N_3$, —CN, —$NO_2$, —$NH_2$, —OH, —SH, —COOH, —$CONH_2$, —C(═O)$NHCH_3$, —C(═O)N$(CH_3)_2$, —C(═O)-alkyl, —C(═O)-alkoxy, alkyl, alkenyl, alkynyl, haloalkyl, alkoxy, haloalkoxy, alkylthio, alkylamino, hydroxy-substituted alkyl, cycloalkyl, heterocyclyl, aryl, heteroaryl, and so on.

In general, the term "substituted" refers to the replacement of one or more hydrogen radicals in a given structure or radical with a specified substituent. Unless otherwise indicated, a substituent may substitute at any substitutable position of a radical. When more than one positions of a given structure can be substituted with one or more specified substituents, the substituents may be either the same or different at each position.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "comprise" is an open expression, it means comprising the contents disclosed herein, but don't exclude other contents.

At various places in the present specification, substituents of compounds disclosed herein are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "D" or "$^2$H" refers to a single deuterium atom.

The terms "halogen" and "halo" can be used interchangeably, which refer to Fluoro (F), Chloro (Cl), Bromo (Br), or Iodo (I).

The term "heteroatom" refers to oxygen, sulfur, nitrogen, phosphorus and silicon, including any oxidized form of nitrogen, sulfur, or phosphorus; primary, secondary, tertiary amines and quaternary ammonium salts forms; or a substitutable nitrogen of a heterocyclic ring, for example, N (as in 3,4-dihydro-2H-pyrrolyl), NH (as in pyrrolidinyl) or NR (as in N-substituted pyrrolidinyl, wherein R is the substituent described herein).

The term "alkyl" or "alkyl group" refers to a saturated linear or branched-chain monovalent hydrocarbon group of 1-20 carbon atoms, wherein the alkyl group is optionally substituted with one or more substituents described herein. In one embodiment, the alkyl group contains 1-6 carbon atoms. In other embodiment, the alkyl group contains 1-4 carbon atoms. In still other embodiment, the alkyl group contains 1-3 carbon atoms. Examples of the alkyl group include, but are not limited to, methyl (Me, —$CH_3$), ethyl (Et, —$CH_2CH_3$), n-propyl (n-Pr, —$CH_2CH_2CH_3$), i-propyl (i-Pr, —$CH(CH_3)_2$), n-butyl (n-Bu, —$CH_2CH_2CH_2CH_3$), i-butyl(i-Bu, —$CH_2CH(CH_3)_2$), s-butyl (s-Bu, —$CH(CH_3)CH_2CH_3$), t-butyl (t-Bu, —$C(CH_3)_3$), and the like.

The term "alkenyl" refers to linear or branched-chain monovalent hydrocarbon radical of 2 to 12 carbon atoms with at least one site of unsaturation, i.e., a carbon-carbon $sp^2$ double bond, wherein the alkenyl radical may be optionally substituted independently with one or more substituents described herein, and includes radicals having "cis" and "trans" orientations, or alternatively, "E" and "Z" orientations. In some embodiments, the alkenyl contains 2 to 8 carbon atoms. In other embodiments, the alkenyl contains 2 to 6 carbon atoms. In still other embodiments, the alkenyl contains 2 to 4 carbon atoms. Some non-limiting examples of the alkenyl group include ethenyl or vinyl (—CH═$CH_2$), allyl (—$CH_2$CH═$CH_2$), 1-propenyl (i.e., propenyl, —CH═CH—$CH_3$), and the like.

The term "alkynyl" refers to a linear or branched-chain monovalent hydrocarbon radical of 2 to 12 carbon atoms with at least one site of unsaturation, i.e., a carbon-carbon sp triple bond, wherein the alkynyl radical may be optionally substituted independently with one or more substituents described herein. In some embodiments, the alkynyl contains 2 to 8 carbon atoms. In other embodiments, the alkynyl contains 2 to 6 carbon atoms. In still other embodiments, the alkynyl contains 2 to 4 carbon atoms. Examples of such groups include, but are not limited to, ethynyl (—C≡CH), propargyl (—$CH_2$C≡CH), 1-propynyl (i.e., propynyl, —C≡C—$CH_3$), and the like.

The term "alkoxy" refers to an alkyl group, as previously defined, attached to the parent molecular moiety via an oxygen atom. Unless otherwise specified, the alkoxy group contains 1-12 carbon atoms. In one embodiment, the alkoxy group contains 1-6 carbon atoms. In other embodiment, the alkoxy group contains 1-4 carbon atoms. In still other embodiment, the alkoxy group contains 1-3 carbon atoms. The alkoxy group may be optionally substituted with one or more substituents disclosed herein.

Examples of the alkoxy group include, but are not limited to, methoxy (MeO, —$OCH_3$), ethoxy (EtO, —$OCH_2CH_3$), 1-propoxy (n-propyl-oxy, n-PrO, n-propoxy, $—OCH_2CH_2CH_3$), 2-propoxy (i-propyl-oxy, i-PrO, i-propoxy, $—OCH(CH_3)_2$), 1-butoxy (n-BuO, n-butoxy, $—OCH_2CH_2CH_2CH_3$), 2-methyl-1-propoxy (i-BuO, i-butoxy, $—OCH_2CH(CH_3)_2$), 2-butoxy (s-BuO, s-butoxy, $—OCH(CH_3)CH_2CH_3$), 2-methyl-2-propoxy (t-BuO, t-butoxy, $—OC(CH_3)_3$), and the like.

The term "alkylthio" refers to an alkyl group, as previously defined, attached to the parent molecular moiety via a sulfur atom. Unless otherwise specified, the alkylthio group contains 1-12 carbon atoms. In one embodiment, the alkylthio group contains 1-6 carbon atoms. In other embodiment, the alkylthio group contains 1-4 carbon atoms. In still other embodiment, the alkylthio group contains 1-3 carbon atoms. The alkylthio group may be optionally substituted with one or more substituents disclosed herein.

Examples of the alkylthio group include, but are not limited to, methylthio (MeS, $—SCH_3$), ethylthio (EtS, $—SCH_2CH_3$), 1-propylthio (n-PrS, n-propylthio, $—SCH_2CH_2CH_3$), 2-propylthio (i-PrS, i-propylthio, $—SCH(CH_3)_2$), 1-butylthio (n-BuS, n-butylthio, $—SCH_2CH_2CH_2CH_3$), 2-methyl-1-propylthio (i-BuS, i-butylthio, $—SCH_2CH(CH_3)_2$), 2-butylthio (s-BuS, s-butylthio, $—SCH(CH_3)CH_2CH_3$), 2-methyl-2-propylthio (t-BuS, t-butylthio, $—SC(CH_3)_3$), and the like.

The term "alkylamino" embraces "N-alkylamino" and "N,N-dialkylamino", that is an amino group is independently substituted with one or two alkyl radicals and wherein the alkyl group is as defined herein. Suitable alkylamino radical may be monoalkylamino or dialkylamino. Examples of the alkylamino radical include, but are not limited to, N-methylamino (methylamino), —N-ethylamino (ethylamino), —N,N-dimethylamino (dimethylamino), N,N-diethylamino (diethylamino), and the like. And wherein the alkylamino radical is optionally substituted with one or more substituents described herein.

The term "hydroxy-substituted alkyl" refers to an alkyl group substituted with one or more hydroxy groups, wherein the alkyl is as defined herein. Examples of such group include, but are not limited to, hydroxymethyl, 2-hydroxyethyl, 2-hydroxy-1-propyl, 3-hydroxy-1-propyl, 2,3-dihydroxypropyl, and the like.

The term "haloalkyl" refers to an alkyl group substituted with one or more halo groups, wherein the alkyl is as defined herein. Examples of such group include, but are not limited to, $—CHF_2$, $—CF_3$, $—CHFCH_2F$, $—CF_2CHF_2$, $—CH_2CHF_2$, $—CH_2CF_3$, $—CHFCH_3$, $—CH_2CH_2F$, $—CF_2CH_3$, $—CH_2CF_2CHF_2$, and the like. In some embodiments, $C_1$-$C_6$ haloalkyl include fluoro substituted $C_1$-$C_6$ alkyl; in the other embodiments, $C_1$-$C_4$ haloalkyl include fluoro substituted $C_1$-$C_4$ alkyl; in still other embodiments, $C_1$-$C_2$ haloalkyl include fluoro substituted $C_1$-$C_2$ alkyl.

The term "haloalkoxy" refers to an alkoxy group substituted with one or more halo groups, wherein the alkoxy is as defined herein. Examples of such group include, but are not limited to, $—OCHF_2$, $—OCF_3$, $—OCHFCH_2F$, $—OCF_2CHF_2$, $—OCH_2CHF_2$, $—OCH_2CF_3$, $—OCHFCH_3$, $—OCH_2CH_2F$, $—OCF_2CH_3$, $—OCH_2CF_2CHF_2$, and the like. In some embodiments, $C_1$-$C_6$ haloalkoxy include fluoro substituted $C_1$-$C_6$ alkoxy; in other embodiments, $C_1$-$C_4$ haloalkoxy include fluoro substituted $C_1$-$C_4$ alkoxy; in still other embodiments, $C_1$-$C_2$ haloalkoxy include fluoro substituted $C_1$-$C_2$ alkoxy.

The term "consisting of n atoms" or "n-membered", used interchangeably herein, where n is an integer typically describes the number of ring-forming atoms in a moiety where the number of ring-forming atoms is n. For example, "5-10 membered heteroaryl" refers to a heteroaryl consisting of 5, 6, 7, 8, 9 or 10 ring atoms. As another example, piperidinyl is a heterocyclyl consisting of 6 ring atoms or a 6 membered heterocyclyl, and pyridyl is a heteroaryl consisting of 6 ring atoms or a 6 membered heteroaryl.

The term "carbocyclyl", "carbocycle" or "carbocyclic ring" refers to a monovalent or multivalent, nonaromatic, saturated or partially unsaturated ring having 3 to 12 carbon atoms as a monocyclic, bicyclic or tricyclic ring system. A carbobicyclyl group includes a spiro carbobicyclyl group or a fused carbobicyclyl group. Suitable carbocyclyl groups include, but are not limited to, cycloalkyl, cycloalkenyl and cycloalkynyl. Further examples of the carbocyclyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. and wherein the carbocyclyl group is optionally substituted with one or more substituents described herein.

The term "cycloalkyl" refers to a monovalent or multivalent saturated ring having 3 to 12 carbon atoms as a monocyclic, bicyclic, or tricyclic ring system, wherein the bicyclic or tricyclic ring system may include fused ring, bridged ring and spiro ring. In some embodiments, the cycloalkyl group contains 3 to 10 carbon atoms. In other embodiments, the cycloalkyl group contains 3 to 8 carbon atoms. In still other embodiments, the cycloalkyl group contains 3 to 6 carbon atoms. Examples of cycloalkyl groups include, but are not limited to, cyclopropyl, cyclobutyl, cyclopentyl, cyclohexyl, and the like. The cycloalkyl radical is optionally substituted with one or more substituents described herein.

The term "heterocycle", "heterocyclyl", or "heterocyclic ring" as used interchangeably herein refers to a saturated or partially unsaturated and nonaromatic monocyclic, bicyclic or tricyclic ring system containing 3-12 ring atoms, wherein the bicyclic or tricyclic ring system may include a fused ring, bridged ring and spiro ring. Wherein one or more atoms on the ring each are independently replaced by heteroatom, the heteroatom is as defined herein. In some embodiments, the heterocyclyl group is a monocyclic heterocyclyl having 3-8 ring members (e.g., 2 to 6 carbon atoms and 1 to 3 heteroatoms selected from N, O, P and S, wherein the S or P is optionally substituted with one or more oxo to provide the group SO or $SO_2$, PO or $PO_2$); in other embodiments, the heterocyclyl group is a monocyclic heterocyclyl having 3-6 ring members (e.g., 2 to 5 carbon atoms and 1 to 3 heteroatoms selected from N, O, P and S, wherein the S or P is optionally substituted with one or more oxo to provide the group SO or $SO_2$, PO or $PO_2$); in still other embodiments, the heterocyclyl group is a bicyclic heterocyclyl having 7-12 ring members (e.g., 4 to 9 carbon atoms and 1 to 3 heteroatoms selected from N, O, P and S, wherein the S or P is optionally substituted with one or more oxo to provide the group SO or $SO_2$, PO or $PO_2$); and wherein the heterocyclyl group is optionally substituted with one or more substituents described herein.

The heterocyclyl may be a carbon atom radical or heteroatom radical. Of which a $—CH_2—$ group can be optionally replaced by a —C(═O)— group. Ring sulfur atoms may be optionally oxidized to form S-oxides, and ring nitrogen atoms may be optionally oxidized to form N-oxides. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo [2.2.1]hept-5-yl, and the like. Some non-limiting examples of heterocyclyl wherein —$CH_2$— group is replaced by —C(═O)— moiety include 2-oxopyrrolidinyl, oxo-1,3-thiazolidinyl, 2-piperidinonyl, 3,5-dioxopiperidinyl, pyrimidinedioneyl, and the like. Some non-limiting examples of oxidized ring sulfur atoms of the heterocyclyl group include sulfolanyl, 1,1-dioxo-thiomorpholinyl, and the like. The heterocyclyl group is optionally substituted with one or more substituents described herein.

The term "aryl" refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members. The aryl group is generally, but not necessarily bonded to the parent molecule through an aromatic ring of the aryl group. The term "aryl" and "aromatic ring" can be used interchangeably herein. Examples of the aryl group may include phenyl, indenyl, naphthyl, and anthryl. The aryl radical is optionally substituted with one or more substituents described herein.

The term "heteroaryl" refers to monocyclic, bicyclic and tricyclic ring systems having a total of five to twelve ring members, or five to ten ring members, or five to six ring members, wherein at least one ring in the system is aromatic, and in which at least one ring system contains one or more heteroatoms, and wherein each ring system contains a 5 to 7 members ring. The heteroaryl group is generally, but not necessarily bonded to the parent molecule through an aromatic ring of the heteroaryl group. The term "heteroaryl" may be used interchangeably with the term "heteroaryl ring", "aromatic heterocyclic" or the term "heteroaromatic compound". The heteroaryl group is optionally substituted with one or more substituents disclosed herein. In one embodiment, a 5-10 membered heteroaryl comprises 1, 2, 3 or 4 heteroatoms independently selected from O, S and N.

Some non-limiting examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzoimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a] pyrimidyl, imidazo[1,2-b]pyridazinyl, [1,2,4]triazolo[4,3-b] pyridazinyl, [1,2,4]triazolo[1,5-a]pyrimidinyl, or [1,2,4] triazolo[1,5-a]pyridyl, and so on.

As described herein, a ring system (such as formula f) forming by a bond drawn from a substituent $R^7$ to the center of piperidine ring represents that the substituent $R^7$ may be substituted at any substitutable position on the piperidine ring, such as formula $f^{1-4}$.

formula f

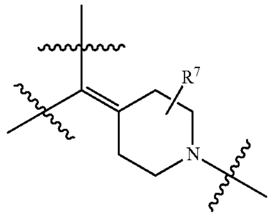

formula $f^1$

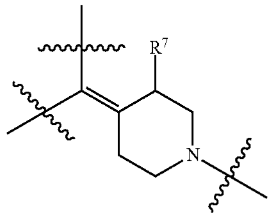

formula $f^2$

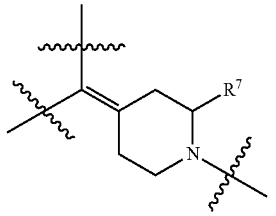

formula $f^3$

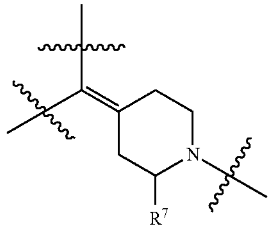

formula $f^4$

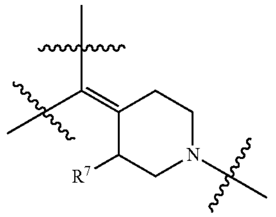

The sentence "$R^1$ is optionally substituted with 1, 2, 3, 4 or 5 substituents independently selected from $R^{1a}$, $R^{1b}$, $R^{1c}$, $R^{1d}$ and $R^{1e}$" means that $R^1$ may be unsubstituted, or $R^1$ may be substituted with 1, 2, 3, 4 or 5 substituents independently selected from $R^{1a}$, $R^{1b}$, $R^{1c}$, $R^{1d}$ and $R^{1e}$, wherein $R^{1a}$, $R^{1b}$, $R^{1c}$, $R^{1d}$ and $R^{1e}$ have the definition described herein, which may be the same group, also may be independently different group.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC, Boc), benzyloxycarbonyl (CBZ, Cbz) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include trialkylsilyl, acetyl, benzoyl, and benzyl. A "carboxy-protecting group" refers to a substituent of the carboxy group that blocks or protects the carboxy functionality. Common carboxy-protecting groups include $—CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)ethyl, nitroethyl and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

The term "prodrug" refers to a compound that is transformed in vivo into a compound of Formula (I), (II), (III), (IVa), (IVb), (IVc) or (V). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound.

A "metabolite" is a product produced through metabolism in the body of a specified compound or salt thereof. The metabolites of a compound may be identified using routine techniques known in the art and their activities may be determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphanic acid salt, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid, ethanolamine or a combination thereof. The term "hydrate" refers to the complex where the solvent molecule is water.

The term "hydrate" can be used when said solvent is water. In one embodiment, one solvent molecule is associated with one molecule of the compounds disclosed herein, such as a hydrate. In another embodiment, more than one solvent molecule may be associated with one molecule of the compounds disclosed herein, such as a dihydrate. In still another embodiment, less than one solvent molecule may be associated with one molecule of the compounds disclosed herein, such as a hemihydrate. Furthermore, all the hydrates of the invention retain the biological effectiveness of the non-hydrate form of the compounds disclosed herein.

The term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or exacerbation of the disease or disorder.

The term "preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

Unless otherwise stated, all suitable isotopic variations, stereoisomers, tautomers, solvates, metabolites, salts and pharmaceutically acceptable prodrugs of the compounds disclosed herein are within the scope of the invention.

All stereoisomers of the structure disclosed herein are considered within the scope of the invention whether the stereochemistry of the structure is indicated or not, and which are interpreted as disclosed compounds of the invention and included in the invention. When the stereochemistry of a structure is indicated by solid wedge or dash line, the stereoisomer of the structure is definite.

N-oxides of the compound disclosed herein are also included in the invention. N-oxides of the compound of the invention can be prepared by oxidizing corresponding nitrogen-containing alkaline substances with common oxidants (hydrogen peroxide) under a rising temperature in the presence of an acid, such as acetic acid, or by reacting with peracid in a suitable solvent, e.g., by reacting with peracetic acid in dichloromethane, ethyl acetate or methyl acetate, or by reacting with 3-chloroperoxybenzoic acid in chloroform or dichloromethane.

The compound of Formula (I), (II), (III), (IVa), (IVb), (IVc) or (V) can be exist in salt forms. In one embodiment, the salt is a pharmaceutically acceptable salt thereof. The phrase "pharmaceutically acceptable" refers to that the substance or composition must be chemically and/or toxicologically compatible with the other ingredients comprising a formulation, and/or the mammal being treated therewith. In other embodiments, the salt may not be a pharmaceutically acceptable salt, may be an intermediate used for preparing and/or purifying the compound of Formula (I), (II), (III), (IVa), (IVb), (IVc) or (V) and/or isolating an enantiomer from the compound of Formula (I), (II), (III), (IVa), (IVb), (IVc) or (V).

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "*Remington's Pharmaceutical Sciences*", 20th ed., Mack Publishing Company, Easton, Pa., (1985); and in "*Handbook of Pharmaceutical Salts: Properties, Selection, and Use*" by Stahl and Wermuth (Wiley-VCH, Weinheim, Germany, 2002).

Any formula given herein is also intended to represent isotopically unenriched forms as well as isotopically enriched forms of the compounds. Isotopically enriched compounds have the structure depicted by the general formula given herein, except that one or more atoms are replaced by atom(s) having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^{2}H$ (deuterium, D), $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$, $^{125}I$, respectively.

In other aspect, provided herein is an intermediate for preparing the compound of Formula (I), (II), (III), (IVa), (IVb), (IVc) or (V).

In other aspect, provided herein is a pharmaceutical composition comprising the compound disclosed herein. In some embodiments, the pharmaceutical composition disclosed herein further comprises at least one of pharmaceutically acceptable carrier, excipient, adjuvant, solvent or a combination thereof. In other embodiment, the pharmaceutical composition can be liquid, solid, semi-solid, gel or spray.

DESCRIPTION OF COMPOUNDS OF THE INVENTION

The pyridinylmethylenepiperidine derivatives, pharmaceutically acceptable salts, pharmaceutical formulations and compositions thereof disclosed herein can be used to activate $5\text{-HT}_{1F}$ receptors and inhibit neuronal protein extravasation, and have potential therapeutic use for $5\text{-HT}_{1F}$ receptor-related diseases, especially migraine. The present invention further describes the synthetic method of the compound. The compounds of the invention show good bioactivity.

In one aspect, provided herein is a compound having Formula (I) or a stereoisomer, a tautomer, an N-oxide, a hydrate, a solvate, a metabolite, a pharmaceutically acceptable salt or a prodrug thereof, (I)

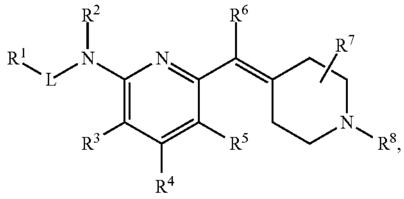

wherein each $R^1$, $R^2$, $R^3$, $R^4$, $R^5$, $R^6$, $R^7$, $R^8$ and L is as defined herein.

In some embodiments, L is —C(═O)—, —C(═S)— or —S(═O)$_2$—.

In some embodiments, $R^1$ is $C_1$-$C_6$ alkyl, $C_3$-$C_8$ cycloalkyl, 3-8 membered heterocyclyl, $C_6$-$C_{10}$ aryl or 5-10 membered heteroaryl, wherein $R^1$ is optionally substituted with 1, 2, 3, 4 or 5 substituents independently selected from $R^{1a}$, $R^{1b}$, $R^{1c}$, $R^{1d}$ and $R^{1e}$; wherein $R^{1a}$, $R^{1b}$, $R^{1c}$, $R^{1d}$ and $R^{1e}$ have the definition described herein.

In some embodiments, each $R^{1a}$, $R^{1b}$, $R^{1c}$, $R^{1d}$ and $R^{1e}$ is independently H, F, Cl, Br, I, —CN, —$NO_2$, —$NH_2$, —OH, —SH, —COOH, —C(═O)$NH_2$, —C(═O)$NHCH_3$, —C(═O)N$(CH_3)_2$, —C(═O)—($C_1$-$C_6$ alkyl), —C(═O)—($C_1$-$C_6$ alkoxy), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl or 5-10 membered heteroaryl.

In some embodiments, $R^2$ is H, F, Cl, Br, I, —CN, —$NO_2$, —$NH_2$, —OH, —COOH, —C(═O)$NH_2$, $C_1$-$C_6$ alkyl, $C_1$-$C_6$ haloalkyl, $C_1$-$C_6$ alkoxy, $C_1$-$C_6$ haloalkoxy or hydroxy-substituted $C_1$-$C_6$ alkyl.

In some embodiments, each of $R^3$, $R^4$ and $R^5$ is independently H, F, Cl, Br, I, —CN, —$NO_2$, —$NH_2$, —OH, —COOH, —C(═O)$NH_2$, $C_1$-$C_6$ alkyl, $C_1$-$C_6$ haloalkyl, $C_1$-$C_6$ alkoxy, $C_1$-$C_6$ haloalkoxy or hydroxy-substituted $C_1$-$C_6$ alkyl.

In some embodiments, $R^6$ is H, F, Cl, Br or I.

In some embodiments, $R^7$ is H, F, Cl, Br, I, —CN, —$NO_2$, —$NH_2$, —OH, —COOH, —C(═O)$NH_2$, $C_1$-$C_6$ alkyl, $C_1$-$C_6$ haloalkyl, $C_1$-$C_6$ alkoxy, $C_1$-$C_6$ haloalkoxy or hydroxy-substituted $C_1$-$C_6$ alkyl.

In some embodiments, $R^8$ is H, F, Cl, Br, I, —CN, —$NO_2$, —$NH_2$, —OH, —SH, —COOH, —C(═O)$NH_2$, —C(═O)$NHCH_3$, —C(═O)N$(CH_3)_2$, —C(═O)—($C_1$-$C_6$ alkyl), —C(═O)—($C_1$-$C_6$ alkoxy), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl or 5-10 membered heteroaryl.

In some embodiments, $R^1$ is $C_1$-$C_4$ alkyl, $C_3$-$C_6$ cycloalkyl, 3-6 membered heterocyclyl, $C_6$-$C_{10}$ aryl or 5-10 membered heteroaryl, wherein $R^1$ is optionally substituted with 1, 2, 3, 4 or 5 substituents independently selected from $R^{1a}$, $R^{1b}$, $R^{1c}$, $R^{1d}$ and $R^{1e}$; wherein $R^{1a}$, $R^{1b}$, $R^{1c}$, $R^{1d}$ and $R^{1e}$ have the definition described herein.

In other embodiments, wherein $R^1$ is phenyl, indenyl, naphthyl, pyrrolyl, pyrazolyl, imidazolyl, triazolyl, tetrazolyl, furyl, thienyl, thiazolyl, oxazolyl, pyridyl, pyrimidinyl, pyrazinyl, pyridazinyl, benzimidazolyl, indolyl or quinolyl, wherein $R^1$ is optionally substituted with 1, 2, 3, 4 or 5 substituents independently selected from $R^{1a}$, $R^{1b}$, $R^{1c}$, $R^{1d}$ and $R^{1e}$; wherein $R^{1a}$, $R^{1b}$, $R^{1c}$, $R^{1d}$ and $R^{1e}$ have the definition described herein.

In some embodiments, each $R^{1a}$, $R^{1b}$, $R^{1c}$, $R^{1d}$ and $R^{1e}$ is independently H, F, Cl, Br, I, —CN, —$NO_2$, —$NH_2$, —OH, —SH, —COOH, —C(═O)$NH_2$, —C(═O)$NHCH_3$, —C(═O)$N(CH_3)_2$, —C(═O)—($C_1$-$C_4$ alkyl), —C(═O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl.

In other embodiments, each $R^{1a}$, $R^{1b}$, $R^{1c}$, $R^{1d}$ and $R^{1e}$ is independently H, F, Cl, Br, I, —CN, —$NO_2$, —$NH_2$, —OH, —SH, —COOH, —C(═O)$NH_2$, —C(═O)$NHCH_3$, —C(═O)$N(CH_3)_2$, —C(═O)—$CH_3$, —C(═O)—$OCH_3$, methyl, ethyl, n-propyl, i-propyl, allyl, propenyl, propargyl, propinyl, —$CHF_2$, —$CF_3$, —$CHFCH_2F$, —$CF_2CHF_2$, —$CH_2CF_3$, —$CH_2CF_2CHF_2$, methoxy, ethoxy, n-propoxy, i-propoxy, —$OCHF_2$, —$OCF_3$, —$OCHFCH_2F$, —$OCF_2CHF_2$, —$OCH_2CF_3$, —$OCH_2CF_2CHF_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl.

In some embodiments, $R^2$ is H, F, Cl, Br, I, —CN, —$NO_2$, —$NH_2$, —OH, —COOH, —C(═O)$NH_2$, $C_1$-$C_4$ alkyl, $C_1$-$C_4$ haloalkyl, $C_1$-$C_4$ alkoxy, $C_1$-$C_4$ haloalkoxy or hydroxy-substituted $C_1$-$C_4$ alkyl.

In other embodiments, $R^2$ is H, F, Cl, Br, I, —CN, —$NO_2$, —$NH_2$, —OH, —COOH, —C(═O)$NH_2$, methyl, ethyl, n-propyl, i-propyl, —$CF_3$, —$CH_2CF_3$, methoxy, ethoxy, n-propoxy or i-propoxy.

In some embodiments, each of $R^3$, $R^4$ and $R^5$ is independently H, F, Cl, Br, I, —CN, —$NO_2$, —$NH_2$, —OH, —COOH, —C(═O)$NH_2$, $C_1$-$C_4$ alkyl, $C_1$-$C_4$ haloalkyl, $C_1$-$C_4$ alkoxy, $C_1$-$C_4$ haloalkoxy or hydroxy-substituted $C_1$-$C_4$ alkyl.

In other embodiments, each of $R^3$, $R^4$ and $R^5$ is independently H, F, Cl, Br, I, —CN, —$NO_2$, —$NH_2$, —OH, —COOH, —C(═O)$NH_2$, methyl, ethyl, n-propyl, i-propyl, —$CF_3$, —$CH_2CF_3$, methoxy, ethoxy, n-propoxy or i-propoxy.

In some embodiments, $R^7$ is H, F, Cl, Br, I, —CN, —$NO_2$, —$NH_2$, —OH, —COOH, —C(═O)$NH_2$, $C_1$-$C_4$ alkyl, $C_1$-$C_4$ haloalkyl, $C_1$-$C_4$ alkoxy, $C_1$-$C_4$ haloalkoxy or hydroxy-substituted $C_1$-$C_4$ alkyl.

In other embodiments, $R^7$ is H, F, Cl, Br, I, —CN, —$NO_2$, —$NH_2$, —OH, —COOH, —C(═O)$NH_2$, methyl, ethyl, n-propyl, i-propyl, —$CF_3$, —$CH_2CF_3$, methoxy, ethoxy, n-propoxy or i-propoxy.

In some embodiments, $R^8$ is H, F, Cl, Br, I, —CN, —$NO_2$, —$NH_2$, —OH, —SH, —COOH, —C(═O)$NH_2$, —C(═O)$NHCH_3$, —C(═O)$N(CH_3)_2$, —C(═O)—($C_1$-$C_4$ alkyl), —C(═O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl.

In other embodiments, wherein $R^8$ is independently H, F, Cl, Br, I, —CN, —$NO_2$, —$NH_2$, —OH, —SH, —COOH, —C(═O)$NH_2$, —C(═O)$NHCH_3$, —C(═O)$N(CH_3)_2$, —C(═O)—$CH_3$, —C(═O)—$OCH_3$, methyl, ethyl, n-propyl, i-propyl, allyl, propenyl, propargyl, propinyl, —$CHF_2$, —$CF_3$, —$CHFCH_2F$, —$CF_2CHF_2$, —$CH_2CHF_2$, —$CH_2CF_3$, —$CH_2CF_2CHF_2$, methoxy, ethoxy, n-propoxy, i-propoxy, —$OCHF_2$, —$OCF_3$, —$OCHFCH_2F$, —$OCF_2CHF_2$, —$OCH_2CF_3$, —$OCH_2CF_2CHF_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl.

In some embodiments, provided herein is a compound having Formula (II) or a stereoisomer, a tautomer, an N-oxide, a hydrate, a solvate, a metabolite, a pharmaceutically acceptable salt or a prodrug thereof, (II)

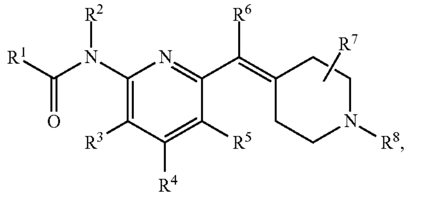

wherein each $R^1$, $R^2$, $R^3$, $R^4$, $R^5$, $R^6$, $R^7$ and $R^8$ is as defined herein.

In other embodiments, provided herein is a compound having Formula (III) or a stereoisomer, a tautomer, an N-oxide, a hydrate, a solvate, a metabolite, a pharmaceutically acceptable salt or a prodrug thereof, (III)

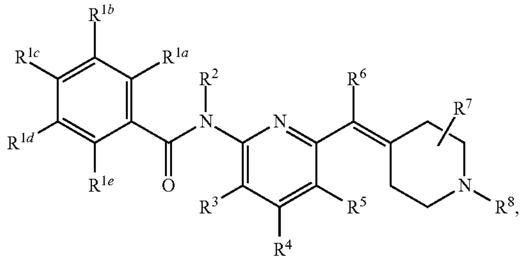

wherein each $R^{1a}$, $R^{1b}$, $R^{1c}$, $R^{1d}$, $R^{1e}$, $R^2$, $R^3$, $R^4$, $R^5$, $R^6$, $R^7$ and $R^8$ is as defined herein.

In yet other embodiments, provided herein is a compound having Formula (IVa) or a stereoisomer, a tautomer, an N-oxide, a hydrate, a solvate, a metabolite, a pharmaceutically acceptable salt or a prodrug thereof, (IVa)

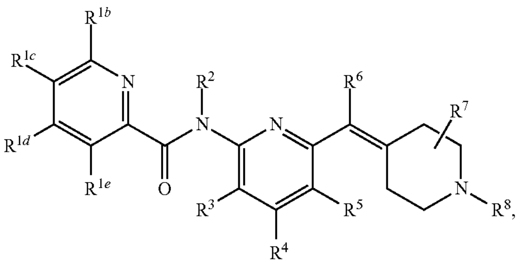

wherein each $R^{1b}$, $R^{1c}$, $R^{1d}$, $R^{1e}$, $R^2$, $R^3$, $R^4$, $R^5$, $R^6$, $R^7$ and $R^8$ is as defined herein.

In yet other embodiments, provided herein is a compound having Formula (IVb) or a stereoisomer, a tautomer, an N-oxide, a hydrate, a solvate, a metabolite, a pharmaceutically acceptable salt or a prodrug thereof, (IVb)

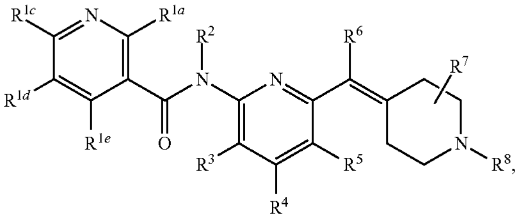

wherein each $R^{1a}$, $R^{1b}$, $R^{1c}$, $R^{1d}$, $R^{1e}$, $R^2$, $R^3$, $R^4$, $R^5$, $R^6$, $R^7$ and $R^8$ is as defined herein.

In yet other embodiments, provided herein is a compound having Formula (IVc) or a stereoisomer, a tautomer, an N-oxide, a hydrate, a solvate, a metabolite, a pharmaceutically acceptable salt or a prodrug thereof, (IVc)

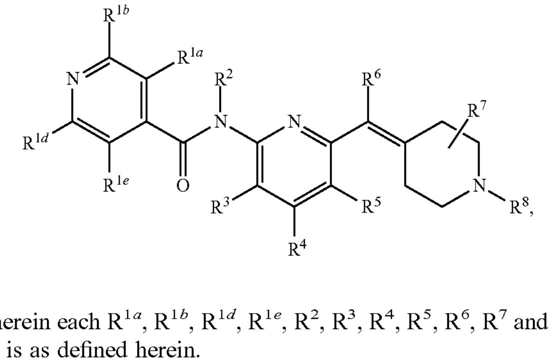

wherein each $R^{1a}$, $R^{1b}$, $R^{1d}$, $R^{1e}$, $R^2$, $R^3$, $R^4$, $R^5$, $R^6$, $R^7$ and $R^8$ is as defined herein.

In yet other embodiments, provided herein is a compound having Formula (V) or a stereoisomer, a tautomer, an N-oxide, a hydrate, a solvate, a metabolite, a pharmaceutically acceptable salt or a prodrug thereof, (V)

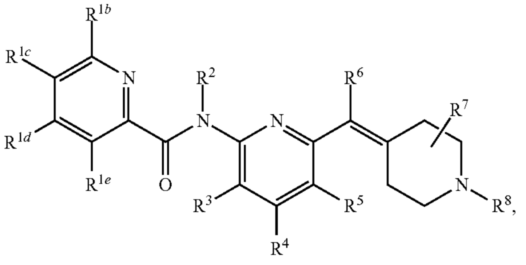

wherein each $R^{1b}$, $R^{1c}$, $R^{1d}$, $R^2$, $R^3$, $R^4$, $R^5$, $R^6$, $R^7$ and $R^8$ is as defined herein.

In some embodiments, the compound disclosed herein has one of the following structures or a stereoisomer, a tautomer, an N-oxide, a hydrate, a solvate, a metabolite, a pharmaceutically acceptable salt or a prodrug thereof, but is in no way limited to:

(1)

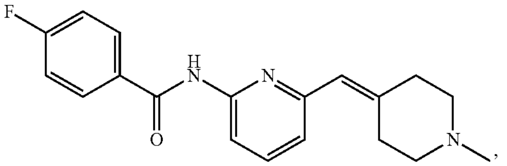

(2)

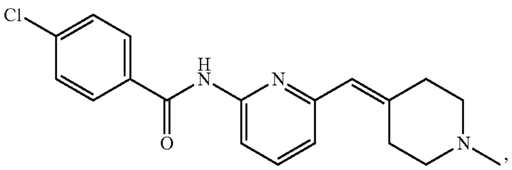

(3)

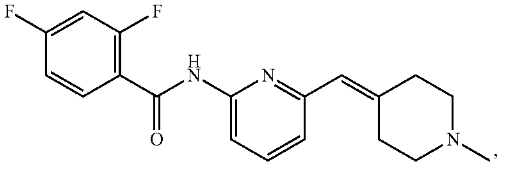

(4)

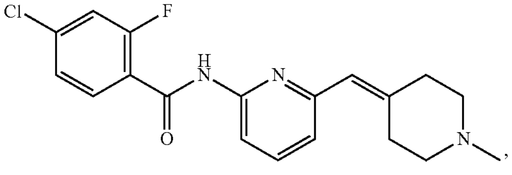

(5)

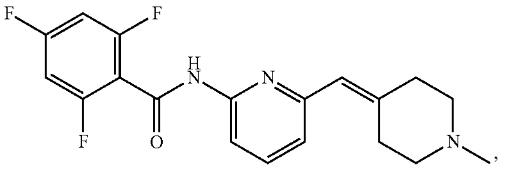

-continued
(6)
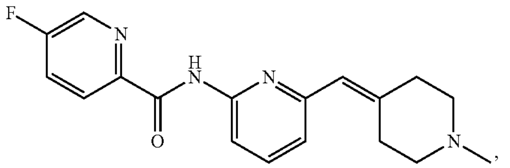
(7)
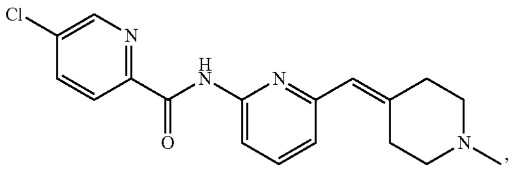
(8)
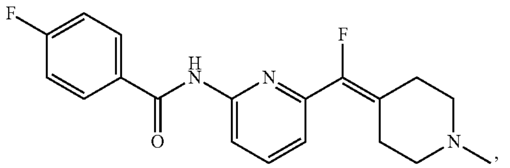
(9)
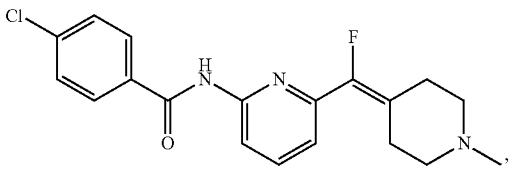
(10)
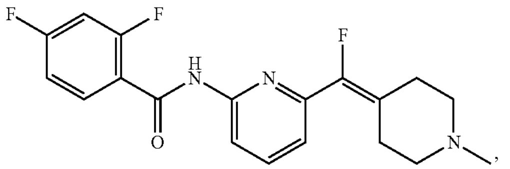
(11)
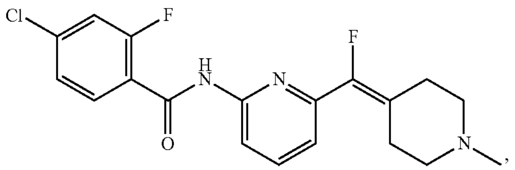
(12)
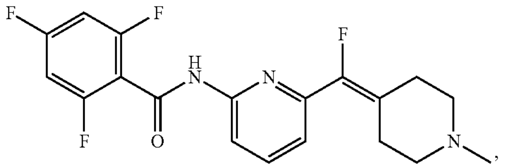
(13)
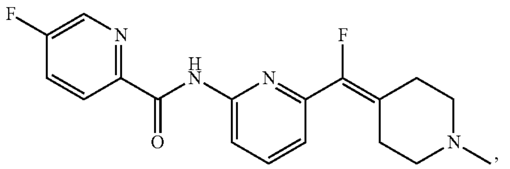
-continued
(14)
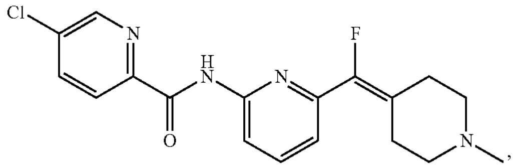
(15)
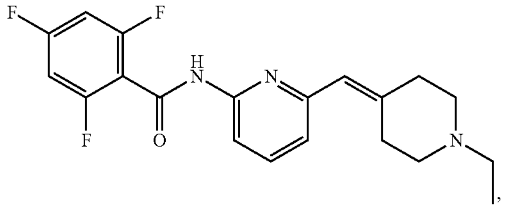
(16)
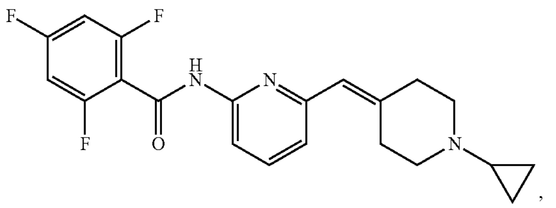
(17)
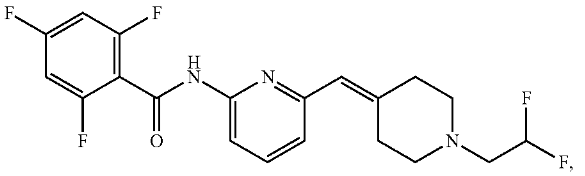
(18)
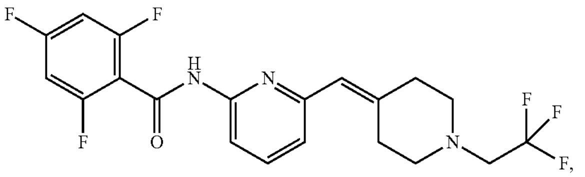
(19)
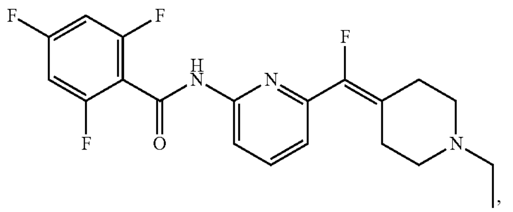
(20)
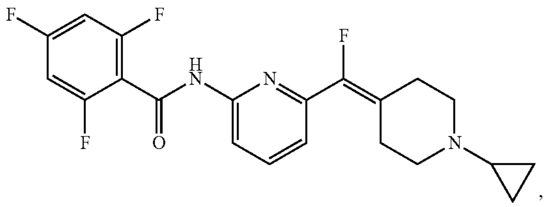

-continued (21)

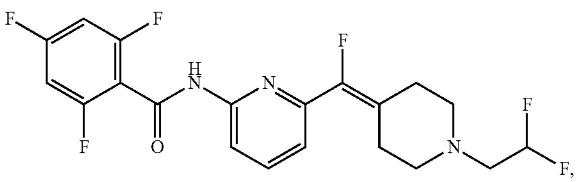

(22)

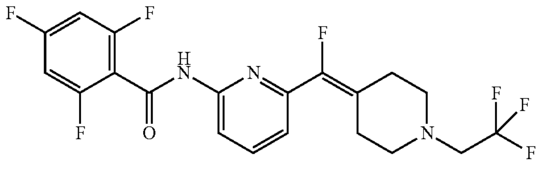

or (23)

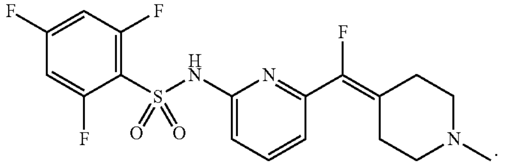

In other aspect, provided herein is a pharmaceutical composition comprising the compound of Formula (I), (II), (III), (IVa), (IVb), (IVc) or (V).

In some embodiments, the pharmaceutical composition disclosed herein further comprises a pharmaceutically acceptable excipient, a carrier, an adjuvant or a combination thereof.

In other aspect, the present invention relates to use of the compound represented by formula (I), (II), (III), (IVa), (IVb), (IVc) or (V) or the pharmaceutical composition in the manufacture of a medicament for preventing, treating or lessening a 5-$HT_{1F}$ receptor-related disease in a patient.

In some embodiments, wherein the 5-$HT_{1F}$ receptor-related disease is migraine, general pain, trigeminal neuralgia, dental pain or temporomandibular joint dysfunction pain, autism, obsession, phobia, depression, social phobia, anxiety, general anxiety disorder, disorders of sleep, post-traumatic syndrome, chronic fatigue syndrome, premenstrual syndrome or late luteal phase syndrome, borderline personality disorder, disruptive behavior disorders, impulse control disorders, attention deficit hyperactivity disorder, alcoholism, tobacco abuse, mutism, trichotillomania, bulimia, anorexia nervosa, premature ejaculation, erectile dysfunction, memory loss or dementia.

In other embodiments, the 5-$HT_{1F}$ receptor-related disease is migraine.

In yet other aspect, the present invention relates to use of the compound represented by formula (I), (II), (III), (IVa), (IVb), (IVc) or (V) or the pharmaceutical composition in the manufacture of a medicament for activating 5-$HT_{1F}$ receptor.

In other aspect, provided herein is a method of preparing, separating or purifying the compound of Formula (I), (II), (III), (IVa), (IVb), (IVc) or (V).

Pharmaceutical Composition of the Compound of the Invention and Preparations and Administration The invention provides a pharmaceutical composition containing a compound of formula (I), (II), (III), (IVa), (IVb), (IVc) or (V) or an independent stereoisomer thereof, a racemic mixture or non-racemic mixture of the stereoisomer thereof, or a pharmaceutically acceptable salt or solvent thereof. In one embodiment of the invention, the pharmaceutical composition further comprises at least one pharmaceutically acceptable carrier, adjuvant or excipient, and optionally other treating and/or preventing ingredients.

The dosage form of the compound used in the method of the invention can be determined by the selected compound, the type of pharmacokinetic distribution required by the route of administration and the state of the patient.

A formulation suitable for oral, sublingual, intranasal or injection administration is prepared according to a well-known method in the pharmaceutical field, and the formulation contains at least one active compound. See, for example, REMINGTON'S PHARMACEUTICAL SCIENCES (16th ed. 1980).

Generally speaking, the formulation of the present invention includes an active ingredient (a compound of formula (I), (II), (III), (IVa), (IVb), (IVc) or (V)), and is usually mixed with excipients, diluted with excipients or encapsulated in carriers that may be in the form of capsules, small capsules, paper or other containers. When an excipient is used as a diluent, it may be a solid, semi-solid or liquid material, acting as an excipient, carrier or medium for the active component. Therefore, the formulations may be tablets, pills, powders, lozenges, sachets, flat capsules, elixir, suspension, emulsion, solution, syrup, aerosol (solid or liquid medium), ointments containing an active compound up to 10 wt %, soft and hard capsules, gelatin, suppository, sterile injection and aseptic packaging powder.

Before mixing with other components in preparation process, the active compound may need to be ground to provide appropriate particle size. If the active compound is insoluble, it is usually ground to a size of less than 200 mesh. If the active compound is basically water-soluble, its particle size is adjusted by grinding, so that the compound has an uniform particle size distribution in the formulation, for example, about 40 meshes. In one embodiment of the present invention, the particle size is about 0.1-100 μm.

A suitable carrier, adjuvant or excipient is well known for the technical personnel in the field and was described in detail in Ansel H. C. et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R. C., Handbook of Pharmaceutical Excipients (2005) Pharmaceutical Press, Chicago.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and/or would result in pharmaceutically unacceptable compositions are avoided. In addition, each excipient must be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Examples of suitable excipients include lactose, glucose, sucrose, sorbitol, mannitol, starch, Arabic gum, calcium phosphate, alginate, xanthate, gelatin, calcium silicate, microcrystalline cellulose, polyvinylpyrrolidone, cellulose, water, syrup and methyl cellulose. Suitable pharmaceutically acceptable excipients further include the following types: diluents, fillers, binders, disintegrants, lubricants (such as talc powder, magnesium stearate and mineral oil), glidants, granulating agents, coating agents, wetting agents, solvents, co-solvents, suspending agents, emulsifiers, sweetners, flavoring agents, flavor masking agents, coloring agents, anticaking agents, humectants, chelating agents, plasticizers, viscosity increasing agents, antioxidants, preservatives (such as methyl hydroxybenzoate and propyl hydroxybenzoate), stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation. The compounds of the invention can be prepared by known methods in the field so that the active components will be released rapidly, continuously or controllably after administration in patients.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

Pharmaceutically acceptable carriers may be solid or liquid carriers for the preparation of pharmaceutical compositions using compounds described in the present invention. Solid formulations include powders, tablets, dispersible granules, capsules, cachets, and suppositories. Powders and tablets may contain about 5% to about 95% active ingredients. Suitable solid carriers are known in the field, such as magnesium carbonate, magnesium stearate, talc powder, sugar or lactose. Tablets, powders, flat capsules and capsules may be used as solid dosage forms suitable for oral administration. Examples of medicinal carriers and methods for preparing various compositions can be obtained as follows: A. Gennaro (ed.), Remington's Pharmaceutical Sciences, $18^{th}$ ed., 1990, Mack Publishing Company Co., Easton, Pennsylvania In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York disclosed various carriers used in formulating pharmaceutically acceptable compositions and known techniques for the preparation thereof, the contents of each of which is incorporated by reference herein. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

Therefore, another aspect of the present invention is related to a method for preparing a pharmaceutical composition, wherein the pharmaceutical composition contains the compound disclosed herein and pharmaceutically acceptable excipient, carrier, adjuvant, vehicle or a combination thereof, and the method comprises mixing various ingredients. The pharmaceutical composition containing the compound disclosed herein can be prepared at for example environment temperature and under barometric pressure.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

It will also be appreciated that certain of the compounds of present invention can exist in free form for treatment, or where appropriate, as a pharmaceutically acceptable derivative. According to the present invention, a pharmaceutically acceptable derivative includes, but is not limited to, pharmaceutically acceptable prodrugs, salts, esters, salts of such esters, or any other adduct or derivative which upon administration to a patient in need thereof is capable of providing, directly or indirectly, a compound as described herein, or a metabolite or residue thereof.

In one embodiment, the compounds disclosed herein can be prepared to oral administration. In the other embodiment, the compounds disclosed herein can be prepared to inhalation. In the still other embodiment, the compounds disclosed herein can be prepared to nasal administration. In the yet other embodiment, the compounds disclosed herein can be prepared to transdermal administration. In the still yet other embodiments, the compounds disclosed herein can be prepared to topical administration.

The pharmaceutical compositions provided herein may be provided as compressed tablets, tablet triturates, chewable lozenges, rapidly dissolving tablets, multiple compressed tablets, enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

The pharmaceutical composition of the invention can be prepared to a dosage form adapted for administration to a patient by inhalation, for example as a dry powder, an aerosol, a suspension, or a solution composition. In one embodiment, the pharmaceutical composition disclosed in the invention is directed to a dosage form adapted for administration to a patient by inhalation as a dry powder. In one embodiment, the pharmaceutical composition disclosed in the invention is directed to a dosage form adapted for administration to a patient by inhalation as a nebulizer. Dry powder compositions for delivery to the lung by inhalation typically comprise a compound disclosed herein as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (e.g., micronised) compound can be defined by a $D_{50}$ value of about 1 to about 10 microns (for example as measured using laser diffraction).

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine substituted by palmitoyl radicals. The compounds may furthermore be coupled to a class of biodegradable polymers which are suitable for achieving controlled release of a medicament, for example polylactic acid, poly-ε-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be administered parenterally by injection, infusion, or implantation, for local or systemic administration. Parenteral administration, as used herein, includes intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

The pharmaceutical compositions provided herein can be administered by rectal in suppository form, in which the drug was mixed with suitable non-irritating excipients such as cocoa oil and glycerol ester synthesized by polyethylene glycol, and the mixture was solid at room temperature and can be released when liquefied or dissolved in the rectal cavity. Because of individual differences, the severity of symptoms between individuals will have great difference, and every drug has its unique therapeutic properties. Therefore, the exact way of administration, dosage form and treatment plan for each individual should be determined by a practicing physician.

The pharmaceutical compositions provided herein may be formulated as immediate or modified release dosage forms, including delayed-, sustained, pulsed-, controlled, targeted-, and programmed-release forms.

While it is possible to administer a compound employed in the methods of this invention directly without any formulation, the compounds are usually administered in the form of pharmaceutical formulations comprising a pharmaceutically acceptable excipient and at least one active ingredient. These formulations can be administered by a variety of routes including oral, buccal, rectal, intranasal, transdermal, subcutaneous, intravenous, intramuscular, and intranasal. Many of the compounds employed in the methods of this invention are effective as both injectable and oral compositions.

In order to administer transdermally, a transdermal delivery device ("patch") is needed. The transdermal patch can be used to continuously or intermittently deliver the controllable amount of the compound of the invention. The structure and application of transdermal patches for drug delivery are well known in the field. See, e.g., U.S. Pat. No. 5,023,252. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472. The delivery of hydrophilic drugs may be enhanced by intra-arterial infusion of hypertonic solutions which can transiently open the blood-brain barrier.

In one preferred embodiment of the present invention, there is provided a pharmaceutical formulation comprising at least one active compound as described above in a formulation adapted for buccal and/or sublingual, or nasal administration. This embodiment provides administration of the active compound in a manner that avoids gastric complications, such as first bypassing gastric system metabolism and/or first undergoing liver metabolism. This administration route may also reduce adsorption times, providing more rapid onset of therapeutic benefit. The compounds of the present invention may provide particularly favorable solubility distributions to facilitate sublingual/buccal formulations. Such formulations typically require relatively high concentrations of active ingredients to deliver sufficient amounts of active ingredients to the limited surface area of the sublingual/buccal mucosa for the relatively short durations of contact with sublingual/buccal mucosal surface, to allow the absorption of the active ingredient. Thus, the very high activity of the compounds of the present invention and their high solubilities facilitate their suitability for sublingual/buccal formulation.

The term "therapeutically effective amount," as used herein, refers to the total amount of each active component that is sufficient to show an useful treatment effect. For example, the drug amount of administration or balance in the body sufficient to treat, cure, or alleviate symptoms of a disease. The effective amount required for a special treatment depends on a variety of factors, including diseases, the severity of the disease, the activity of the used specific drug, the mode of administration, the clearance rate of the specific drug, the duration of therapy, the combination of drugs, age, weight, gender, diet and patient's health, and so on. The description of other factors that need to be considered for "therapeutically effective amount" in this field can be found in Gilman et al., eds., Goodman And Gilman's: The Pharmacological Bases of Therapeutics, $8^{th}$ ed., Pergamon Press, 1990; Remington's Pharmaceutical Sciences, $17^{th}$ ed., Mack Publishing Company, Easton, Pa., 1990.

A compound of formula (I) is preferably formulated in an unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The compounds are generally effective over a wide dosage range. For example, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

The term "administration" refers to provision of a therapeutically effective amount of medicine to an individual by oral, sublingual, intravenous, subcutaneous, percutaneous, intramuscular, intradermal, intrathecal, epidural, intraocular, intracranial, inhalation, rectal, vagina, etc. The pharmaceutical dosage forms include plaster, lotion, tablet, capsule, pill, dispersible powder, granule, suppository, sublimed preparation, lozenge, injection, aseptic solution or non-aqueous solution, suspension, emulsion, paster, etc. An active component is complexed with a non-toxic pharmaceutically acceptable carrier (such as glucose, lactose, gum arabic, gelatin, mannitol, starch paste, magnesium trisilicate, talcum powder, corn starch, keratin, silica gel, potato starch, urea, dextran, etc.).

The preferred route of administration varies with clinical characteristics. Dose changes must depend on situation of patients receiving treatment. Doctors will determine the appropriate dose according to individual status of patients. The therapeutically effective amount per unit dose depends on body weight, physiological function and the selected vaccination program. An amount of compound per unit dose refers to the weight of the compound per each administration, excluding weight of carriers (the drug formulation contains carriers).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

The pharmaceutical compositions provided herein may be co-formulated with other active ingredients which do not impair the desired therapeutic action, or with substances that supplement the desired action.

In one embodiment, the therapeutic methods disclosed herein comprise administrating to a patient in need of the treatment a safe and effective amount of the compound of the invention or the pharmaceutical composition containing the compound of the invention. Each example disclosed herein comprises the method of treating the diseases comprising administrating to a patient in need of the treatment a safe and effective amount of the compound of the invention or the pharmaceutical composition containing the compound of the invention.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. In one embodiment, the compound of the invention or the pharmaceutical composition thereof may be administered orally. In another embodiment, the compound of the invention or the pharmaceutical composition thereof may be administered by inhalation. In still one embodiment, the compound of the invention or the pharmaceutical composition thereof may be administered intranasally.

In one embodiment, the compound of the invention or the pharmaceutical composition thereof may be administered once or according to a dosing regimen wherein a number of doses are administered at varying intervals of time for a given period of time. For example, doses may be administered once, twice, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as absorption, distribution, and half-life, which can be determined by the skilled artisan. In addition, suitable dosing regimens, including the duration of implementation of such regimens, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and the like within the knowledge and expertise of the skilled artisan. It will be further understood by such skilled artisans that suitable dosing regimens may require adjustment given an individual patient's response to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents. This is chosen by the technical personnel in the field according to the actual conditions of the patient's health, age, weight and so on. If formulated as a fixed dose, such combination products employ the compounds of this invention within the dosage range described herein and the other pharmaceutically active agent within its dosage range.

Accordingly, in an aspect, this invention includes combinations comprising an amount of at least one compound of the invention, or a pharmaceutically acceptable salt, solvate, ester or prodrug thereof, and an effective amount of one or more additional agents described above.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Use of the Compounds and Pharmaceutical Compositions

The compounds and pharmaceutical compositions provided by the invention can be used to prepare a medicament for activating $5\text{-HT}_{1F}$ receptors, and also to prepare a medicament for preventing, treating or alleviating a $5\text{-HT}_{1F}$ receptor-related disease, especially migraine.

Specifically, the amount of the compound or the compound of the pharmaceutical composition of the present invention can effectively, detectably and selectively activate $5\text{-HT}_{1F}$ receptor.

Specifically, the amount of the compound or the compound of the pharmaceutical composition of the present invention can effectively, detectably and selectively inhibit neuronal protein extravasation.

Compounds disclosed herein would be useful for, but are in no way limited to, the prevention or treatment or alleviation of a $5\text{-HT}_{1F}$ receptor-related disease in a patient by administering to the patient a compound or a composition disclosed herein in an effective amount. The $5\text{-HT}_{1F}$ receptor-related diseases further include, but are not limited to, migraine, general pain, trigeminal neuralgia, dental pain or temporomandibular joint dysfunction pain, autism, obsession, phobia, depression, social phobia, anxiety, general anxiety disorder, disorders of sleep, post-traumatic syndrome, chronic fatigue syndrome, premenstrual syndrome or late luteal phase syndrome, borderline personality disorder, disruptive behavior disorders, impulse control disorders, attention deficit hyperactivity disorder, alcoholism, tobacco abuse, mutism, trichotillomania, bulimia, anorexia nervosa, premature ejaculation, erectile dysfunction, memory loss and dementia.

Besides being useful for human treatment, the compounds and pharmaceutical compositions of the present invention are also useful for veterinary treatment of animals such as companion animals, exotic animals and farm animals. In other embodiments, the animals disclosed herein include horses, dogs, and cats. As used herein, the compounds disclosed herein include the pharmaceutically acceptable derivatives thereof.

General Synthetic Procedures

The following examples are provided so that the invention might be more fully understood. However, it should be understood that these embodiments merely provide a method of practicing the present invention, and the present invention is not limited to these embodiments.

Generally, the compounds disclosed herein may be prepared by methods described herein, wherein the substituents are as defined for Formula (I), (II), (III), (IVa), (IVb), (IVc) or (V) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known reaction conditions in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjin Fuchen Chemical Reagent Factory, Wuhan XinHuaYuan Technology Development Co. Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous sodium sulfate prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

$^1H$ NMR spectra were recorded by Bruker 400 MHz or 600 MHz NMR spectrometer. $^1H$ NMR spectra were obtained by using $CDCl_3$, DMSO-$d_6$, $CD_3OD$ or acetone-$d_6$ solutions (in ppm), with TMS (0 ppm) or chloroform (7.26 ppm) as the reference standard. When peak multiplicities are reported, the following abbreviations are used: s (singlet), d (doublet), t (triplet), q (quartet), m (multiplet), br (broadened), brs (broadened singlet), dd (doublet of doublets), ddd (doublet of doublet of doublets), dt (doublet of triplets), td (triplet of doublets), tt (triplet of triplets). Coupling constants J, when given, were reported in Hertz (Hz).

Low resolution mass spectrum (MS) data measurement condition: Agilent 6120 Quadrupole HPLC-M (column type: Zorbax SB-C18, 2.1×30 mm, 3.5 micron, 6 min, flow rate 0.6 mL/min. Mobile phase: in the proportion of 5%-95% ($CH_3CN$ containing 0.1% of formic acid) in ($H_2O$ containing 0.1% of formic acid), using electrospray ionization (ESI), UV detection, at 210 nm/254 nm.

Pure compound was detected by Agilent 1260 pre-HPLC or Calesep pump 250 pre-HPLC (NOVASEP 50/80 mm DAC) with UV detection at 210 nm/254 nm.

The following abbreviations are used throughout the specification:

| | |
|---|---|
| $CH_2Cl_2$, DCM | dichloromethane |
| $CDCl_3$ | deuterochloroform |
| DMSO | dimethyl sulfoxide |
| DMSO-$d_6$ | deuterated dimethyl sulfoxide |
| EtOAc, EA | ethyl acetate |
| $CH_3OH$, MeOH | methanol |
| $CD_3OD$ | deuterated methanol |
| nM | nanomole per liter |
| μM | micromole per liter |
| mM | millimole per liter |
| M | mole per liter |
| ng | nanogram |
| μg | microgramme |
| Boc, BOC | tert-butoxycarbonyl |
| mg | milligram |
| g | gram |
| mL, ml | milliliter |
| μL, μl | microliter |
| nL, nl | nanoliter |
| min | minute |
| h | hour |
| PE | petroleum ether (60-90° C.) |
| RT, rt, r.t. | room temperature |
| EDTA-$K_2$ | dipotassium ethylenediaminetetraacetate |
| Solutol | polyoxyl-15-hydroxystearate |
| MTBE | tert-butyl methyl ether |
| PEG400 | polyethylene glycol 400 |
| Et | $CH_3CH_2$, ethyl |

The following synthetic schemes describe the steps for preparing the compounds disclosed herein, unless otherwise specified, wherein each $R^{1a}$, $R^{1b}$, $R^{1c}$, $R^{1d}$ and $R^{1e}$ is as defined herein.

Scheme 1

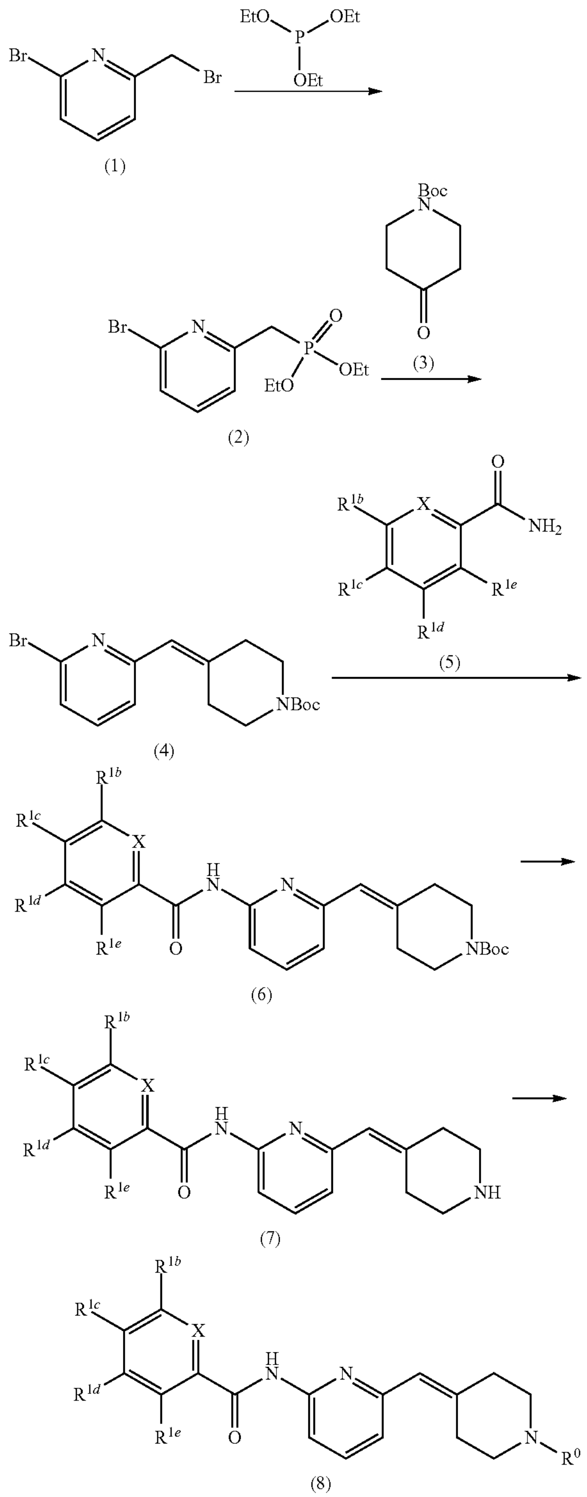

(1) (2) (3) (4) (5) (6) (7) (8)

Wherein X is $CR^{1a}$ or N; $R^0$ is alkyl, cycloalkyl or haloalkyl.

A compound of formula (8) can be prepared through the following process: a compound of formula (1) can react with triethyl phosphite to afford a compound of formula (2); and then the compound of formula (2) can be condensed with a compound of formula (3) to get a compound of formula (4).

The compound of formula (4) can react with a compound of formula (5) to get a compound of formula (6). The compound of formula (6) can convert to a compound of formula (7) through de-protection; the compound of formula (7) can convert to a compound of formula (8) by Borch reductive amination with corresponding aldehyde or ketal in the presence of a reductant (e.g., sodium cyanoborohydride).

Scheme 2

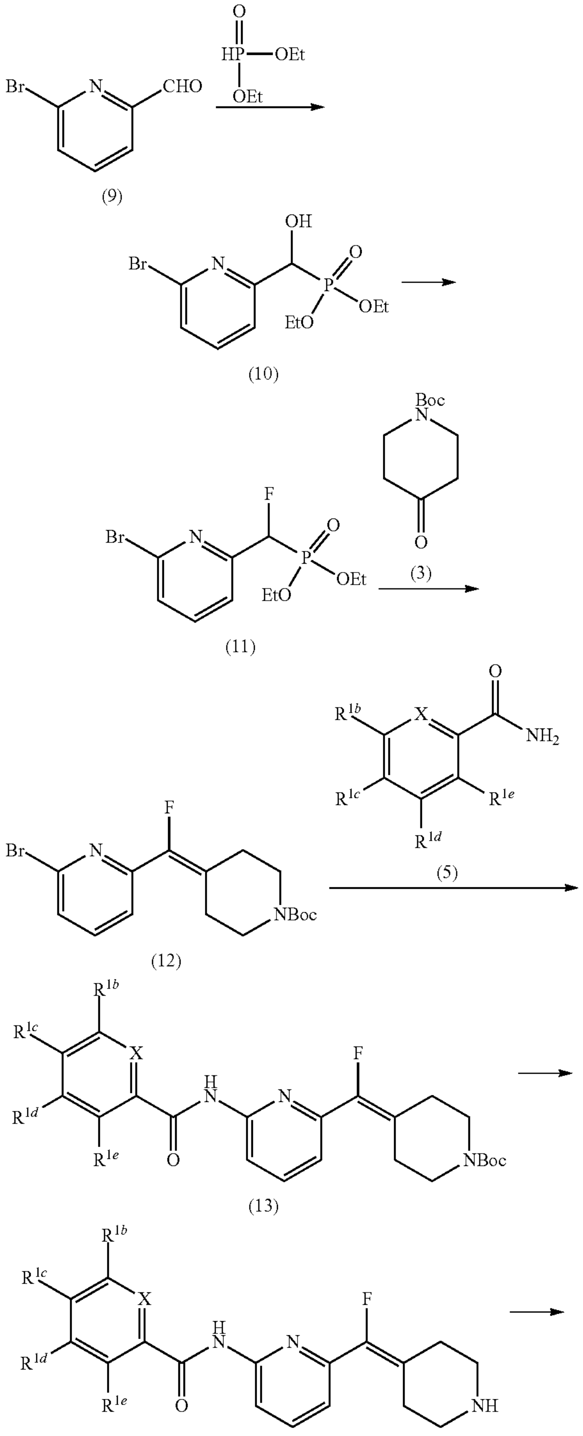

(9) (10) (3) (11) (5) (12) (13) (14)

-continued

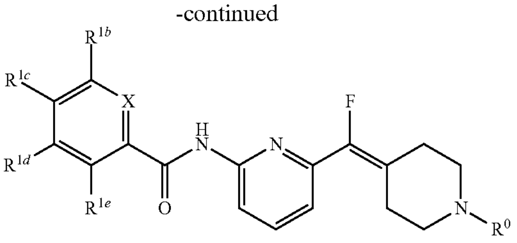

(15)

Wherein X is $CR^{1a}$ or N; $R^0$ is alkyl, cycloalkyl or haloalkyl.

A compound of formula (15) can be prepared through the following process: a compound of formula (9) can react with diethyl phosphite to afford a compound of formula (10); the compound of formula (10) can be fluorinated to get a compound of formula (11); and then the compound of formula (11) can be condensed with a compound of formula (3) to get a compound of formula (12). The compound of formula (12) can react with a compound of formula (5) to get a compound of formula (13). The compound of formula (13) can convert to a compound of formula (14) through de-protection; the compound of formula (14) can convert to a compound of formula (15) by Borch reductive amination with corresponding aldehyde or ketal in the presence of a reductant (e.g., sodium cyanoborohydride).

Scheme 3

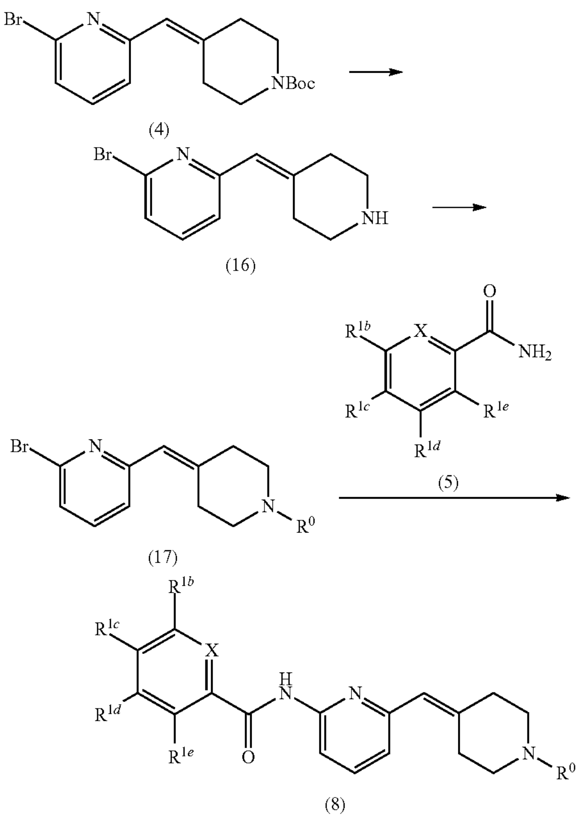

(4)

(16)

(5)

(17)

(8)

Wherein X is $CR^{1a}$ or N; $R^0$ is alkyl, cycloalkyl or haloalkyl.

A compound of formula (8) can be prepared through the following process: a compound of formula (4) can convert to a compound of formula (16) through de-protection; the compound of formula (16) can convert to a compound of formula (17) by nucleophilic substitution reaction with corresponding alkyl derivative or cycloalkyl derivative; and then the compound of formula (17) can be condensed with a compound of formula (5) to get a compound of formula (8).

Scheme 4

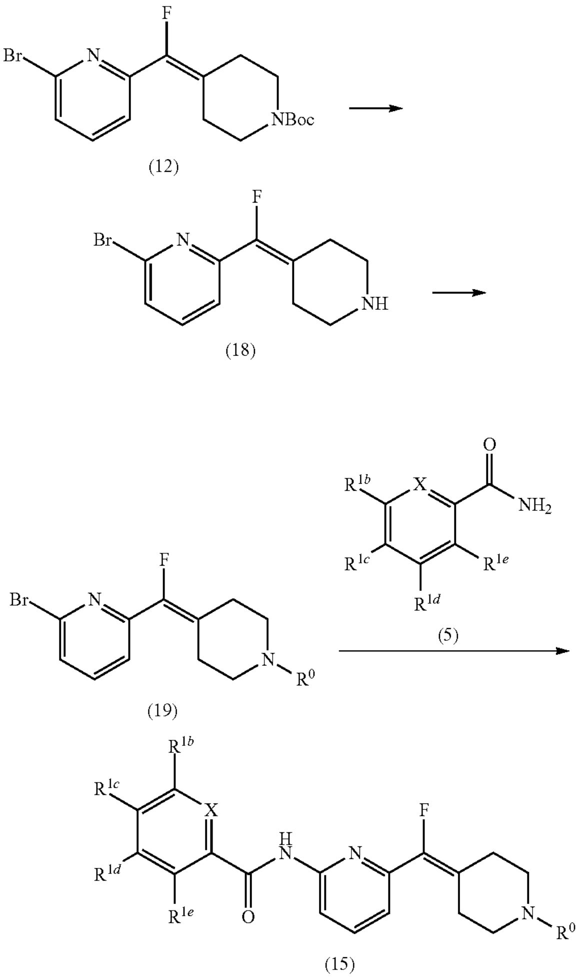

(12)

(18)

(5)

(19)

(15)

Wherein X is $CR^{1a}$ or N; $R^0$ is alkyl, cycloalkyl or haloalkyl.

A compound of formula (15) can be prepared through the following process: a compound of formula (12) can convert to a compound of formula (18) through de-protection; the compound of formula (18) can convert to a compound of formula (19) by nucleophilic substitution reaction with corresponding alkyl derivative or naphthenic derivative; and then the compound of formula (19) can be condensed with a compound of formula (5) to get a compound of formula (15).

The following examples are provided to further illustrate the compounds, pharmaceutical compositions and their applications thereof.

EXAMPLE

Example 1: Synthesis of 4-fluoro-N-(6-((1-methylpiperidin-4-ylidene)methyl)pyridin-2-yl) benzamide

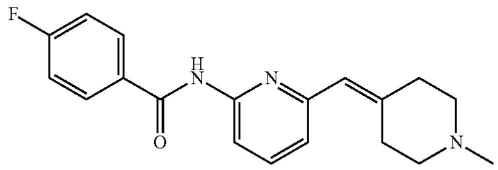 [SMILES: CN1CCC(=Cc2cccc(NC(=O)c3ccc(F)cc3)n2)CC1]

Step 1) Synthesis of diethyl((6-bromopyridin-2-yl)methyl)phosphonate

2-Bromo-6-(bromomethyl)pyridine (5.0 g, 19.9 mmol) and triethyl phosphite (6.0 mL, 35.0 mmol) were added into a 100 mL single-neck round bottom flask, and the mixture was stirred at 140° C. for 12 hours. After the reaction was completed, the mixture was concentrated using a rotary evaporator under reduced pressure. The residue was purified by column chromatography (petroleum ether/ethyl acetate (v/v)=5/1) to get the title compound as light yellow oil (4.91 g, 80.0%).

MS (ESI, pos. ion) m/z: 308.0 $[M+H]^+$;

$^1H$ NMR (400 MHz, $CDCl_3$) δ (ppm) 7.49 (t, J=7.6 Hz, 1H), 7.37-7.33 (m, 2H), 4.13-4.04 (m, 4H), 3.37 (d, J=22.0 Hz, 2H), 1.28 (t, J=7.2 Hz, 6H).

Step 2) Synthesis of tert-butyl 4-((6-bromopyridin-2-yl)methylene)piperidine-1-carboxylate Under 0° C., diethyl((6-bromopyridin-2-yl)methyl)phosphonate (446 mg, 1.45 mmol), tert-butyl 4-oxopiperidine-1-carboxylate (0.6 g, 3.0 mmol) and tetrahydrofuran (10 mL) were added into a 100 mL single-neck round bottom flask, and then sodium hydride (70 mg, 1.75 mmol) was added. After the mixture was stirred for 15 min, the mixture was further stirred at 25° C. for 5 hours. After the reaction was stopped stirring, water (20 mL) was added, and the resulting mixture was extracted with dichloromethane (30 mL×2). The combined organic layers were dried over anhydrous sodium sulfate (2 g) and filtered. The filtrate was concentrated using a rotary evaporator under reduced pressure. The residue was purified by column chromatography (petroleum ether/ethyl acetate (v/v)=5/1) to get the title compound as colorless oil (500 mg, 97.8%).

MS (ESI, pos. ion) m/z: 353.1 $[M+H]^+$;

$^1H$ NMR (400 MHz, $CDCl_3$) δ (ppm) 7.46 (t, J=8.0 Hz, 1H), 7.28 (d, J=6.8 Hz, 1H), 7.08 (d, J=7.6 Hz, 1H), 6.29 (s, 1H), 3.55-3.50 (m, 2H), 3.49-3.44 (m, 2H), 2.85 (brs, 2H), 2.35 (t, J=5.6 Hz, 2H), 1.48 (s, 9H).

Step 3) Synthesis of tert-butyl 4-((6-(4-fluorobenzamide)pyridin-2-yl)methylene)piperidine-1-carboxylate tert-Butyl 4-((6-bromopyridin-2-yl)methylene)piperidine-1-carboxylate (500 mg, 1.42 mmol), 4-fluorobenzamide (348 mg, 2.50 mmol), potassium carbonate (1.38 g, 9.98 mmol), cuprous iodide (280 mg, 1.47 mmol), (1R, 2R)—$N^1$,$N^2$-dimethylcyclohexane-1,2-diamine (122 mg, 0.86 mmol), water (1.3 mL) and toluene (10 mL) were added into a 100 mL single-neck round bottom flask, and the mixture was stirred at 115° C. under $N_2$ protection for 12 hours. After the reaction was stopped stirring, water (20 mL) was added, and the resulting mixture was extracted with dichloromethane (30 mL×2). The combined organic layers were dried over anhydrous sodium sulfate (1.5 g) and filtered. The filtrate was concentrated using a rotary evaporator under reduced pressure. The residue was purified by column chromatography (petroleum ether/ethyl acetate (v/v)= 4/1) to get the title compound as light yellow oil (420 mg, 72.1%).

MS (ESI, pos. ion) m/z: 412.3 $[M+H]^+$;

$^1H$ NMR (400 MHz, $CDCl_3$) δ (ppm) 8.46 (s, 1H), 8.15 (d, J=8.4 Hz, 1H), 7.95-7.88 (m, 2H), 7.69 (t, J=8.0 Hz, 1H), 7.16 (t, J=8.4 Hz, 2H), 6.94 (d, J=7.6 Hz, 1H), 6.27 (s, 1H), 3.52 (t, J=5.6 Hz, 2H), 3.43 (t, J=5.6 Hz, 2H), 2.77 (t, J=5.6 Hz, 2H), 2.35 (t, J=5.6 Hz, 2H), 1.46 (s, 9H).

Step 4) Synthesis of 4-fluoro-N-(6-(piperidin-4-ylidenemethyl)pyridin-2-yl)benzamide Under 25° C., tert-butyl 4-((6-(4-fluorobenzamide)pyridin-2-yl)methylene)piperidine-1-carboxylate (410 mg, 1.0 mmol) and methanol (5 mL) were added into a 50 mL single-neck round bottom flask, and then hydrogen chloride ethyl acetate solution (2 M, 2 mL) was added. The mixture was further stirred for 2 hours. After the reaction was stopped stirring, the mixture was concentrated using a rotary evaporator under reduced pressure, and then saturated sodium bicarbonate aqueous solution (20 mL) was added. The resulting mixture was extracted with dichloromethane (20 mL) and then was partitioned. The organic layer was dried over anhydrous sodium sulfate (2 g) and filtered. The filtrate was concentrated using a rotary evaporator under reduced pressure. The residue was purified by column chromatography (dichloromethane/methanol (v/v)=20/1) to get the title compound as a light yellow solid (200 mg, 64.9%).

MS (ESI, pos. ion) m/z: 312.1 $[M+H]^+$;

$^1H$ NMR (400 MHz, $CD_3OD$) δ (ppm) 8.03-7.94 (m, 3H), 7.75 (t, J=8.0 Hz, 1H), 7.23 (t, J=8.8 Hz, 2H), 7.03 (d, J=7.6 Hz, 1H), 6.42 (s, 1H), 3.36-3.18 (m, 8H).

Step 5) Synthesis of 4-fluoro-N-(6-((1-methylpiperidin-4-ylidene)methyl)pyridin-2-yl) benzamide 4-Fluoro-N-(6-(piperidin-4-ylidenemethyl)pyridin-2-yl) benzamide (200 mg, 0.64 mmol) and methanol (5 mL) were added into a 50 mL single-neck round bottom flask, and two drops of acetic acid were added. Under 0° C., formaldehyde (40%, 0.17 mL, 2.2 mmol) was added, and then sodium cyanoborohydride (122 mg, 1.93 mmol) was added into the reaction mixture in portions. After stirring for 10 min, the mixture was warmed to 25° C. and further stirred for 5 hours. The reaction was quenched with saturated sodium bicarbonate aqueous solution (10 mL), then the resulting mixture was extracted with dichloromethane (20 mL×2). The combined organic layers were dried over anhydrous sodium sulfate (2 g) and filtered. The filtrate was concentrated using a rotary evaporator under reduced pressure, and the residue was purified by column chromatography (dichloromethane/methanol (v/v)=20/1) to give the title compound as a white solid (163 mg, 78.0%).

MS (ESI, pos. ion) m/z: 326.0 $[M+H]^+$;

$^1H$ NMR (400 MHz, $CDCl_3$) δ (ppm) 8.18 (d, J=8.4 Hz, 1H), 7.97 (dd, J=8.4, 5.2 Hz, 2H), 7.71 (t, J=8.0 Hz, 1H), 7.17 (t, J=8.4 Hz, 2H), 6.91 (d, J=7.6 Hz, 1H), 6.33 (s, 1H), 3.32 (brs, 2H), 3.25-3.04 (m, 6H), 2.77 (s, 3H).

Example 2: Synthesis of 4-chloro-N-(6-((1-methylpiperidin-4-ylidene)methyl)pyridin-2-yl) benzamide

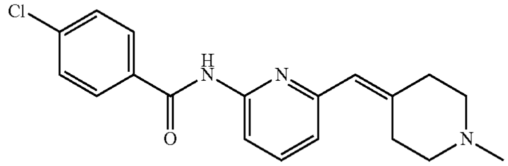 [SMILES: CN1CCC(=Cc2cccc(NC(=O)c3ccc(Cl)cc3)n2)CC1]

Step 1) Synthesis of tert-butyl 4-((6-(4-chlorobenzamide)pyridin-2-yl)methylene)piperidine-1-carboxylate The title compound of this step was prepared by referring to the method described in step 3 of example 1, i.e., tert-butyl 4-((6-bromopyridin-2-yl)methylene)piperidine-1-carboxylate (500 mg, 1.42 mmol), 4-chlorobenzamide (344 mg, 2.21 mmol), potassium carbonate (1.38 g, 9.98 mmol), cuprous iodide (280 mg, 1.47 mmol), (1R,2R)—$N^1$,$N^2$-dimethylcyclohexane-1,2-diamine (122 mg, 0.86 mmol), water (1.3 mL) were reacted in toluene (10 mL) to prepare it. The crude product was purified by silica gel column chromatography (petroleum ether/ethyl acetate (v/v)=4/1) to get the title compound as a white solid (420 mg, 69.3%).

MS (ESI, pos. ion) m/z: 428.1 $[M+H]^+$;

$^1$H NMR (400 MHz, $CDCl_3$) δ (ppm) 8.43 (s, 1H), 8.16 (d, J=8.0 Hz, 1H), 7.85 (d, J=8.4 Hz, 2H), 7.70 (t, J=8.0 Hz, 1H), 7.47 (d, J=8.8 Hz, 2H), 6.95 (d, J=7.6 Hz, 1H), 6.29 (s, 1H), 3.53 (t, J=5.6 Hz, 2H), 3.45 (t, J=5.6 Hz, 2H), 2.78 (t, J=5.6 Hz, 2H), 2.36 (t, J=5.6 Hz, 2H), 1.49 (s, 9H).

Step 2) Synthesis of 4-chloro-N-(6-(piperidin-4-ylidenemethyl)pyridin-2-yl)benzamide The title compound of this step was prepared by referring to the method described in step 4 of example 1, i.e., tert-butyl 4-((6-(4-chlorobenzamide)pyridin-2-yl)methylene)piperidine-1-carboxylate (420 mg, 0.98 mmol) and hydrogen chloride ethyl acetate solution (2 M, 2 mL) was reacted in methanol (5 mL) to prepared it. The crude product was purified by silica gel column chromatography (dichloromethane/methanol (v/v)=20/1) to give the title compound as a light yellow solid (220 mg, 68.6%).

MS (ESI, pos. ion) m/z: 328.2 $[M+H]^+$;

$^1$H NMR (400 MHz, $CD_3OD$) δ (ppm) 7.97 (d, J=8.4 Hz, 1H), 7.92 (d, J=8.8 Hz, 2H), 7.73 (t, J=8.0 Hz, 1H), 7.50 (d, J=8.4 Hz, 2H), 7.01 (d, J=7.6 Hz, 1H), 6.30 (s, 1H), 3.06-2.98 (m, 4H), 2.96 (d, J=5.6 Hz, 2H), 2.43 (t, J=5.6 Hz, 2H).

Step 3) Synthesis of 4-chloro-N-(6-((1-methylpiperidin-4-ylidene)methyl)pyridin-2-yl) benzamide The title compound of this step was prepared by referring to the method described in step 5 of example 1, i.e., 4-chloro-N-(6-(piperidin-4-ylidenemethyl)pyridin-2-yl) benzamide (220 mg, 0.67 mmol), sodium cyanoborohydride (131 mg, 2.18 mmol) and formaldehyde (40%, 0.1 mL, 1.38 mmol) were reacted in methanol (5 mL) to prepare it. The crude product was purified by silica gel column chromatography (dichloromethane/methanol (v/v)=30/1) to give the title compound as a white solid (228 mg, 99.4%).

MS (ESI, pos. ion) m/z: 342.1 $[M+H]^+$;

$^1$H NMR (400 MHz, $CDCl_3$) δ (ppm) 8.18 (d, J=8.0 Hz, 1H), 7.89 (d, J=8.4 Hz, 2H), 7.71 (t, J=8.0 Hz, 1H), 7.47 (d, J=8.4 Hz, 2H), 6.93 (d, J=7.6 Hz, 1H), 6.31 (s, 1H), 3.18 (br, 2H), 3.01-2.89 (m, 4H), 2.68-2.62 (m, 2H), 2.61 (s, 3H).

Example 3: Synthesis of 2,4-difluoro-N-(6-((1-methylpiperidin-4-ylidene)methyl)pyridine-2-yl) benzamide

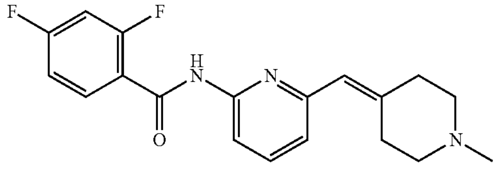 [SMILES: CN1CCC(=Cc2cccc(NC(=O)c3ccc(F)cc3F)n2)CC1]

Step 1) Synthesis of tert-butyl 4-((6-(2,4-difluorobenzamide)pyridin-2-yl)methylene)piperidine-1-carboxylate The title compound of this step was prepared by referring to the method described in step 3 of example 1, i.e., tert-butyl 4-((6-bromopyridin-2-yl)methylene)piperidine-1-carboxylate (500 mg, 1.42 mmol), 2,4-difluorobenzamide (363 mg, 2.31 mmol), potassium carbonate (1.38 g, 9.98 mmol), cuprous iodide (280 mg, 1.47 mmol), (1R,2R)—$N^1$, $N^2$-dimethylcyclohexane-1,2-diamine (122 mg, 0.86 mmol), water (1.3 mL) were reacted in toluene (10 mL) to prepare it. The crude product was purified by silica gel column chromatography (petroleum ether/ethyl acetate (v/v)=4/1) to get the title compound as a white solid (501 mg, 82.2%).

MS (ESI, pos. ion) m/z: 430.1 $[M+H]^+$;

$^1$H NMR (400 MHz, $CDCl_3$) δ (ppm) 8.89 (d, J=13.2 Hz, 1H), 8.23-8.12 (m, 2H), 7.69 (t, J=8.0 Hz, 1H), 7.08-7.02 (m, 1H), 6.99-6.91 (m, 2H), 6.30 (s, 1H), 3.54 (t, J=5.6 Hz, 2H), 3.47 (t, J=5.6 Hz, 2H), 2.85 (t, J=5.6 Hz, 2H), 2.37 (t, J=5.6 Hz, 2H), 1.48 (s, 9H).

Step 2) Synthesis of 2,4-difluoro-N-(6-(piperidin-4-ylidenemethyl)pyridin-2-yl)benzamide The title compound of this step was prepared by referring to the method described in step 4 of example 1, i.e., tert-butyl 4-((6-(2,4-fluorobenzamide)pyridin-2-yl)methylene) piperidine-1-carboxylate (481 mg, 1.12 mmol) and hydrogen chloride ethyl acetate solution (2 M, 4 mL) was reacted in methanol (5 mL) to prepared it. The crude product was purified by silica gel column chromatography (dichloromethane/methanol (v/v)=20/1) to give the title compound as a light yellow solid (315 mg, 85.4%).

MS (ESI, pos. ion) m/z: 330.0 $[M+H]^+$;

$^1$H NMR (400 MHz, $CD_3OD$) δ (ppm) 8.02 (d, J=8.0 Hz, 1H), 7.91-7.83 (m, 1H), 7.76 (t, J=8.0 Hz, 1H), 7.17-7.08 (m, 2H), 7.04 (d, J=7.6 Hz, 1H), 6.39 (s, 1H), 3.27-3.23 (m, 2H), 3.22-3.18 (m, 2H), 3.17-3.11 (m, 2H), 2.55 (t, J=5.6 Hz, 2H).

Step 3) Synthesis of 2,4-difluoro-N-(6-((1-methylpiperidin-4-ylidene)methyl)pyridin-2-yl) benzamide The title compound of this step was prepared by referring to the method described in step 5 of example 1, i.e., 2,4-difluoro-N-(6-(piperidin-4-ylidenemethyl)pyridin-2-yl) benzamide (295 mg, 0.90 mmol), sodium cyanoborohydride (177 mg, 2.81 mmol) and formaldehyde (40%, 0.13 mL, 1.82 mmol) were reacted in methanol (5 mL) to prepare it. The crude product was purified by silica gel column chromatography (dichloromethane/methanol (v/v)=30/1) to give the title compound as a white solid (136 mg, 44.2%).

MS (ESI, pos. ion) m/z: 344.1 $[M+H]^+$;

$^1$H NMR (400 MHz, $CDCl_3$) δ (ppm) 8.21-8.10 (m, 2H), 7.71 (t, J=8.0 Hz, 1H), 7.09-7.01 (m, 1H), 6.99-6.90 (m, 2H), 6.33 (s, 1H), 3.26 (br, 2H), 3.13-2.99 (m, 6H), 2.67 (s, 3H).

Example 4: Synthesis of 4-chloro-2-fluoro-N-(6-((1-methylpiperidin-4-ylidene)methyl) pyridine-2-yl)benzamide

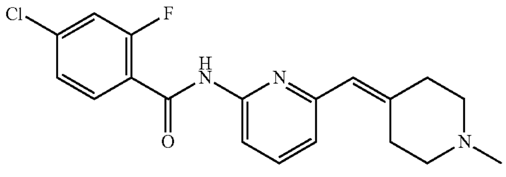 [SMILES: CN1CCC(=Cc2cccc(NC(=O)c3ccc(Cl)cc3F)n2)CC1]

Step 1) Synthesis of tert-butyl 4-((6-(4-chloro-2-fluorobenzamide)pyridin-2-yl)methylene) piperidine-1-carboxylate The title compound of this step was prepared by referring to the method described in step 3 of example 1, i.e., tert-butyl 4-((6-bromopyridin-2-yl)methylene)piperidine-1-carboxylate (500 mg, 1.42 mmol), 4-chloro-2-fluoro-benzamide (344 mg, 1.98 mmol), potassium carbonate (1.38 g, 9.98 mmol), cuprous iodide (280 mg, 1.47 mmol), (1R, 2R)—$N^1$,$N^2$-dimethylcyclohexane-1,2-diamine (122 mg, 0.86 mmol), water (1.3 mL) were reacted in toluene (10 mL) to prepare it. The crude product was purified by silica gel column chromatography (petroleum ether/ethyl acetate (v/v)= 4/1) to get the title compound as a light yellow solid (470 mg, 74.5%).

MS (ESI, pos. ion) m/z: 446.2 $[M+H]^+$;

$^1$H NMR (400 MHz, $CDCl_3$) δ (ppm) 8.90 (d, J=12.8 Hz, 1H), 8.15 (d, J=8.4 Hz, 1H), 8.11 (t, J=8.8 Hz, 1H), 7.70 (t, J=8.0 Hz, 1H), 7.32 (dd, J=8.4, 1.6 Hz, 1H), 7.23 (d, J=1.6 Hz, 1H), 6.96 (d, J=7.6 Hz, 1H), 6.30 (s, 1H), 3.54 (t, J=5.6 Hz, 2H), 3.47 (t, J=5.6 Hz, 2H), 2.85 (t, J=5.6 Hz, 2H), 2.37 (t, J=5.6 Hz, 2H), 1.48 (s, 9H).

Step 2) Synthesis of 4-chloro-2-fluoro-N-(6-(piperidin-4-ylidenemethyl)pyridin-2-yl)benzamide The title compound of this step was prepared by referring to the method described in step 4 of example 1, i.e., tert-butyl 4-((6-(4-chloro-2-fluorobenzamide)pyridin-2-yl) methylene) piperidine-1-carboxylate (453 mg, 1.02 mmol) and hydrogen chloride ethyl acetate solution (2 M, 4 mL) was reacted in methanol (5 mL) to prepared it. The crude product was purified by silica gel column chromatography (dichloromethane/methanol (v/v)=20/1) to give the title compound as a light yellow solid (345 mg, 98.2%).

MS (ESI, pos. ion) m/z: 346.2 $[M+H]^+$;

$^1$H NMR (600 MHz, $CD_3OD$) δ (ppm) 8.00 (d, J=8.0 Hz, 1H), 7.81-7.75 (m, 1H), 7.75-7.69 (m, 1H), 7.37-7.30 (m, 2H), 7.03-6.98 (m, 1H), 6.31 (s, 1H), 3.15-3.03 (m, 6H), 2.48 (brs, 2H).

Step 3) Synthesis of 4-chloro-2-fluoro-N-(6-((1-methylpiperidin-4-ylidene)methyl)pyridin-2-yl) benzamide The title compound of this step was prepared by referring to the method described in step 5 of example 1, i.e., 4-chloro-2-fluoro-N-(6-(piperidin-4-ylidenemethyl)pyridin-2-yl) benzamide (336 mg, 0.97 mmol), sodium cyanoborohydride (147 mg, 2.34 mmol) and formaldehyde (40%, 0.19 mL, 2.72 mmol) were reacted in methanol (5 mL) to prepare it. The crude product was purified by silica gel column chromatography (dichloromethane/methanol (v/v)=30/1) to give the title compound as a white solid (182 mg, 52.1%).

MS (ESI, pos. ion) m/z: 360.2 $[M+H]^+$;

$^1$H NMR (400 MHz, $CDCl_3$) δ (ppm) 8.15 (d, J=8.0 Hz, 1H), 8.07 (t, J=8.4 Hz, 1H), 7.69 (t, J=8.0 Hz, 1H), 7.30 (dd, J=8.4, 1.6 Hz, 1H), 7.23 (dd, J=11.6, 1.6 Hz, 1H), 6.93 (d, J=7.6 Hz, 1H), 6.29 (s, 1H), 3.20 (t, J=5.6 Hz, 2H), 2.98-2.93 (m, 2H), 2.88 (t, J=5.6 Hz, 2H), 2.68-2.63 (m, 2H), 2.58 (s, 3H).

Example 5: Synthesis of 2,4,6-trifluoro-N-(6-((1-methylpiperidin-4-ylidene)methyl)pyridine-2-yl) benzamide

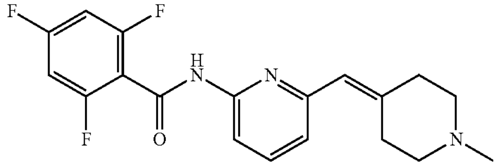 [SMILES: CN1CCC(=Cc2cccc(NC(=O)c3c(F)cc(F)cc3F)n2)CC1]

Step 1) Synthesis of tert-butyl 4-((6-(2,4,6-trifluorobenzamide)pyridin-2-yl)methylene) piperidine-1-carboxylate The title compound of this step was prepared by referring to the method described in step 3 of example 1, i.e., tert-butyl 4-((6-bromopyridin-2-yl)methylene)piperidine-1-carboxylate (500 mg, 1.42 mmol), 2,4,6-trifluorobenzamide (390 mg, 2.23 mmol), potassium carbonate (1.38 g, 9.98 mmol), cuprous iodide (280 mg, 1.47 mmol), (1R,2R)—$N^1$, $N^2$-dimethylcyclohexane-1,2-diamine (122 mg, 0.86 mmol), water (1.3 mL) were reacted in toluene (10 mL) to prepare it. The crude product was purified by silica gel column chromatography (petroleum ether/ethyl acetate (v/v)=4/1) to get the title compound as a light yellow solid (241 mg, 38%).

MS (ESI, pos. ion) m/z: 448.1 $[M+H]^+$;

$^1$H NMR (400 MHz, $CDCl_3$) δ (ppm) 8.15 (d, J=8.4 Hz, 1H), 7.74-7.69 (m, 1H), 6.96 (d, J=7.6 Hz, 1H), 6.77 (t, J=8.0 Hz, 2H), 6.24 (s, 1H), 3.56-3.50 (m, 2H), 3.52 (t, J=5.6 Hz, 2H), 2.80 (t, J=5.6 Hz, 2H), 2.36 (t, J=5.6 Hz, 2H), 1.47 (s, 9H).

Step 2) Synthesis of 2,4,6-trifluoro-N-(6-(piperidin-4-ylidenemethyl)pyridin-2-yl)benzamide The title compound of this step was prepared by referring to the method described in step 4 of example 1, i.e., tert-butyl 4-((6-(2,4,6-trifluorobenzamide)pyridin-2-yl) methylene) piperidine-1-carboxylate (825 mg, 1.84 mmol) and hydrogen chloride ethyl acetate solution (2 M, 4 mL) was reacted in methanol (10 mL) to prepare it. The crude product was purified by silica gel column chromatography (dichloromethane/methanol (v/v)=20/1) to give the title compound as a light yellow solid (490 mg, 76.5%).

MS (ESI, pos. ion) m/z: 348.1 $[M+H]^+$;

$^1$H NMR (400 MHz, $CDCl_3$) δ (ppm) 8.19 (d, J=8.2 Hz, 1H), 7.78-7.71 (m, 1H), 7.05 (d, J=7.6 Hz, 1H), 7.01-6.75 (m, 2H), 6.29 (s, 1H), 3.31-3.12 (m, 4H), 2.70 (brs, 2H).

Step 3) Synthesis of 2,4,6-trifluoro-N-(6-((1-methylpiperidin-4-ylidene)methyl)pyridin-2-yl) benzamide The title compound of this step was prepared by referring to the method described in step 5 of example 1, i.e., 2,4,6-trifluoro-N-(6-(piperidin-4-ylidenemethyl)pyridin-2-yl)benzamide (471 mg, 1.36 mmol), sodium cyanoborohydride (246 mg, 3.9 mmol) and formaldehyde (40%, 0.19 mL, 2.72 mmol) were reacted in methanol (5 mL) to prepare it. The crude product was purified by silica gel column chromatography (dichloromethane/methanol (v/v)=30/1) to give the title compound as a white solid (427 mg, 87.1%).

MS (ESI, pos. ion) m/z: 362.3 $[M+H]^+$;

$^1$H NMR (400 MHz, $CDCl_3$) δ (ppm) 8.15 (d, J=8.4 Hz, 1H), 7.71 (t, J=8.0 Hz, 1H), 6.92 (d, J=7.2 Hz, 1H), 6.75 (t, J=8.4 Hz, 2H), 6.27 (s, 1H), 3.06-2.96 (m, 6H), 2.76-2.70 (m, 2H), 2.67 (s, 3H).

Example 6: Synthesis of 5-fluoro-N-(6-((1-methylpiperidin-4-ylidene)methyl)pyridin-2-yl) picolinamide

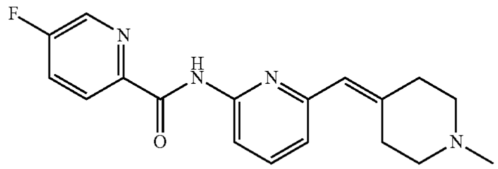 [SMILES: CN1CCC(=Cc2cccc(NC(=O)c3ccc(F)cn3)n2)CC1]

Step 1) Synthesis of tert-butyl 4-((6-(5-fluoropicolinamide)pyridin-2-yl)methylene)piperidine-1-carboxylate The title compound of this step was prepared by referring to the method described in step 3 of example 1, i.e., tert-butyl 4-((6-bromopyridin-2-yl)methylene)piperidine-1-carboxylate (500 mg, 1.42 mmol), 5-fluoro-picolinamide (439 mg, 3.13 mmol), potassium carbonate (1.38 g, 9.98 mmol), cuprous iodide (280 mg, 1.47 mmol), (1R,2R)—$N^1$, $N^2$-dimethylcyclohexane-1,2-diamine (122 mg, 0.86 mmol), water (1.3 mL) were reacted in toluene (10 mL) to prepare it. The crude product was purified by silica gel column chromatography (petroleum ether/ethyl acetate (v/v)=4/1) to get the title compound as a light yellow solid (372 mg, 63.4%).

MS (ESI, pos. ion) m/z: 413.1 $[M+H]^+$;

$^1$H NMR (400 MHz, $CDCl_3$) δ (ppm) 10.23 (s, 1H), 8.48 (d, J=2.4 Hz, 1H), 8.33 (dd, J=8.4, 4.4 Hz, 1H), 8.20 (d, J=8.4 Hz, 1H), 7.70 (t, J=8.0 Hz, 1H), 7.59 (td, J=8.4, 2.8 Hz, 1H), 6.95 (d, J=7.6 Hz, 1H), 6.32 (s, 1H), 3.54 (t, J=5.6 Hz, 2H), 3.48 (t, J=5.6 Hz, 2H), 2.87 (t, J=5.6 Hz, 2H), 2.37 (t, J=5.2 Hz, 2H), 1.48 (s, 9H).

Step 2) Synthesis of 5-fluoro-N-(6-(piperidin-4-ylidenemethyl)pyridin-2-yl)picolinamide The title compound of this step was prepared by referring to the method described in step 4 of example 1, i.e., tert-butyl 4-((6-(5-fluoropicolinamide)pyridin-2-yl)methylene) piperidine-1-carboxylate (355 mg, 0.86 mmol) and hydrogen chloride ethyl acetate solution (2 M, 2 mL) was reacted in methanol (5 mL) to prepare it. The crude product was purified by silica gel column chromatography (dichloromethane/methanol (v/v)=20/1) to give the title compound as a light yellow solid (252 mg, 93.8%).

MS (ESI, pos. ion) m/z: 313.1 $[M+H]^+$;

$^1$H NMR (600 MHz, $CDCl_3$) δ (ppm) 8.52 (dd, J=8.4, 4.2 Hz, 1H), 8.42 (d, J=8.4 Hz, 1H), 7.91 (t, J=7.8 Hz, 1H), 7.79 (td, J=8.4, 3.0 Hz, 1H), 7.45 (d, J=1.2 Hz, 1H), 7.11 (d, J=7.8 Hz, 1H), 6.55 (s, 1H), 3.62-3.58 (m, 2H), 3.52 (t, J=5.4 Hz, 2H), 3.49-3.45 (m, 2H), 2.94 (t, J=5.4 Hz, 2H).

Step 3) Synthesis of 5-fluoro-N-(6-((1-methylpiperidin-4-ylidene)methyl)pyridin-2-yl) picolinamide The title compound of this step was prepared by referring to the method described in step 5 of example 1, i.e., 5-fluoro-N-(6-(piperidin-4-ylidenemethyl)pyridin-2-yl)picolinamide (242 mg, 0.77 mmol), sodium cyanoborohydride (147 mg, 2.34 mmol) and formaldehyde (40%, 0.16 mL, 2.31 mmol) were reacted in methanol (5 mL) to prepare it. The crude product was purified by silica gel column chromatography (dichloromethane/methanol (v/v)=20/1) to give the title compound as a white solid (221 mg, 87.4%).

MS (ESI, pos. ion) m/z: 327.2 $[M+H]^+$;

$^1$H NMR (400 MHz, $CDCl_3$) δ (ppm) 8.48 (d, J=2.8 Hz, 1H), 8.31 (dd, J=8.7, 4.5 Hz, 1H), 8.21 (d, J=8.4 Hz, 1H), 7.70 (t, J=8.0 Hz, 1H), 7.59 (td, J=8.4, 2.8 Hz, 1H), 6.91 (d, J=7.6 Hz, 1H), 6.35 (s, 1H), 3.49 (brs, 2H), 3.25-3.13 (m, 4H), 2.81 (brs, 2H), 2.79 (s, 3H).

Example 7: Synthesis of 5-chloro-N-(6-((1-methylpiperidin-4-ylidene)methyl)pyridin-2-yl) picolinamide

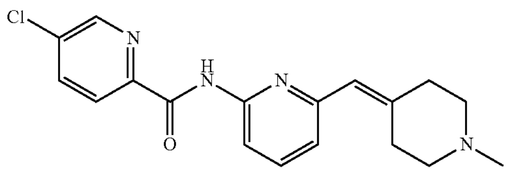

Step 1) Synthesis of tert-butyl 4-((6-(5-chloropicolinamide)pyridin-2-yl)methylene)piperidine-1-carboxylate The title compound of this step was prepared by referring to the method described in step 3 of example 1, i.e., tert-butyl 4-((6-bromopyridin-2-yl)methylene)piperidine-1-carboxylate (500 mg, 1.42 mmol), 5-chloro-picolinamide (451 mg, 2.88 mmol), potassium carbonate (1.38 g, 9.98 mmol), cuprous iodide (280 mg, 1.47 mmol), (1R,2R)—$N^1$, $N^2$-dimethylcyclohexane-1,2-diamine (122 mg, 0.86 mmol), water (1.3 mL) were reacted in toluene (10 mL) to prepare it. The crude product was purified by silica gel column chromatography (petroleum ether/ethyl acetate (v/v)=4/1) to get the title compound as a light yellow solid (200 mg, 32.9%).

MS (ESI, pos. ion) m/z: 429.1 $[M+H]^+$;

$^1$H NMR (400 MHz, $CDCl_3$) δ (ppm) 10.25 (s, 1H), 8.59 (d, J=1.6 Hz, 1H), 8.26-8.20 (m, 2H), 7.88 (dd, J=8.4, 2.4 Hz, 1H), 7.71 (t, J=8.0 Hz, 1H), 6.95 (d, J=7.2 Hz, 1H), 6.32 (s, 1H), 3.57-3.51 (m, 2H), 3.48 (t, J=5.6 Hz, 2H), 2.86 (t, J=5.6 Hz, 2H), 2.41-2.34 (m, 2H), 1.48 (s, 9H).

Step 2) Synthesis of 5-chloro-N-(6-(piperidin-4-ylidenemethyl)pyridin-2-yl)picolinamide The title compound of this step was prepared by referring to the method described in step 4 of example 1, i.e., tert-butyl 4-((6-(5-chloro-picolinamide)pyridin-2-yl)methylene) piperidine-1-carboxylate (188 mg, 0.44 mmol) and hydrogen chloride ethyl acetate solution (2 M, 2 mL) was reacted in methanol (5 mL) to prepare it. The crude product was purified by silica gel column chromatography (dichloromethane/methanol (v/v)=20/1) to give the title compound as alight yellow solid (139 mg, 96.5%).

MS (ESI, pos. ion) m/z: 329.1 $[M+H]^+$;

$^1$H NMR (600 MHz, $CDCl_3$) δ (ppm) 10.22 (s, 1H), 8.61 (d, J=2.4 Hz, 1H), 8.25 (d, J=8.4 Hz, 2H), 7.89 (dd, J=8.4, 2.4 Hz, 1H), 7.73 (t, J=7.8 Hz, 1H), 6.94 (d, J=7.8 Hz, 1H), 6.38 (s, 1H), 3.42 (t, J=5.4 Hz, 2H), 3.36 (t, J=5.4 Hz, 2H), 3.31 (t, J=5.4 Hz, 2H), 2.77 (t, J=5.4 Hz, 2H).

Step 3) Synthesis of 5-chloro-N-(6-((1-methylpiperidin-4-ylidene)methyl)pyridin-2-yl) picolinamide The title compound of this step was prepared by referring to the method described in step 5 of example 1, i.e., 5-chloro-N-(6-(piperidin-4-ylidenemethyl)pyridin-2-yl)picolinamide (134 mg, 0.41 mmol), sodium cyanoborohydride (79 mg, 1.25 mmol) and formaldehyde (40%, 0.08 mL, 1.2 mmol) were reacted in methanol (5 mL) to prepare it. The crude product was purified by silica gel column chromatography (dichloromethane/methanol (v/v)=20/1) to give the title compound as a white solid (108 mg, 77.3%).

MS (ESI, pos. ion) m/z: 343.1 $[M+H]^+$;

$^1$H NMR (400 MHz, $CDCl_3$) δ (ppm) 8.59 (d, J=2.0 Hz, 1H), 8.22 (t, J=8.8 Hz, 2H), 7.87 (dd, J=8.4, 2.4 Hz, 1H), 7.70 (t, J=8.0 Hz, 1H), 6.93 (d, J=7.6 Hz, 1H), 6.32 (s, 1H), 3.21 (t, J=5.6 Hz, 2H), 2.92 (t, J=5.6 Hz, 2H), 2.86 (t, J=5.6 Hz, 2H), 2.64 (t, J=5.6 Hz, 2H), 2.56 (s, 3H).

Example 8: Synthesis of 4-fluoro-N-(6-(fluoro(1-methylpiperidin-4-ylidene)methyl)pyridine-2-yl) benzamide

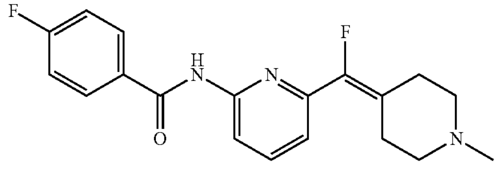 [SMILES: CN1CCC(=C(F)c2cccc(NC(=O)c3ccc(F)cc3)n2)CC1]

Step 1) Synthesis of diethyl((6-bromopyridin-2-yl)(hydroxy)methyl)phosphonate

6-Bromopyridylaldehyde (4.0 g, 21.5 mmol) and diethyl phosphite (3.6 mL, 28 mmol) were added into a 100 mL single-neck round bottom flask, and then ethanol (20 mL) and triethylamine (1.5 mL, 11 mmol) were added. The mixture was stirred at 65° C. for 2 hours. After the reaction was completed, the mixture was concentrated using a rotary evaporator under reduced pressure. The residue was purified by column chromatography (petroleum ether/ethyl acetate (v/v)=2/1) to get the title compound as a white solid (6.2 g, 89%).

MS (ESI, pos. ion) m/z: 324.1 $[M+H]^+$;

$^1$H NMR (600 MHz, $CDCl_3$) δ (ppm) 7.56 (t, J=7.7 Hz, 1H), 7.51 (dd, J=7.5, 1.8 Hz, 1H), 7.41 (d, J=7.6 Hz, 1H), 5.07 (dd, J=12.5, 5.2 Hz, 1H), 4.18-4.13 (m, 2H), 4.08-4.02 (m, 2H), 1.30 (t, J=7.1 Hz, 3H), 1.22 (t, J=7.1 Hz, 3H).

Step 2) Synthesis of diethyl ((6-bromopyridin-2-yl)fluoromethyl)phosphonate

Under 0° C., diethyl((6-bromopyridin-2-yl)(hydroxy)methyl)phosphonate (3.72 g, 11.5 mmol), pyridine hydrofluoride (1.2 mL) and dichloromethane (30 mL) were added into a 100 mL single-neck round bottom flask, and then diethylaminosulphur trifluoride (2.0 mL, 14.9 mmol) was added dropwise. The mixture was further stirred at 25° C. for 1 hour. After the mixture was stopped stirring, the reaction was quenched with saturated sodium bicarbonate aqueous solution (50 mL). The resulting mixture was separated. The organic layers were collected and dried over anhydrous sodium sulfate (2 g) and filtered. The filtrate was concentrated using a rotary evaporator under reduced pressure. The residue was purified by column chromatography (petroleum ether/ethyl acetate (v/v)=2/1) to get the title compound as light yellow oil (1.56 g, 41.7%).

MS (ESI, pos. ion) m/z: 326.1 $[M+H]^+$;

$^1$H NMR (600 MHz, $CDCl_3$) δ (ppm) 7.62 (t, J=7.8 Hz, 1H), 7.54 (dd, J=7.6, 1.3 Hz, 1H), 7.46 (d, J=7.9 Hz, 1H), 5.73 (dd, J=44.8, 9.1 Hz, 1H), 4.22 (q, J=7.2 Hz, 2H), 4.14-4.11 (m, 2H), 1.35-1.32 (m, 3H), 1.28 (t, J=7.1 Hz, 3H).

Step 3) Synthesis of tert-butyl 4-((6-bromopyridin-2-yl)fluoromethylene)piperidine-1-carboxylate Under 0° C., diethyl ((6-bromopyridin-2-yl)fluoromethyl) phosphonate (927 mg, 2.84 mmol), tert-butyl 4-oxopiperidine-1-carboxylate (0.8 g, 4.0 mmol) and tetrahydrofuran (10 mL) were added into a 100 mL single-neck round bottom flask, and then sodium hydride (160 mg, 4.0 mmol) was added. The mixture was stirred for 15 min, then the mixture was further stirred at 25° C. for 8 hours. After the mixture was stopped stirring, water (20 mL) was added, then the resulting mixture was extracted with dichloromethane (30 mL×2). The combined organic layers were dried over anhydrous sodium sulfate (2 g) and filtered. The filtrate was concentrated using a rotary evaporator under reduced pressure. The residue was purified by column chromatography (petroleum ether/ethyl acetate (v/v)=10/1) to get the title compound as a white solid (950 mg, 90%).

MS (ESI, pos. ion) m/z: 271.1 $[M+H-100]^+$;

$^1$H NMR (600 MHz, $CDCl_3$) δ (ppm) 7.60 (t, J=7.8 Hz, 1H), 7.47 (d, J=7.6 Hz, 1H), 7.40 (d, J=7.9 Hz, 1H), 3.53 (dd, J=13.1, 6.9 Hz, 4H), 2.98 (br, 2H), 2.56 (br, 2H), 1.51 (s, 9H).

Step 4) Synthesis of tert-butyl 4-(fluoro(6-(4-fluorobenzamide)pyridin-2-yl)methylene) piperidine-1-carboxylate The title compound of this step was prepared by referring to the method described in step 3 of example 1, i.e., tert-butyl 4-((6-bromopyridin-2-yl)fluoromethylene)piperidine-1-carboxylate (360 mg, 0.97 mmol), 4-fluorobenzamide (300 mg, 2.2 mmol), potassium carbonate (0.95 g, 6.8 mmol), cuprous iodide (410 mg, 2.2 mmol), (1R,2R)—$N^1$, $N^2$-dimethylcyclohexane-1,2-diamine (0.16 mL, 0.94 mmol), water (0.87 mL) were reacted in toluene (10 mL) to prepare it. The crude product was purified by silica gel column chromatography (petroleum ether/ethyl acetate (v/v) =5/1) to get the title compound as a white solid (330 mg, 79%).

MS (ESI, pos. ion) m/z: 430.2 $[M+H]^+$;

$^1$H NMR (400 MHz, $CDCl_3$) δ (ppm) 8.42 (s, 1H), 8.31 (d, J=8.3 Hz, 1H), 7.97 (dd, J=8.6, 5.2 Hz, 2H), 7.83 (t, J=8.0 Hz, 1H), 7.30 (s, 1H), 7.22 (t, J=8.5 Hz, 2H), 3.55 (t, J=5.7 Hz, 2H), 3.52-3.47 (m, 2H), 2.81 (t, J=5.3 Hz, 2H), 2.56 (br, 2H), 1.50 (s, 9H).

Step 5) Synthesis of 4-fluoro-N-(6-(fluoro(piperidin-4-ylidene)methyl)pyridin-2-yl)benzamide The title compound of this step was prepared by referring to the method described in step 4 of example 1, i.e., tert-butyl 4-(fluoro(6-(4-fluorobenzamide)pyridin-2-yl) methylene) piperidine-1-carboxylate (330 mg, 0.77 mmol) and hydrogen chloride ethyl acetate solution (2 M, 2 mL) was reacted in methanol (5 mL) to prepare it. The crude product was purified by silica gel column chromatography (dichloromethane/methanol (v/v)=20/1) to give the title compound as alight yellow solid (210 mg, 83%).

MS (ESI, pos. ion) m/z: 330.2 $[M+H]^+$;

$^1$H NMR (400 MHz, $CDCl_3$) δ (ppm) 8.49 (s, 1H), 8.30 (d, J=8.3 Hz, 1H), 7.97 (dd, J=8.7, 5.2 Hz, 2H), 7.82 (t, J=8.0 Hz, 1H), 7.27 (d, J=7.3 Hz, 1H), 7.21 (t, J=8.5 Hz, 2H), 3.01 (brs, 2H), 2.95 (brs, 2H), 2.77 (br, 2H), 2.55 (brs, 2H).

Step 6) Synthesis of 4-fluoro-N-(6-(fluoro(1-methylpiperidin-4-ylidene)methyl)pyridin-2-yl) benzamide The title compound of this step was prepared by referring to the method described in step 5 of example 1, i.e., 4-fluoro-N-(6-(fluoro(piperidin-4-ylidene)methyl)pyridin-2-yl) benzamide (205 mg, 0.62 mmol), sodium cyanoborohydride (120 mg, 1.9 mmol) and formaldehyde (40%, 0.46 mL, 6.2 mmol) were reacted in methanol (5 mL) to prepare it. The crude product was purified by silica gel column chromatography (dichloromethane/methanol (v/v)=20/1) to give the title compound as an off-white solid (150 mg, 70.2%).

MS (ESI, pos. ion) m/z: 344.2 $[M+H]^+$;

$^1$H NMR (400 MHz, $CDCl_3$) δ (ppm) 8.45 (s, 1H), 8.30 (d, J=8.3 Hz, 1H), 7.97 (dd, J=8.7, 5.2 Hz, 2H), 7.82 (t, J=8.0 Hz, 1H), 7.29 (s, 1H), 7.27 (s, 1H), 7.22 (t, J=8.5 Hz, 2H), 2.85 (t, J=5.3 Hz, 2H), 2.64 (t, J=4.6 Hz, 2H), 2.54 (t, J=5.6 Hz, 2H), 2.47 (t, J=5.3 Hz, 2H), 2.33 (s, 3H).

Example 9: Synthesis of 4-chloro-N-(6-(fluoro(1-methylpiperidin-4-ylidene)methyl)pyridine-2-yl) benzamide

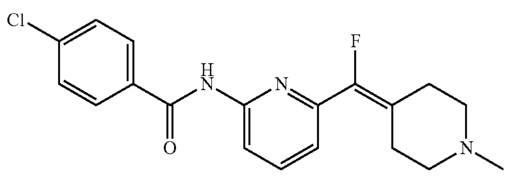 [SMILES: CN1CCC(=C(F)c2cccc(NC(=O)c3ccc(Cl)cc3)n2)CC1]

Step 1) Synthesis of tert-butyl 4-(fluoro(6-(4-chlorobenzamide)pyridin-2-yl)methylene) piperidine-1-carboxylate The title compound of this step was prepared by referring to the method described in step 3 of example 1, i.e., tert-butyl 4-((6-bromopyridin-2-yl)fluoromethylene)piperidine-1-carboxylate (360 mg, 0.97 mmol), 4-chlorobenzamide (300 mg, 1.9 mmol), potassium carbonate (0.95 g, 6.8 mmol), cuprous iodide (410 mg, 2.2 mmol), (1R,2R)—$N^1$, $N^2$-dimethylcyclohexane-1,2-diamine (0.16 mL, 0.94 mmol), water (0.87 mL) were reacted in toluene (10 mL) to prepare it. The crude product was purified by silica gel column chromatography (petroleum ether/ethyl acetate (v/v) =5/1) to get the title compound as a white solid (220 mg, 51%).

MS (ESI, pos. ion) m/z: 446.2 $[M+H]^+$;

$^1$H NMR (400 MHz, $CDCl_3$) δ (ppm) 8.44 (s, 1H), 8.32 (d, J=8.3 Hz, 1H), 7.89 (d, J=8.5 Hz, 2H), 7.84 (t, J=8.0 Hz, 1H), 7.52 (d, J=8.5 Hz, 2H), 7.29 (d, J=8.4 Hz, 1H), 3.55 (t, J=5.7 Hz, 2H), 3.50 (t, J=5.3 Hz, 2H), 2.81 (t, J=5.3 Hz, 2H), 2.57 (brs, 2H), 1.51 (s, 9H).

Step 2) Synthesis of 4-chloro-N-(6-(fluoro(piperidin-4-ylidene)methyl)pyridin-2-yl)benzamide The title compound of this step was prepared by referring to the method described in step 4 of example 1, i.e., tert-butyl 4-(fluoro(6-(4-chlorobenzamide)pyridin-2-yl) methylene) piperidine-1-carboxylate (200 mg, 0.45 mmol) and hydrogen chloride ethyl acetate solution (2 M, 2 mL) was reacted in methanol (5 mL) to prepare it. The crude product was purified by silica gel column chromatography (dichloromethane/methanol (v/v)=20/1) to give the title compound as alight yellow solid (140 mg, 90%).

MS (ESI, pos. ion) m/z: 346.1 $[M+H]^+$;

$^1$H NMR (400 MHz, $CDCl_3$) δ (ppm) 8.49 (s, 1H), 8.30 (d, J=8.3 Hz, 1H), 7.89 (d, J=8.5 Hz, 2H), 7.83 (t, J=8.0 Hz, 1H), 7.51 (d, J=8.5 Hz, 2H), 7.28 (s, 1H), 3.02 (brs, 2H), 2.97 (brs, 2H), 2.76 (brs, 2H), 2.55 (brs, 2H).

Step 3) Synthesis of 4-chloro-N-(6-(fluoro(1-methylpiperidin-4-ylidene)methyl)pyridin-2-yl) benzamide The title compound of this step was prepared by referring to the method described in step 5 of example 1, i.e., 4-chloro-N-(6-(fluoro(piperidin-4-ylidene)methyl)pyridin-2-yl) benzamide (150 mg, 0.43 mmol), sodium cyanoborohydride (90 mg, 1.43 mmol) and formaldehyde (40%, 0.32 mL, 4.3 mmol) were reacted in methanol (5 mL) to prepare it. The crude product was purified by silica gel column chromatography (dichloromethane/methanol (v/v)=20/1) to give the title compound as a light yellow solid (106 mg, 67.9%).

MS (ESI, pos. ion) m/z: 360.1 $[M+H]^+$;

$^1$H NMR (400 MHz, $CDCl_3$) δ (ppm) 8.49 (s, 1H), 8.31 (d, J=8.3 Hz, 1H), 7.89 (d, J=8.4 Hz, 2H), 7.83 (t, J=8.0 Hz, 1H), 7.51 (d, J=8.4 Hz, 2H), 7.29 (d, J=3.8 Hz, 1H), 2.85 (t, J=5.2 Hz, 2H), 2.64 (d, J=4.6 Hz, 2H), 2.57-2.52 (m, 2H), 2.48 (t, J=5.1 Hz, 2H), 2.34 (s, 3H).

Example 10: Synthesis of 2,4-difluoro-N-(6-(fluoro (1-methylpiperidin-4-ylidene)methyl) pyridine-2-yl) benzamide

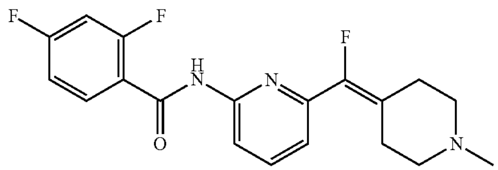 [SMILES: CN1CCC(=C(F)c2cccc(NC(=O)c3ccc(F)cc3F)n2)CC1]

Step 1) Synthesis of tert-butyl 4-(fluoro(6-(2,4-difluorobenzamide)pyridin-2-yl)methylene) piperidine-1-carboxylate The title compound of this step was prepared by referring to the method described in step 3 of example 1, i.e., tert-butyl 4-((6-bromopyridin-2-yl)fluoromethylene)piperidine-1-carboxylate (1.0 g, 2.69 mmol), 2,4-difluorobenzamide (700 mg, 4.46 mmol), potassium carbonate (2.6 g, 18.8 mmol), cuprous iodide (400 mg, 2.1 mmol), (1R,2R)—$N^1$,$N^2$-dimethylcyclohexane-1,2-diamine (0.3 mL, 1.76 mmol), water (2.5 mL) were reacted in toluene (10 mL) to prepare it. The crude product was purified by silica gel column chromatography (petroleum ether/ethyl acetate (v/v)= 10/1) to get the title compound as a white solid (802 mg, 66%).

MS (ESI, pos. ion) m/z: 448.2 $[M+H]^+$;

$^1$H NMR (400 MHz, $CDCl_3$) δ (ppm) 8.89 (d, J=14.4 Hz, 1H), 8.27 (d, J=8.3 Hz, 1H), 8.20 (dd, J=15.5, 9.0 Hz, 1H), 7.81 (t, J=8.0 Hz, 1H), 7.30 (d, J=7.4 Hz, 1H), 7.26 (s, 1H), 7.11-7.02 (m, 1H), 7.00-6.93 (m, 1H), 3.54-3.49 (m, 4H), 2.88 (d, J=5.4 Hz, 2H), 2.54 (brs, 2H), 1.57 (s, 9H).

Step 2) Synthesis of 2,4-difluoro-N-(6-(fluoro(piperidin-4-ylidene)methyl)pyridin-2-yl) benzamide The title compound of this step was prepared by referring to the method described in step 4 of example 1, i.e., tert-butyl 4-(fluoro(6-(2,4-difluorobenzamide)pyridin-2-yl) methylene) piperidine-1-carboxylate (800 mg, 1.79 mmol) and hydrogen chloride ethyl acetate solution (2 M, 2 mL) were reacted in methanol (10 mL) to prepare it. The crude product was purified by silica gel column chromatography (dichloromethane/methanol (v/v)=20/1) to give the title compound as alight yellow solid (310 mg, 49.9%).

MS (ESI, pos. ion) m/z: 348.1 $[M+H]^+$;

$^1$H NMR (400 MHz, $CDCl_3$) δ (ppm) 8.91 (d, J=0.8 Hz, 1H), 8.31-8.24 (m, 1H), 8.23-8.15 (m, 1H), 7.85-7.76 (m, 1H), 7.31 (d, J=8.0 Hz, 1H), 7.07 (t, J=8.3 Hz, 1H), 7.01-6.91 (m, 1H), 3.05-2.97 (m, 4H), 2.90 (br, 2H), 2.59 (br, 2H).

Step 3) Synthesis of 2,4-difluoro-N-(6-(fluoro(1-methylpiperidin-4-ylidene)methyl)pyridin-2-yl) benzamide The title compound of this step was prepared by referring to the method described in step 5 of example 1, i.e., 2,4-difluoro-N-(6-(fluoro(piperidin-4-ylidene)methyl)pyridin-2-yl) benzamide (300 mg, 0.86 mmol), sodium cyanoborohydride (200 mg, 3.17 mmol) and formaldehyde (40%, 0.64 mL, 8.6 mmol) were reacted in methanol (5 mL) to prepare it. The crude product was purified by silica gel column chromatography (dichloromethane/methanol (v/v)= 20/1) to give the title compound as a light yellow solid (240 mg, 76.9%).

MS (ESI, pos. ion) m/z: 362.1 $[M+H]^+$;

$^1$H NMR (400 MHz, $CDCl_3$) δ (ppm) 8.89 (d, J=13.2 Hz, 1H), 8.26 (d, J=8.3 Hz, 1H), 8.19 (dd, J=15.5, 8.9 Hz, 1H), 7.79 (t, J=8.0 Hz, 1H), 7.29 (d, J=7.8 Hz, 1H), 7.10-7.03 (m, 1H), 7.00-6.91 (m, 1H), 2.92 (t, J=5.3 Hz, 2H), 2.65-2.58 (m, 2H), 2.55-2.50 (m, 2H), 2.48 (t, J=5.2 Hz, 2H), 2.32 (s, 3H).

Example 11: Synthesis of 4-chloro-2-fluoro-N-(6-(fluoro(1-methylpiperidin-4-ylidene) methyl)pyridin-2-yl)benzamide

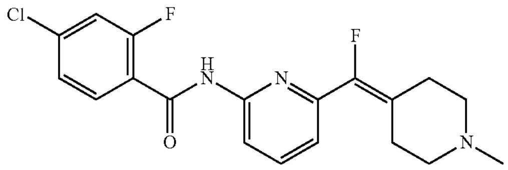 [SMILES: CN1CCC(=C(F)c2cccc(NC(=O)c3ccc(Cl)cc3F)n2)CC1]

Step 1) Synthesis of tert-butyl 4-(fluoro(6-(4-chloro-2-fluorobenzamide)pyridin-2-yl)methylene) piperidine-1-carboxylate The title compound of this step was prepared by referring to the method described in step 3 of example 1, i.e., tert-butyl 4-((6-bromopyridin-2-yl)fluoromethylene)piperidine-1-carboxylate (0.6 g, 1.62 mmol), 4-chloro-2-fluorobenzamide (400 mg, 2.3 mmol), potassium carbonate (2.0 g, 14.5 mmol), cuprous iodide (200 mg, 1.05 mmol), (1R, 2R)—$N^1$,$N^2$-dimethylcyclohexane-1,2-diamine (0.2 mL, 1.17 mmol), water (1.0 mL) were reacted in toluene (10 mL) to prepare it. The crude product was purified by silica gel column chromatography (petroleum ether/ethyl acetate (v/v)= 10/1) to get the title compound as a white solid (543 mg, 72.2%).

MS (ESI, pos. ion) m/z: 464.2 $[M+H]^+$;

$^1$H NMR (400 MHz, $CDCl_3$) δ (ppm) 8.90 (d, J=13.7 Hz, 1H), 8.27 (d, J=8.3 Hz, 1H), 8.11 (t, J=8.5 Hz, 1H), 7.81 (t, J=8.0 Hz, 1H), 7.36-7.29 (m, 2H), 7.30-7.27 (m, 1H), 3.56-3.46 (m, 4H), 2.87 (t, J=5.3 Hz, 2H), 2.54 (s, 2H), 1.49 (s, 9H).

Step 2) Synthesis of 4-chloro-2-fluoro-N-(6-(fluoro (piperidine-4-ylidene)methyl)pyridin-2-yl) benzamide The title compound of this step was prepared by referring to the method described in step 4 of example 1, i.e., tert-butyl 4-(fluoro(6-(4-chloro-2-fluorobenzamide)pyridin- 2-yl) methylene)piperidine-1-carboxylate (520 mg, 1.12 mmol) and hydrogen chloride ethyl acetate solution (2 M, 2 mL) was reacted in methanol (10 mL) to prepare it. The crude product was purified by silica gel column chromatography (dichloromethane/methanol (v/v)=20/1) to give the title compound as a white slime-like substance (340 mg, 83.3%).

MS (ESI, pos. ion) m/z: 364.1 $[M+H]^+$;

$^1$H NMR (400 MHz, $CDCl_3$) δ (ppm) 8.92 (d, J=13.4 Hz, 1H), 8.29 (dd, J=8.3, 3.7 Hz, 1H), 8.13 (td, J=8.5, 2.5 Hz, 1H), 7.83 (td, J=8.0, 3.0 Hz, 1H), 7.37-7.33 (m, 1H), 7.33-7.25 (m, 2H), 3.57-3.51 (m, 2H), 3.01 (br, 2H), 2.89 (brs, 2H), 2.56 (brs, 2H).

Step 3) Synthesis of 4-chloro-2-fluoro-N-(6-(fluoro (1-methylpiperidin-4-ylidene)methyl) pyridin-2-yl) benzamide The title compound of this step was prepared by referring to the method described in step 5 of example 1, i.e., 4-chloro-2-fluoro-N-(6-(fluoro(piperidin-4-ylidene)methyl) pyridin-2-yl) benzamide (310 mg, 0.85 mmol), sodium cyanoborohydride (200 mg, 3.17 mmol) and formaldehyde (40%, 0.64 mL, 8.6 mmol) were reacted in methanol (5 mL) to prepare it. The crude product was purified by silica gel column chromatography (dichloromethane/methanol (v/v)=20/1) to give the title compound as a light yellow solid (272 mg, 84.5%).

MS (ESI, pos. ion) m/z: 378.1 $[M+H]^+$;

$^1$H NMR (400 MHz, $CDCl_3$) δ (ppm) 8.92 (d, J=13.3 Hz, 1H), 8.28 (d, J=8.3 Hz, 1H), 8.13 (t, J=8.5 Hz, 1H), 7.82 (t, J=8.0 Hz, 1H), 7.35 (d, J=8.6 Hz, 1H), 7.31 (d, J=7.7 Hz, 1H), 7.27 (d, J=10.2 Hz, 1H), 2.94 (t, J=5.5 Hz, 2H), 2.66-2.60 (m, 2H), 2.57-2.51 (m, 2H), 2.49 (t, J=5.4 Hz, 2H), 2.34 (s, 3H).

Example 12: Synthesis of 2,4,6-trifluoro-N-(6-(fluoro(1-methylpiperidin-4-ylidene)methyl) pyridine-2-yl)benzamide

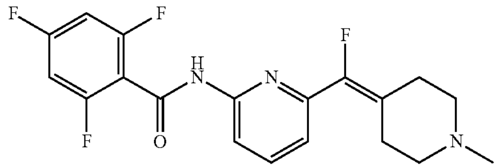 [SMILES: CN1CCC(=C(F)c2cccc(NC(=O)c3c(F)cc(F)cc3F)n2)CC1]

Step 1) Synthesis of tert-butyl 4-(fluoro(6-(2,4,6-trifluorobenzamide)pyridin-2-yl)methylene) piperidine-1-carboxylate The title compound of this step was prepared by referring to the method described in step 3 of example 1, i.e., tert-butyl 4-((6-bromopyridin-2-yl)fluoromethylene)piperidine-1-carboxylate (0.6 g, 1.62 mmol), 2,4,6-trifluorobenzamide (400 mg, 2.28 mmol), potassium carbonate (2.0 g, 14.5 mmol), cuprous iodide (200 mg, 1.05 mmol), (1R, 2R)—$N^1$,$N^2$-dimethylcyclohexane-1,2-diamine (0.2 mL, 1.17 mmol), water (1.0 mL) were reacted in toluene (10 mL) to prepare it. The crude product was purified by silica gel column chromatography (petroleum ether/ethyl acetate (v/v)= 10/1) to get the title compound as a white solid (330 mg, 43.7%).

MS (ESI, pos. ion) m/z: 466.2 $[M+H]^+$;

$^1$H NMR (400 MHz, $CDCl_3$) δ (ppm) 8.27 (d, J=8.2 Hz, 1H), 7.82 (t, J=8.0 Hz, 1H), 7.30 (d, J=7.7 Hz, 1H), 7.26 (s, 1H), 6.78 (t, J=8.2 Hz, 2H), 3.55-3.48 (m, 2H), 3.45 (t, J=5.4 Hz, 2H), 2.81 (t, J=5.3 Hz, 2H), 2.52 (br, 2H), 1.47 (s, 9H).

Step 2) Synthesis of 2,4,6-trifluoro-N-(6-(fluoro (piperidin-4-ylidene)methyl)pyridin-2-yl) benzamide The title compound of this step was prepared by referring to the method described in step 4 of example 1, i.e., tert-butyl 4-(fluoro(6-(2,4,6-trifluorobenzamide)pyridin-2-yl)methylene) piperidine-1-carboxylate (330 mg, 0.71 mmol) and hydrogen chloride ethyl acetate solution (2 M, 2 mL) were reacted in methanol (5 mL) to prepare it. The crude product was purified by silica gel column chromatography (dichloromethane/methanol (v/v)=20/1) to give the title compound as a light yellow solid (151 mg, 57.9%).

MS (ESI, pos. ion) m/z: 366.1 $[M+H]^+$;

$^1$H NMR (600 MHz, $CDCl_3$) δ (ppm) 8.52 (s, 1H), 8.26 (d, J=8.2 Hz, 1H), 7.81 (t, J=8.0 Hz, 1H), 7.28 (d, J=7.7 Hz, 1H), 6.76 (t, J=8.2 Hz, 2H), 2.98 (br, 2H), 2.91 (br, 2H), 2.79 (br, 2H), 2.52 (br, 2H).

Step 3) Synthesis of 2,4,6-trifluoro-N-(6-(fluoro(1-methylpiperidin-4-ylidene)methyl) pyridin-2-yl) benzamide The title compound of this step was prepared by referring to the method described in step 5 of example 1, i.e., 2,4,6-trifluoro-N-(6-(fluoro(piperidin-4-ylidene)methyl) pyridin-2-yl) benzamide (150 mg, 0.41 mmol), sodium cyanoborohydride (100 mg, 1.58 mmol) and formaldehyde (40%, 0.32 mL, 4.3 mmol) were reacted in methanol (5 mL) to prepare it. The crude product was purified by silica gel column chromatography (dichloromethane/methanol (v/v)=20/1) to give the title compound as a light yellow solid (101 mg, 64.2%).

MS (ESI, pos. ion) m/z: 380.2 $[M+H]^+$;

$^1$H NMR (400 MHz, $CDCl_3$) δ (ppm) 8.66 (s, 1H), 8.27 (d, J=8.2 Hz, 1H), 7.81 (t, J=8.0 Hz, 1H), 7.28 (d, J=6.4 Hz, 1H), 6.73 (t, J=8.3 Hz, 2H), 2.84 (t, J=5.1 Hz, 2H), 2.59 (br, 2H), 2.54-2.49 (m, 2H), 2.42 (t, J=5.2 Hz, 2H), 2.30 (s, 3H).

Example 13: Synthesis of 5-fluoro-N-(6-(fluoro(1-methylpiperidin-4-ylidene)methyl)pyridin-2-yl)picolinamide

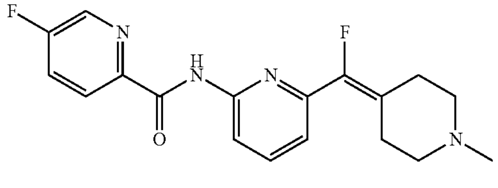 [SMILES: CN1CCC(=C(F)c2cccc(NC(=O)c3ccc(F)cn3)n2)CC1]

Step 1) Synthesis of tert-butyl 4-(fluoro(6-(5-fluoropicolinamide)pyridin-2-yl)methylene) piperidine-1-carboxylate The title compound of this step was prepared by referring to the method described in step 3 of example 1, i.e., tert-butyl 4-((6-bromopyridin-2-yl)fluoromethylene)piperidine-1-carboxylate (0.31 g, 0.84 mmol), 5-fluoropyridine- 2-formamide (250 mg, 1.80 mmol), potassium carbonate (0.82 g, 5.9 mmol), cuprous iodide (350 mg, 1.8 mmol), (1R,2R)—$N^1$,$N^2$-dimethylcyclohexane-1,2-diamine (0.14 mL, 0.82 mmol), water (1.0 mL) were reacted in toluene (10 mL) to prepare it. The crude product was purified by silica gel column chromatography (petroleum ether/ethyl acetate (v/v)=10/1) to get the title compound as light yellow oil (0.26 g, 72%).

MS (ESI, pos. ion) m/z: 431.2 $[M+H]^+$;

$^1H$ NMR (400 MHz, $CDCl_3$) δ (ppm) 10.26 (s, 1H), 8.53 (d, J=2.6 Hz, 1H), 8.39-8.34 (m, 2H), 7.83 (t, J=8.0 Hz, 1H), 7.63 (td, J=8.3, 2.7 Hz, 1H), 7.31 (d, J=7.6 Hz, 1H), 3.58-3.50 (m, 4H), 2.93 (t, J=5.3 Hz, 2H), 2.60-2.55 (m, 2H), 1.51 (s, 9H).

Step 2) Synthesis of 5-fluoro-N-(6-(fluoro(piperidin-4-ylidene)methyl)pyridin-2-yl)picolinamide The title compound of this step was prepared by referring to the method described in step 4 of example 1, i.e., tert-butyl 4-(fluoro(6-(5-fluoropicolinamide)pyridin-2-yl) methylene) piperidine-1-carboxylate (250 mg, 0.58 mmol) and hydrogen chloride ethyl acetate solution (2 M, 2 mL) were reacted in methanol (5 mL) to prepare it. The crude product was purified by silica gel column chromatography (dichloromethane/methanol (v/v)=20/1) to give the title compound as a light yellow solid (0.12 g, 62.5%).

MS (ESI, pos. ion) m/z: 331.2 $[M+H]^+$;

$^1H$ NMR (400 MHz, $CDCl_3$) δ (ppm) 10.24 (s, 1H), 8.52 (d, J=2.3 Hz, 1H), 8.35 (dd, J=11.0, 6.1 Hz, 2H), 7.82 (t, J=7.9 Hz, 1H), 7.66-7.59 (m, 1H), 7.30 (s, 1H), 3.06 (br, 6H), 2.80 (s, 1H), 2.65 (brs, 2H).

Step 3) Synthesis of 5-fluoro-N-(6-(fluoro(1-methylpiperidin-4-ylidene)methyl)pyridin-2-yl) picolinamide The title compound of this step was prepared by referring to the method described in step 5 of example 1, i.e., 5-fluoro-N-(6-(fluoro(piperidin-4-ylidene)methyl)pyridin-2-yl) picolinamide (0.22 g, 0.67 mmol), sodium cyanoborohydride (130 mg, 2.0 mmol) and formaldehyde (40%, 0.49 mL, 6.6 mmol) were reacted in methanol (5 mL) to prepare it. The crude product was purified by silica gel column chromatography (dichloromethane/methanol (v/v)=50/1) to give the title compound as an off-white solid (0.12 g, 52.3%).

MS (ESI, pos. ion) m/z: 345.1 $[M+H]^+$;

$^1H$ NMR (400 MHz, $CDCl_3$) δ (ppm) 10.28 (d, J=11.6 Hz, 1H), 8.52 (d, J=2.6 Hz, 1H), 8.40-8.32 (m, 2H), 7.82 (t, J=8.0 Hz, 1H), 7.63 (td, J=8.3, 2.7 Hz, 1H), 7.31 (s, 1H), 2.97 (t, J=5.3 Hz, 2H), 2.64 (d, J=4.7 Hz, 2H), 2.60-2.46 (m, 4H), 2.35 (s, 3H).

Example 14: Synthesis of 5-chloro-N-(6-(fluoro(1-methylpiperidin-4-ylidene)methyl) pyridin-2-yl) picolinamide

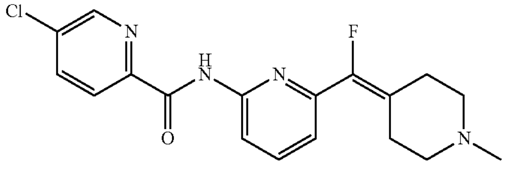 [SMILES: CN1CCC(=C(F)c2cccc(NC(=O)c3ccc(Cl)cn3)n2)CC1]

Step 1) Synthesis of tert-butyl 4-((6-(5-chloropicolinamide)pyridin-2-yl)fluoromethylene) piperidine-1-carboxylate The title compound of this step was prepared by referring to the method described in step 3 of example 1, i.e., tert-butyl 4-((6-bromopyridin-2-yl)fluoromethylene)piperidine-1-carboxylate (0.33 g, 0.89 mmol), 5-chloropyridine-2-formamide (280 mg, 2.2 mmol), potassium carbonate (0.87 g, 6.2 mmol), cuprous iodide (500 mg, 2.6 mmol), (1R,2R)—$N^1$,$N^2$-dimethylcyclohexane-1,2-diamine (0.15 mL, 0.88 mmol), water (1.0 mL) were reacted in toluene (10 mL) to prepare it. The crude product was purified by silica gel column chromatography (petroleum ether/ethyl acetate (v/v)=10/1) to get the title compound as a white solid (0.29 g, 73%).

MS (ESI, pos. ion) m/z: 447.1 $[M+H]^+$;

$^1H$ NMR (400 MHz, $CDCl_3$) δ (ppm) 10.27 (s, 1H), 8.64 (d, J=1.8 Hz, 1H), 8.36 (d, J=8.3 Hz, 1H), 8.28 (d, J=8.4 Hz, 1H), 7.92 (dd, J=8.4, 2.2 Hz, 1H), 7.84 (t, J=8.0 Hz, 1H), 7.31 (d, J=7.7 Hz, 1H), 3.58-3.52 (m, 4H), 2.93 (t, J=5.4 Hz, 2H), 2.58 (brs, 2H), 1.52 (s, 9H).

Step 2) Synthesis of 5-chloro-N-(6-(fluoro(piperidin-4-ylidene)methyl)pyridin-2-yl)picolinamide The title compound of this step was prepared by referring to the method described in step 4 of example 1, i.e., tert-butyl 4-((6-(5-chloropicolinamide)pyridin-2-yl)fluoromethylene) piperidine-1-carboxylate (100 mg, 0.22 mmol) and hydrogen chloride ethyl acetate solution (2 M, 2 mL) were reacted in methanol (5 mL) to prepare it. The crude product was purified by silica gel column chromatography (dichloromethane/methanol (v/v)=20/1) to give the title compound as a light yellow solid (0.07 g, 90.2%).

MS (ESI, pos. ion) m/z: 347.2 $[M+H]^+$;

$^1H$ NMR (400 MHz, $CDCl_3$) δ (ppm) 10.28 (s, 1H), 8.63 (d, J=1.9 Hz, 1H), 8.35 (d, J=8.3 Hz, 1H), 8.28 (d, J=8.3 Hz, 1H), 7.91 (dd, J=8.4, 2.3 Hz, 1H), 7.83 (t, J=8.0 Hz, 1H), 7.31 (s, 1H), 3.05-2.93 (m, 4H), 2.87 (s, 2H), 2.56 (s, 2H).

Step 3) Synthesis of 5-chloro-N-(6-(fluoro(1-methylpiperidin-4-ylidene)methyl)pyridin-2-yl) picolinamide The title compound of this step was prepared by referring to the method described in step 5 of example 1, i.e., 5-chloro-N-(6-(fluoro(piperidin-4-ylidene)methyl)pyridin-2-yl) picolinamide (0.2 g, 0.58 mmol), sodium cyanoborohydride (110 mg, 1.7 mmol) and formaldehyde (40%, 0.43 mL, 5.8 mmol) were reacted in methanol (5 mL) to prepare it. The crude product was purified by silica gel column chromatography (dichloromethane/methanol (v/v)=50/1) to give the title compound as an off-white solid (0.17 g, 80.7%).

MS (ESI, pos. ion) m/z: 361.2 $[M+H]^+$;

$^1H$ NMR (400 MHz, $CDCl_3$) δ (ppm) 10.27 (s, 1H), 8.63 (d, J=2.0 Hz, 1H), 8.34 (d, J=8.3 Hz, 1H), 8.27 (d, J=8.4 Hz, 1H), 7.91 (dd, J=8.4, 2.2 Hz, 1H), 7.82 (t, J=8.0 Hz, 1H), 7.29 (d, J=7.5 Hz, 1H), 2.96 (t, J=5.2 Hz, 2H), 2.64 (t, J=4.6 Hz, 2H), 2.57-2.48 (m, 4H), 2.34 (s, 3H).

Example 15: Synthesis of 2,4,6-trifluoro-N-(6-((1-ethylpiperidin-4-ylidene)methyl) pyridin-2-yl)benzamide

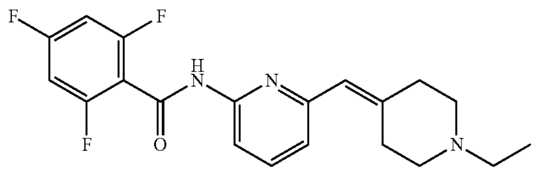 [SMILES: CCN1CCC(=Cc2cccc(NC(=O)c3c(F)cc(F)cc3F)n2)CC1]

Step 1) Synthesis of 2-bromo-6-(piperidin-4-ylidenemethyl)pyridine

The title compound of this step was prepared by referring to the method described in step 4 of example 1, i.e., tert-butyl 4-((6-bromopyridin-2-yl)methylene)piperidine-1-carboxylate (5.0 g, 14.16 mmol) and hydrogen chloride ethyl acetate solution (2 M, 20 mL) were reacted in methanol (20 mL) to prepare it. The crude product was purified by silica gel column chromatography (dichloromethane/methanol (v/v)=20/1) to give the title compound as a light yellow solid (3.5 g, 98%).

MS (ESI, pos. ion) m/z: 253.2 $[M+H]^+$;

$^1$H NMR (400 MHz, DMSO-$d_6$) δ (ppm) 7.68 (t, J=7.6 Hz, 1H), 7.41 (d, J=7.6 Hz, 1H), 7.28 (d, J=7.6 Hz, 1H), 6.25 (s, 1H), 2.91-2.86 (m, 2H), 2.83 (brs, 4H), 2.30 (t, J=5.6 Hz, 2H).

Step 2) Synthesis of 2-bromo-6-((1-ethylpiperidin-4-ylidene)methyl)pyridine

Under 25° C., 2-bromo-6-(piperidin-4-ylidenemethyl) pyridine (800 mg, 3.2 mmol), N,N-diisopropylethylamine (1.0 mL, 6.05 mmol) and acetonitrile (10 mL) were added into a 100 mL single-neck round bottom flask, and then iodoethane (0.38 mL, 4.75 mmol) was added. The mixture was stirred for 16 hours. After the mixture was stopped stirring, water (20 mL) was added, and the resulting mixture was extracted with dichloromethane (30 mL×2). The combined organic layers were dried over anhydrous sodium sulfate (2 g) and filtered. The filtrate was concentrated using a rotary evaporator under reduced pressure. The residue was purified by column chromatography (dichloromethane/methanol (v/v)=20/1) to get the title compound as light yellow oil (0.87 g, 96.7%).

MS (ESI, pos. ion) m/z: 281.1 $[M+H]^+$;

$^1$H NMR (400 MHz, $CDCl_3$) δ (ppm) 7.49 (t, J=7.6 Hz, 1H), 7.28 (d, J=7.6 Hz, 1H), 7.07 (d, J=7.6 Hz, 1H), 6.30 (s, 1H), 3.46 (brs, 2H), 3.23-3.16 (m, 4H), 3.07 (q, J=7.2 Hz, 2H), 2.85 (t, J=5.2 Hz, 2H), 1.46 (t, J=7.2 Hz, 3H).

Step 3) Synthesis of 2,4,6-trifluoro-N-(6-((1-ethylpiperidin-4-ylidene)methyl)pyridin-2-yl) benzamide The title compound of this step was prepared by referring to the method described in step 3 of example 1, i.e., 2-bromo-6-((1-ethylpiperidin-4-ylidene)methyl)pyridine (0.2 g, 1.1 mmol), 2,4,6-trifluoro-benzamide (351 mg, 2.0 mmol), potassium carbonate (1.1 g, 7.98 mmol), cuprous iodide (220 mg, 1.2 mmol), (1R,2R)—$N^1$,$N^2$-dimethylcyclohexane-1,2-diamine (0.2 mL, 1.17 mmol), water (1.0 mL) were reacted in toluene (10 mL) to prepare it. The crude product was purified by silica gel column chromatography (dichloromethane/methano (v/v)=20/1) to get the title compound as alight yellow solid (220 mg, 51.3%).

MS (ESI, pos. ion) m/z: 376.2 $[M+H]^+$;

$^1$H NMR (400 MHz, DMSO-$d_6$) δ (ppm) 11.14 (s, 1H), 7.96 (d, J=8.0 Hz, 1H), 7.83 (t, J=8.0 Hz, 1H), 7.37 (t, J=8.4 Hz, 2H), 7.09 (d, J=7.6 Hz, 1H), 6.38 (s, 1H), 3.41 (brs, 2H), 3.22-3.13 (m, 4H), 3.08-3.01 (m, 2H), 2.87-2.82 (m, 2H), 1.19 (t, J=7.2 Hz, 3H).

Example 16: Synthesis of N-(6-((1-cyclopropylpiperidin-4-ylidene)methyl)pyridin-2-yl)-2,4,6-trifluorobenzamide

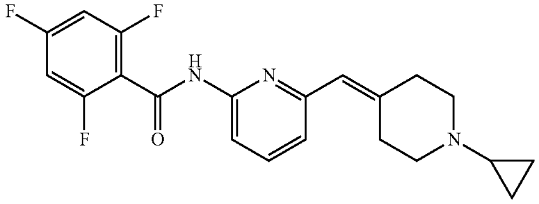 [SMILES: O=C(Nc1cccc(C=C2CCN(C3CC3)CC2)n1)c1c(F)cc(F)cc1F]

Step 1) Synthesis of 2-bromo-6-((1-cyclopropylpiperidin-4-ylidene)methyl)pyridine The title compound of this step was prepared by referring to the method described in step 5 of example 1, i.e., 2-bromo-6-(piperidin-4-ylidenemethyl)pyridine (800 mg, 3.2 mmol), sodium cyanoborohydride (600 mg, 9.48 mmol), 1-ethoxy-1-trimethylsiloxycyclopropane (1.0 mL, 5.0 mmol) and acetic acid (0.1 mL) were reacted in methanol (5 mL) to prepare it. The crude product was purified by silica gel column chromatography (dichloromethane/methanol (v/v)=100/1) to give the title compound as a light yellow solid (110 mg, 11.9%).

MS (ESI, pos. ion) m/z: 293.1 $[M+H]^+$;

Step 2) Synthesis of N-(6-((1-cyclopropylpiperidin-4ylidene)methyl)pyridin-2-yl)-2,4,6-trifluorobenzamide The title compound of this step was prepared by referring to the method described in step 3 of example 1, i.e., 2-bromo-6-((1-cyclopropylpiperidin-4-ylidene)methyl)pyridine (0.41 g, 1.4 mmol), 2,4,6-trifluoro-benzamide (200 mg, 1.1 mmol), potassium carbonate (1.1 g, 7.98 mmol), cuprous iodide (220 mg, 1.2 mmol), (1R,2R)—$N^1$,$N^2$-dimethylcyclohexane-1,2-diamine (0.2 mL, 1.17 mmol), water (1.0 mL) were reacted in toluene (10 mL) to prepare it. The crude product was purified by silica gel column chromatography (dichloromethane/methano (v/v)=20/1) to get the title compound as a light yellow solid (139 mg, 31.4%).

MS (ESI, pos. ion) m/z: 388.1 $[M+H]^+$;

$^1$H NMR (400 MHz, $CDCl_3$) δ (ppm) 8.94 (s, 1H), 8.16 (d, J=8.0 Hz, 1H), 7.70 (t, J=8.0 Hz, 1H), 6.92 (d, J=7.6 Hz, 1H), 6.69 (t, J=8.0 Hz, 2H), 6.06 (s, 1H), 2.75 (t, J=5.6 Hz, 2H), 2.71 (t, J=5.6 Hz, 2H), 2.57 (t, J=5.6 Hz, 2H), 2.35 (t, J=5.6 Hz, 2H), 1.61-1.53 (m, 1H), 0.43 (m, 4H).

Example 17: Synthesis of N-(6-((1-(2,2-difluoroethyl)piperidin-4-ylidene)methyl)pyridin-2-yl)-2,4,6-trifluorobenzamide

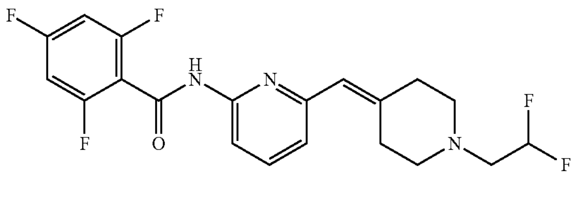 [SMILES: O=C(Nc1cccc(C=C2CCN(CC(F)F)CC2)n1)c1c(F)cc(F)cc1F]

Step 1) Synthesis of 2-bromo-6-((1-(2,2-difluoroethyl)piperidin-4-ylidene)methyl)pyridine 2-Bromo-6-(piperidin-4-ylidenemethyl)pyridine (600 mg, 2.4 mmol), 2,2-difluoroethyl 4-methylbenzenesulfonate (900 mg, 3.8 mmol), sodium iodide (400 mg, 2.7 mmol), potassium carbonate (370 mg, 2.7 mmol) and N,N-dimethylformamide (10 mL) were added into a 100 mL single-neck round bottom flask. The mixture was stirred at 70° C. in an oil bath for 24 hours. After the mixture was stopped stirring, water (40 mL) was added, and the resulting mixture was extracted with dichloromethane (30 mL×2). The combined organic layers were dried over anhydrous sodium sulfate (2 g) and filtered. The filtrate was concentrated using a rotary evaporator under reduced pressure. The residue was purified by column chromatography (dichloromethane/methanol (v/v)=100/1) to get the title compound as light yellow oil (0.74 g, 98.4%).

MS (ESI, pos. ion) m/z: 317.0 $[M+H]^+$;

Step 2) Synthesis of N-(6-((1-(2,2-difluoroethyl)piperidin-4-ylidene)methyl)pyridin-2-yl)-2,4,6-trifluorobenzamide The title compound of this step was prepared by referring to the method described in step 3 of example 1, i.e., 2-bromo-6-((1-(2,2-difluoroethyl)piperidin-4-ylidene)methyl)pyridine (0.74 g, 2.3 mmol), 2,4,6-trifluoro-benzamide (200 mg, 1.1 mmol), potassium carbonate (1.1 g, 7.98 mmol), cuprous iodide (220 mg, 1.2 mmol), (1R,2R)—$N^1$, $N^2$-dimethylcyclohexane-1,2-diamine (0.2 mL, 1.17 mmol), water (1.0 mL) were reacted in toluene (10 mL) to prepare it. The crude product was purified by silica gel column chromatography (dichloromethane/methano (v/v)=50/1) to get the title compound as a light yellow solid (103 mg, 21.9%).

MS (ESI, pos. ion) m/z: 412.1 $[M+H]^+$;

$^1H$ NMR (400 MHz, $CDCl_3$) δ (ppm) 8.61 (s, 1H), 8.15 (d, J=8.0 Hz, 1H), 7.70 (t, J=8.0 Hz, 1H), 6.93 (d, J=7.6 Hz, 1H), 6.73 (t, J=8.4 Hz, 2H), 6.13 (s, 1H), 5.88 (tt, J=56.0, 4.4 Hz, 1H), 2.83 (t, J=5.6 Hz, 2H), 2.76 (dd, J=15.2, 4.4 Hz, 2H), 2.69 (dd, J=8.8, 4.8 Hz, 2H), 2.57 (t, J=5.6 Hz, 2H), 2.40 (t, J=5.6 Hz, 2H).

Example 18: Synthesis of N-(6-((1-(2,2,2-trifluoroethyl)piperidin-4-ylidene)methyl) pyridin-2-yl)-2,4,6-trifluorobenzamide

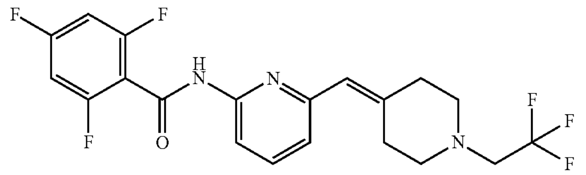 [SMILES: O=C(Nc1cccc(C=C2CCN(CC(F)(F)F)CC2)n1)c1c(F)cc(F)cc1F]

Step 1) Synthesis of 2-bromo-6-((1-(2,2,2-trifluoroethyl)piperidin-4-ylidene)methyl)pyridine Under 25° C., 2-bromo-6-(piperidin-4-ylidenemethyl) pyridine (500 mg, 2.0 mmol), N,N-diisopropylethylamine (1.0 mL, 6.1 mmol), 2,2,2-trifluoroethyltrifluoromethanesulfonate (0.7 mL, 3.9 mmol) and dichloromethane (10 mL) were added into a 100 mL single-neck round bottom flask, and the mixture was stirred for 16 hours. After the mixture was stopped stirring, water (30 mL) was added, and the resulting mixture was extracted with dichloromethane (30 mL×2). The combined organic layers were dried over anhydrous sodium sulfate (2 g) and filtered. The filtrate was concentrated using a rotary evaporator under reduced pressure. The residue was purified by column chromatography (dichloromethane/methanol (v/v)=100/1) to get the title compound as light yellow oil (0.61 g, 92.1%).

MS (ESI, pos. ion) m/z: 335.0 $[M+H]^+$;

$^1H$ NMR (400 MHz, $CDCl_3$) δ (ppm) 7.46 (t, J=7.6 Hz, 1H), 7.26 (d, J=7.6 Hz, 1H), 7.07 (d, J=7.6 Hz, 1H), 6.23 (s, 1H), 3.01 (q, J=9.6 Hz, 2H), 2.90 (t, J=5.6 Hz, 2H), 2.79 (t, J=5.6 Hz, 2H), 2.72 (t, J=5.6 Hz, 2H), 2.41 (t, J=5.6 Hz, 2H).

Step 2) Synthesis of N-(6-((1-(2,2,2-trifluoroethyl)piperidin-4-ylidene)methyl)pyridin-2-yl)-2,4,6-trifluorobenzamide The title compound of this step was prepared by referring to the method described in step 3 of example 1, i.e., 2-bromo-6-((1-(2,2,2-trifluoroethyl)piperidin-4-ylidene)methyl) pyridine (0.6 g, 1.8 mmol), 2,4,6-trifluoro-benzamide (200 mg, 1.1 mmol), potassium carbonate (1.1 g, 7.98 mmol), cuprous iodide (220 mg, 1.2 mmol), (1R,2R)—$N^1$, $N^2$-dimethylcyclohexane-1,2-diamine (0.2 mL, 1.17 mmol), water (1.0 mL) were reacted in toluene (10 mL) to prepare it. The crude product was purified by silica gel column chromatography (dichloromethane/methano (v/v)=50/1) to get the title compound as a light yellow solid (277 mg, 56.5%).

MS (ESI, pos. ion) m/z: 430.3 $[M+H]^+$;

$^1H$ NMR (400 MHz, DMSO-$d_6$) δ (ppm) 7.95 (d, J=8.0 Hz, 1H), 7.79 (t, J=8.0 Hz, 1H), 7.34 (t, J=8.8 Hz, 2H), 7.04 (d, J=7.6 Hz, 1H), 6.22 (s, 1H), 3.20 (q, J=10.4 Hz, 2H), 2.95 (brs, 2H), 2.74 (t, J=5.2 Hz, 2H), 2.66 (t, J=4.8 Hz, 2H), 2.32 (brs, 2H).

Example 19: Synthesis of 2,4,6-trifluoro-N-(6-(fluoro(1-ethylpiperidin-4-ylidene)methyl) pyridin-2-yl)benzamide

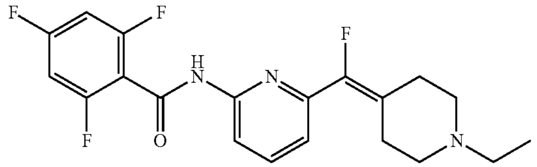 [SMILES: CCN1CCC(=C(F)c2cccc(NC(=O)c3c(F)cc(F)cc3F)n2)CC1]

Step 1) Synthesis of 2-bromo-6-(fluoro(piperidin-4-ylidene)methyl)pyridine

The title compound of this step was prepared by referring to the method described in step 4 of example 1, i.e., tert-butyl 4-((6-bromopyridin-2-yl)fluoromethylene)piperidine-1-carboxylate (1.6 g, 4.3 mmol) and methanesulfonic acid (0.84 mL, 13.0 mmol) were reacted in dichloromethane (15 mL) to prepare it. The crude product was purified by silica gel column chromatography (dichloromethane/methanol (v/v)=20/1) to give the title compound as a yellow solid (1.15 g, 95.8%).

MS (ESI, pos. ion) m/z: 271.1 $[M+H]^+$;

$^1$H NMR (400 MHz, $CDCl_3$) δ (ppm) 7.59 (t, J=7.8 Hz, 1H), 7.46 (d, J=7.8 Hz, 1H), 7.38 (d, J=7.9 Hz, 1H), 3.01-2.90 (m, 6H), 2.53 (dd, J=7.6, 3.4 Hz, 2H).

Step 2) Synthesis of 2-bromo-6-((1-ethylpiperidin-4-ylidene)fluoromethyl)pyridine Under 25° C., 2-bromo-6-(fluoro(piperidin-4-ylidene) methyl)pyridine (0.38 g, 1.4 mmol), N,N-diisopropylethylamine (0.69 mL, 4.2 mmol) and acetonitrile (5 mL) were added into a 100 mL single-neck round bottom flask, and then iodoethane (0.44 g, 2.8 mmol) was added. The mixture was stirred for 5 hours. After the mixture was stopped stirring, water (20 mL) was added, and the resulting mixture was extracted with dichloromethane (30 mL×2). The combined organic layers were dried over anhydrous sodium sulfate (2 g) and filtered. The filtrate was concentrated using a rotary evaporator under reduced pressure. The residue was purified by column chromatography (dichloromethane/methanol (v/v)=20/1) to get the title compound as a light yellow solid (0.4 g, 95.4%).

MS (ESI, pos. ion) m/z: 299.0 $[M+H]^+$;

$^1$H NMR (600 MHz, $CDCl_3$) δ (ppm) 7.60 (t, J=7.8 Hz, 1H), 7.47 (d, J=7.8 Hz, 1H), 7.40 (d, J=7.9 Hz, 1H), 3.21 (brs, 2H), 2.76 (brs, 6H), 2.67-2.62 (m, 2H), 1.26 (t, J=7.2 Hz, 3H).

Step 3) Synthesis of 2,4,6-trifluoro-N-(6-(fluoro(1-ethylpiperidin-4-ylidene)methyl)pyridin-2-yl) benzamide The title compound of this step was prepared by referring to the method described in step 3 of example 1, i.e., 2-bromo-6-((1-ethylpiperidin-4-ylidene)fluoromethyl)pyridine (0.38 g, 1.27 mmol), 2,4,6-trifluoro-benzamide (330 mg, 1.9 mmol), potassium carbonate (0.53 g, 3.8 mmol), cuprous iodide (240 mg, 1.3 mmol), (1R,2R)—$N^1$,$N^2$-dimethylcyclohexane-1,2-diamine (0.21 mL, 1.3 mmol), water (1.0 mL) were reacted in toluene (10 mL) to prepare it. The crude product was purified by silica gel column chromatography (dichloromethane/methano (v/v)=20/1) to get the title compound as a light yellow solid (0.2 g, 40%).

MS (ESI, pos. ion) m/z: 394.2 $[M+H]^+$;

$^1$H NMR (400 MHz, $CDCl_3$) δ (ppm) 8.79 (s, 1H), 8.30 (d, J=8.2 Hz, 1H), 7.83 (t, J=8.0 Hz, 1H), 7.28 (d, J=6.8 Hz, 1H), 6.73 (t, J=8.4 Hz, 2H), 2.84 (t, J=4.9 Hz, 2H), 2.59 (br, 2H), 2.56 (br, 2H), 2.44 (br, 4H), 1.11 (t, J=7.1 Hz, 3H).

Example 20: Synthesis of 2,4,6-trifluoro-N-(6-(fluoro(1-cyclopropylpiperidin-4-ylidene) methyl) pyridin-2-yl)benzamide

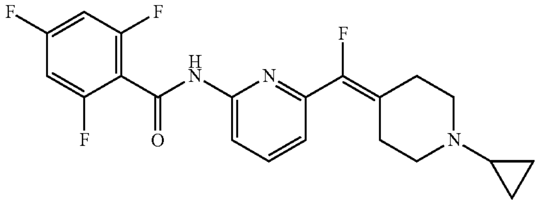 [SMILES: O=C(Nc1cccc(C(F)=C2CCN(C3CC3)CC2)n1)c1c(F)cc(F)cc1F]

Step 1) Synthesis of 2-bromo-6-((1-cyclopropylpiperidin-4-ylidene)fluoromethyl)pyridine The title compound of this step was prepared by referring to the method described in step 5 of example 1, i.e., 2-bromo-6-(fluoro(piperidin-4-ylidene)methyl)pyridine (1.1 g, 4.06 mmol), sodium cyanoborohydride (1.04 g, 16.2 mmol), 1-ethoxy-1-trimethylsiloxycyclopropane (2.44 mL, 12.2 mmol) and acetic acid (0.7 mL) were reacted in methanol (15 mL) to prepare it. The crude product was purified by silica gel column chromatography (dichloromethane/methanol (v/v)=100/1) to give the title compound as a white solid (1.2 g, 95.0%).

MS (ESI, pos. ion) m/z: 311.1 $[M+H]^+$;

$^1$H NMR (400 MHz, $CDCl_3$) δ (ppm) 7.57 (t, J=7.8 Hz, 1H), 7.45 (d, J=7.7 Hz, 1H), 7.37 (d, J=7.9 Hz, 1H), 2.96 (t, J=5.2 Hz, 2H), 2.74-2.69 (m, 4H), 2.57-2.54 (m, 2H), 1.65-1.59 (m, 1H), 0.48 (d, J=6.6 Hz, 4H).

Step 2) Synthesis of 2,4,6-trifluoro-N-(6-(fluoro(1-cyclopropylpiperidin-4-ylidene)methyl) pyridin-2-yl)benzamide The title compound of this step was prepared by referring to the method described in step 3 of example 1, i.e., 2-bromo-6-((1-cyclopropylpiperidin-4-ylidene)fluoromethyl)pyridine (1.2 g, 3.9 mmol), 2,4,6-trifluoro-benzamide (1.0 g, 5.7 mmol), potassium carbonate (1.6 g, 11.0 mmol), cuprous iodide (0.73 g, 3.8 mmol), (1R,2R)—$N^1$,$N^2$-dimethylcyclohexane-1,2-diamine (0.63 mL, 3.9 mmol), water (1.0 mL) were reacted in toluene (10 mL) to prepare it. The crude product was purified by silica gel column chromatography (petroleum ether/ethyl acetate (v/v)=5/1) to get the title compound as a white solid (0.99 g, 63.0%).

MS (ESI, pos. ion) m/z: 406.2 $[M+H]^+$;

$^1$H NMR (400 MHz, $CDCl_3$) δ (ppm) 8.50 (s, 1H), 8.29 (d, J=8.2 Hz, 1H), 7.83 (t, J=8.0 Hz, 1H), 7.30 (d, J=8.4 Hz, 1H), 6.78 (t, J=8.3 Hz, 2H), 2.80 (t, J=5.2 Hz, 2H), 2.72 (t, J=5.6 Hz, 2H), 2.64 (t, J=5.3 Hz, 2H), 2.55 (t, J=4.7 Hz, 2H), 1.61-1.58 (m, 1H), 0.49-0.42 (m, 4H).

Example 21: Synthesis of N-(6-((1-(2,2-difluoroethyl)piperidin-4-ylidene)fluoromethyl) pyridin-2-yl)-2,4,6-trifluorobenzamide

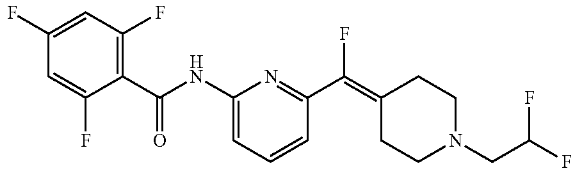 [SMILES: O=C(Nc1cccc(C(F)=C2CCN(CC(F)F)CC2)n1)c1c(F)cc(F)cc1F]

Step 1) Synthesis of 2-bromo-6-((1-(2,2-difluoroethyl)piperidin-4-ylidene)fluoromethyl)pyridine 2-Bromo-6-(fluoro(piperidin-4-ylidene)methyl)pyridine (1.0 g, 3.69 mmol), 2,2-difluoroethyl 4-methylbenzenesulfonate (1.31 g, 5.55 mmol), sodium iodide (550 mg, 3.7 mmol), potassium carbonate (770 mg, 5.5 mmol) and acetonitrile (15 mL) were added into a 100 mL single-neck round bottom flask, and the mixture was stirred at 90° C. in an oil bath for 12 hours. After the mixture was stopped stirring, water (40 mL) was added, and the resulting mixture was extracted with dichloromethane (30 mL×2). The combined organic layers were dried over anhydrous sodium sulfate (2 g) and filtered. The filtrate was concentrated using a rotary evaporator under reduced pressure. The residue was purified by column chromatography (petroleum ether/ethyl acetate (v/v)=40/1) to get the title compound as yellow oil (1.1 g, 89%).

MS (ESI, pos. ion) m/z: 335.0 $[M+H]^+$;

$^1$H NMR (400 MHz, $CDCl_3$) δ (ppm) 7.59 (t, J=7.8 Hz, 1H), 7.40 (t, J=6.9 Hz, 2H), 4.19 (td, J=12.7, 4.1 Hz, 1H), 3.03 (t, J=5.2 Hz, 2H), 2.79 (td, J=15.0, 4.3 Hz, 2H), 2.72-2.67 (m, 4H), 2.63-2.57 (m, 2H).

Step 2) Synthesis of N-(6-((1-(2,2-difluoroethyl) piperidin-4-ylidene)fluoromethyl)pyridin-2-yl)-2,4,6-trifluorobenzamide The title compound of this step was prepared by referring to the method described in step 3 of example 1, i.e., 2-bromo-6-((1-(2,2-difluoroethyl)piperidin-4-ylidene)fluoromethyl) pyridine (1.05 g, 3.13 mmol), 2,4,6-trifluorobenzamide (0.83 g, 4.7 mmol), potassium carbonate (1.31 g, 9.38 mmol), cuprous iodide (0.6 g, 3.2 mmol), (1R,2R)—$N^1$,$N^2$-dimethylcyclohexane-1,2-diamine (0.51 mL, 3.1 mmol), water (1.0 mL) were reacted in toluene (10 mL) to prepare it. The crude product was purified by silica gel column chromatography (petroleum ether/ethyl acetate (v/v) =5/1) to get the title compound as a white solid (0.92 g, 68%).

MS (ESI, pos. ion) m/z: 430.1 $[M+H]^+$;

$^1$H NMR (400 MHz, $CDCl_3$) δ (ppm) 8.39 (s, 1H), 8.29 (d, J=8.2 Hz, 1H), 7.84 (t, J=8.0 Hz, 1H), 7.31 (d, J=7.8 Hz, 1H), 6.80 (t, J=8.2 Hz, 2H), 5.92 (tt, J=55.9, 4.2 Hz, 1H), 2.86 (t, J=5.1 Hz, 2H), 2.77 (td, J=15.0, 4.3 Hz, 2H), 2.72-2.67 (m, 2H), 2.64-2.59 (m, 4H).

Example 22: Synthesis of N-(6-((1-(2,2,2-trifluoroethyl)piperidin-4-ylidene)fluoromethyl) pyridin-2-yl)-2,4,6-trifluorobenzamide

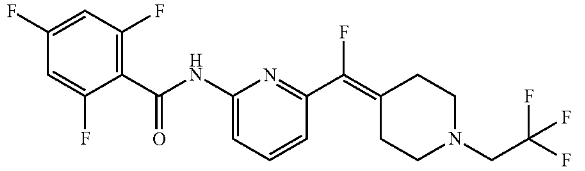 [SMILES: O=C(Nc1cccc(C(F)=C2CCN(CC(F)(F)F)CC2)n1)c1c(F)cc(F)cc1F]

Step 1) Synthesis of 2-bromo-6-(fluoro(1-(2,2,2-trifluoroethyl)piperidin-4-ylidene)methyl) pyridine Under 25° C., 2-bromo-6-(fluoro(piperidin-4-ylidene) methyl)pyridine (250 mg, 0.92 mmol), N,N-diisopropylethylamine (1.22 mL, 7.36 mmol), 2,2,2-trifluoroethyltrifluoromethanesulfonate (0.8 mL, 4.4 mmol) and dichloromethane (5 mL) were added into a 100 mL single-neck round bottom flask, and the mixture was stirred for 16 hours. After the mixture was stopped stirring, water (30 mL) was added, and the resulting mixture was extracted with dichloromethane (30 mL×2). The combined organic layers were dried over anhydrous sodium sulfate (2 g) and filtered. The filtrate was concentrated using a rotary evaporator under reduced pressure. The residue was purified by column chromatography (petroleum ether/ethyl acetate (v/v)=50/1) to get the title compound as colorless oil (0.27 g, 82.9%).

MS (ESI, pos. ion) m/z: 353.0 $[M+H]^+$;

$^1$H NMR (400 MHz, $CDCl_3$) δ (ppm) 7.59 (t, J=7.8 Hz, 1H), 7.46 (d, J=7.7 Hz, 1H), 7.39 (d, J=7.9 Hz, 1H), 3.08-2.96 (m, 4H), 2.82-2.77 (m, 4H), 2.65-2.54 (m, 2H).

Step 2) Synthesis of N-(6-((1-(2,2,2-trifluoroethyl) piperidin-4-ylidene)fluoromethyl)pyridin-2-yl)-2,4,6-trifluorobenzamide The title compound of this step was prepared by referring to the method described in step 3 of example 1, i.e., 2-bromo-6-(fluoro(1-(2,2,2-trifluoroethyl)piperidin-4-ylidene)methyl) pyridine (0.5 g, 1.42 mmol), 2,4,6-trifluorobenzamide (0.49 g, 2.8 mmol), potassium carbonate (0.6 g, 4.3 mmol), cuprous iodide (0.4 g, 2.1 mmol), (1R,2R)—$N^1$,$N^2$-dimethylcyclohexane-1,2-diamine (0.23 mL, 1.4 mmol), water (1.0 mL) were reacted in toluene (10 mL) to prepare it. The crude product was purified by silica gel column chromatography (petroleum ether/ethyl acetate (v/v)=5/1) to get the title compound as a white solid (0.35 g, 55.3%).

MS (ESI, pos. ion) m/z: 448.2 $[M+H]^+$;

$^1$H NMR (400 MHz, $CDCl_3$) δ (ppm) 8.51 (s, 1H), 8.30 (d, J=8.2 Hz, 1H), 7.84 (t, J=8.0 Hz, 1H), 7.30 (d, J=7.9 Hz, 1H), 6.78 (t, J=8.2 Hz, 2H), 3.01 (q, J=9.6 Hz, 2H), 2.86 (t, J=5.0 Hz, 2H), 2.79 (t, J=5.6 Hz, 2H), 2.70 (t, J=5.2 Hz, 2H), 2.64-2.54 (m, 2H).

Example 23: Synthesis of 2,4,6-trifluoro-N-(6-(fluoro(1-methylpiperidin-4-ylidene)methyl) pyridin-2-yl)benzenesulfonamide

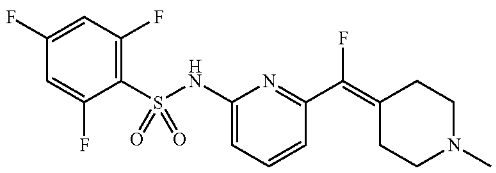 [SMILES: CN1CCC(=C(F)c2cccc(NS(=O)(=O)c3c(F)cc(F)cc3F)n2)CC1]

Step 1) Synthesis of tert-butyl 4-(fluoro(6-(2,4,6-trifluorobenzenesulfonamide)pyridin-2-yl) methylene)piperidine-1-carboxylate The title compound of this step was prepared by referring to the method described in step 3 of example 1, i.e., tert-butyl 4-((6-bromopyridin-2-yl)fluoromethylene)piperidine-1-carboxylate (0.2 g, 0.54 mmol), 2,4,6-trifluorobenzenesulfonamide (170 mg, 0.81 mmol), potassium carbonate (0.23 g, 1.6 mmol), cuprous iodide (100 mg, 0.53 mmol), (1R,2R)—$N^1$,$N^2$-dimethylcyclohexane-1,2-diamine (0.09 mL, 0.6 mmol), water (0.5 mL) were reacted in toluene (5 mL) to prepare it. The crude product was purified by silica gel column chromatography (dichloromethane/ethyl acetate (v/v)=10/1) to get the title compound as yellow oil (0.24 g, 88.8%).

MS (ESI, pos. ion) m/z: 446.2 $[M+H-56]^+$;

$^1$H NMR (400 MHz, $CDCl_3$) δ (ppm) 7.72 (t, J=8.0 Hz, 1H), 7.24 (t, J=9.2 Hz, 2H), 6.78 (t, J=8.6 Hz, 2H), 3.55-3.51 (m, 2H), 3.49-3.45 (m, 2H), 2.80 (t, J=5.1 Hz, 2H), 2.52 (brs, 2H), 1.51 (s, 9H).

Step 2) Synthesis of 2,4,6-trifluoro-N-(6-(fluoro (piperidine-4-ylidene)methyl)pyridin-2-yl) benzenesulfonamide The title compound of this step was prepared by referring to the method described in step 4 of example 1, i.e., tert-butyl 4-(fluoro(6-(2,4,6-trifluorobenzenesulfonamide) pyridin-2-yl) methylene)piperidine-1-carboxylate (0.23 g, 0.46 mmol) and methanesulfonic acid (0.13 g, 1.4 mmol) were reacted in dichloromethane (5 mL) to prepare it. The crude product was purified by silica gel column chromatography (dichloromethane/methanol (v/v)=20/1) to give the title compound as a light yellow solid (0.11 g, 59.7%).

MS (ESI, pos. ion) m/z: 402.1 $[M+H]^+$;

$^1$H NMR (400 MHz, $CDCl_3$) δ (ppm) 7.54-7.47 (m, 1H), 7.22 (s, 1H), 7.14 (d, J=8.4 Hz, 1H), 6.85 (d, J=7.7 Hz, 1H), 6.70 (t, J=8.8 Hz, 1H), 2.82-2.75 (m, 4H), 2.51 (br, 4H).

Step 3) Synthesis of 2,4,6-trifluoro-N-(6-(fluoro(1-methylpiperidin-4-ylidene)methyl) pyridin-2-yl) benzenesulfonamide The title compound of this step was prepared by referring to the method described in step 5 of example 1, i.e., 2,4,6-trifluoro-N-(6-(fluoro(piperidin-4-ylidene)methyl) pyridin-2-yl) benzenesulfonamide (0.09 g, 0.22 mmol), sodium cyanoborohydride (50 mg, 0.8 mmol) and formaldehyde (40%, 0.17 mL, 2.3 mmol) were reacted in methanol (4 mL) to prepare it. The crude product was purified by silica gel column chromatography (dichloromethane/methanol (v/v)=50/1) to give the title compound as a light yellow solid (0.085 g, 91.2%).

MS (ESI, pos. ion) m/z: 416.1 $[M+H]^+$;

$^1$H NMR (400 MHz, $CDCl_3$) δ (ppm) 7.64 (t, J=8.0 Hz, 1H), 7.21 (d, J=8.3 Hz, 1H), 7.10 (d, J=7.5 Hz, 1H), 6.76 (t, J=8.6 Hz, 2H), 3.07 (t, J=4.5 Hz, 2H), 2.97 (t, J=5.4 Hz, 2H), 2.92 (t, J=4.9 Hz, 2H), 2.78 (t, J=5.0 Hz, 2H), 2.62 (s, 3H).

Biological Assay

Example A: Evaluation of the Activating Effect of the Compound of the Invention on Human 5-$HT_{1F}$ Receptor Transfected by CHO-K1 Cells Experimental purposes: To evaluate the activating effect of the compound on CHO-K1 cells transfected human 5-$HT_{1F}$ receptor by using HitHunter cAMP detection kit.

Experimental brief process: CHO-K1 cells were cultured in a 384 microporous plate. The volume of cell culture medium (Assay Complete™ Cell Plating Reagent, DIscoverX) was 20 μL and the cell density was 10,000/well. The cells were cultured overnight at 37° C. and 5% $CO_2$. Then the culture medium was removed, and 15 μL of cAMP Assay Buffer (DIscoverX) was added into each well, and then 5 μL of test sample containing 4× sample (test compound or 5-HT) and 4× forskolin (final concentration of forskolin is 15 μM) was added. The microporous plate was placed at 37° C. for 30 minutes. Then 5 μL of cAMP Antibody Reagent (DiscoverX) and 20 μL of cAMP Working Detection Solution (DiscoverX) were added and incubated in the dark for 1 hour, and then 20 μL of cAMP Solution A was added and incubated in the dark for 3 hours. The microporous plate was placed in the Perkin Elmer Envision™ to read the intensity of the optical signal. The activation rate was calculated by the intensity of the optical signal obtained from testing the compounds with different concentrations ((1−(Y/Z)) *100%=the activation rate, wherein, Y represents the intensity of the optical signal adding test sample, and Z represents the intensity of the optical signal adding only forskolin). The dose-effect curve of the compounds was calculated by Prism software, and the concentration of the agonist with half maximum response was calculated and expressed by $EC_{50}$ value. The results were shown in Table A. 5-HT was used as a positive control drug to ensure the normal experimental system in this experiment.

TABLE A

Test results of the activating effect of the compound of the invention on human 5-$HT_{1F}$ receptor transfected by CHO-$K_1$ cells

| Example No. | $EC_{50}$ (nM) |
|---|---|
| Example 3 | 5.9 |
| Example 5 | 1.9 |
| Example 10 | 3.0 |
| Example 12 | 1.5 |
| Example 19 | 6.8 |

The experimental results show that the compound of the invention has strong activation activity on 5-$HT_{1F}$ receptor.

Example B: Pharmacokinetic Evaluation after Administering a Certain Amount of the Compound of the Invention by Intravenous or Gavage to Rats and Dogs The inventors had evaluated the pharmacokinetics of the compounds of the invention in rats and dogs. Wherein animal information was detailed in Table 1.

TABLE 1

| The animal subject information of the invention | | | | | |
|---|---|---|---|---|---|
| Germline | Grade | Sex | Weight | Age | Source |
| SD rats | SPF | male | 180-350 g | 6-11 weeks | Hunan SJA Laboratory Animal Co., Ltd. |
| Beagle dogs | Conventional | male | 8-12 kg | 6-12 months | Beijing Marshall Biotechnology Co., Ltd. |

Test Method:

The compound was administered to the animal subjects in the form of 5% DMSO+60% PEG400+35% Saline solution or 10% DMSO+10% Kolliphor HS15+30% PEG400+50% Saline solution. The animals were fasted for 12 hours before administration, but drinking water freely. For the group of intravenous administration, the administration dose is 0.5 mg/kg or 1 mg/kg, and vein blood samples (0.15 mL) were collected at the time points of 0.083, 0.25, 0.5, 1.0, 2.0, 4.0, 6.0, 8.0 and 24 h (dogs) or 0.083, 0.25, 0.5, 1.0, 2.0, 5.0, 7.0 and 24 h (rats) after drug administration. EDTA-$K_2$ as anticoagulant was pre-added into the blood vessel. The plasma solutions were collected by centrifuging each blood sample at 12,000 rpm for 2 minutes and kept at −20° C. or −70° C. For the group of gavage administration, the administration dose is 2.5 mg/kg or 5 mg/kg, and vein blood samples (0.15 mL) were collected at the time points of 0.25, 0.5, 1.0, 2.0, 4.0, 6.0, 8.0 and 24 h (dogs) or 0.25, 0.5, 1.0, 2.0, 5.0, 7.0 and 24 h (rats) after drug administration. EDTA-$K_2$ as anticoagulant was pre-added into the blood vessel. The plasma solutions were collected by centrifuging each blood sample at 12,000 rpm for 2 minutes and kept at −20° C. or −70° C.

After processing the above plasma sample (the frozen plasma was melted at room temperature and then whirled for 15 seconds. 10 to 20 μL of the plasma was taken out, and whirled with 120 to 150 μL of an acetonitrile solution containing an internal standard for 5 minutes. The mixture was centrifuged for 5 minutes at 4,000 rpm. 100 μL of the supernatant was taken out and mixed with 120 to 150 μL of methanol-water (v/v=1/1)), the concentration of compounds in plasma was analyzed by LC-MS/MS. The analysis results show that the compound of the invention has good pharmacokinetic properties in rats, dogs. The compound of the invention has better drug properties and better clinical application prospects. Wherein the pharmacokinetic parameters of examples 12 and 19 in rats were detailed in Table B1; the pharmacokinetic parameters of examples 12 and 19 in dogs were detailed in Table B2.

TABLE B1

| Pharmacokinetic parameters of the compounds of the invention in rats | | | | | | | | | | | |
|---|---|---|---|---|---|---|---|---|---|---|---|
| Groups | Test substance | Dose (mg/kg) | $T_{max}$ (h) | $C_{max}$ (ng/mL) | $AUC_{last}$ (h * ng/mL) | $AUC_{INF}$ (h * ng/mL) | $MRT_{INF}$ (h) | $T_{1/2}$ (h) | Cl (mL/min/kg) | $V_{ss}$ (L/kg) | F (%) |
| i.v group | Example 12 | 1 | 0.083 | 80.5 | 111 | 114 | 1.66 | 1.38 | 146 | 14.6 | ND |
| | Example 19 | 1 | 0.5 | 67.7 | 240 | 259 | 2.95 | 2.1 | 64.4 | 11.4 | ND |
| i.g group | Example 12 | 5 | 2 | 71.8 | 296 | 354 | 4.05 | 2.31 | ND | ND | 62 |
| | Example 19 | 5 | 3.67 | 169 | 1260 | 1320 | 5.01 | 3.06 | ND | ND | 105 |

ND means no test data.

The results of Table B1 show that the compounds of the invention have good pharmacokinetic properties in rats.

TABLE B2

| Pharmacokinetic parameters of the compounds of the invention in dogs | | | | | | | | | | | |
|---|---|---|---|---|---|---|---|---|---|---|---|
| Groups | Test substance | Dose (mg/kg) | $T_{max}$ (h) | $C_{max}$ (ng/mL) | $AUC_{last}$ (h * ng/mL) | $AUC_{INF}$ (h * ng/mL) | $MRT_{INF}$ (h) | $T_{1/2}$ (h) | Cl (mL/min/kg) | $V_{ss}$ (L/kg) | F (%) |
| i.v group | Example 12 | 1 | 0.25 | 170 | 652 | 660 | 4.11 | 3.52 | 25.2 | 6.22 | ND |
| | Example 19 | 0.5 | 0.083 | 442 | 632 | 634 | 1.39 | 1.06 | 13.1 | 1.1 | ND |
| i.g group | Example 12 | 5 | 1.67 | 82.8 | 691 | 705 | 5.98 | 4.28 | ND | ND | 21.4 |
| | Example 19 | 2.5 | 1 | 126 | 356 | 392 | 3.26 | 1.96 | ND | ND | 12.4 |

ND means no test data.

The results of Table B2 show that the compounds of the invention have good pharmacokinetic properties in dogs.

Reference throughout this specification to "an embodiment", "some embodiments", "one embodiment", "another example", "an example", "a specific example", or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example", or "in some examples" in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a tautomer, an N-oxide, a hydrate, a solvate, a pharmaceutically acceptable salt or a prodrug thereof, (I)

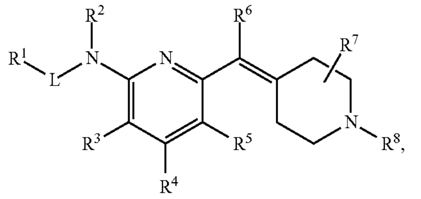

wherein

L is —C(═O)—, —C(═S)— or —S(═O)$_2$—;

$R^1$ is $C_1$-$C_6$ alkyl, $C_3$-$C_8$ cycloalkyl, 3-8 membered heterocyclyl, $C_6$-$C_{10}$ aryl or 5-10 membered heteroaryl, wherein $R^1$ is optionally substituted with 1, 2, 3, 4 or 5 substituents independently selected from $R^{1a}$, $R^{1b}$, $R^{1c}$, $R^{1d}$ and $R^{1e}$;

each $R^{1a}$, $R^{1b}$, $R^{1c}$, $R^{1d}$ and $R^{1e}$ is independently H, F, Cl, Br, I, —CN, —$NO_2$, —$NH_2$, —OH, —SH, —COOH, —C(═O)$NH_2$, —C(═O)$NHCH_3$, —C(═O)N($CH_3$) 2, —C(═O)—($C_1$-$C_6$ alkyl), —C(═O)—($C_1$-$C_6$ alkoxy), $C_1$-$C_6$ alkyl, $C_2$-$C_6$ alkenyl, $C_2$-$C_6$ alkynyl, $C_1$-$C_6$ haloalkyl, $C_1$ —$C_6$ alkoxy, $C_1$-$C_6$ haloalkoxy, $C_1$-$C_6$ alkylthio, C1-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl or 5-10 membered heteroaryl;

$R^2$ is H, F, Cl, Br, I, —CN, —$NO_2$, —$NH_2$, —OH, —COOH, —C(═O)$NH_2$, $C_1$-$C_6$ alkyl, $C_1$-$C_6$ haloalkyl, $C_1$-$C_6$ alkoxy, $C_1$-$C_6$ haloalkoxy or hydroxy-substituted $C_1$-$C_6$ alkyl;

each of $R^3$, $R^4$ and $R^5$ is independently H, F, Cl, Br, I, —CN, —$NO_2$, —$NH_2$, —OH, —COOH, —C(═O) $NH_2$, $C_1$-$C_6$ alkyl, $C_1$-$C_6$ haloalkyl, $C_1$-$C_6$ alkoxy, $C_1$-$C_6$ haloalkoxy or hydroxy-substituted $C_1$-$C_6$ alkyl;

$R^6$ is H, F, Cl, Br or I;

$R^7$ is H, F, Cl, Br, I, —CN, —$NO_2$, —$NH_2$, —OH, —COOH, —C(═O)$NH_2$, $C_1$-$C_6$ alkyl, $C_1$-$C_6$ haloalkyl, $C_1$-$C_6$ alkoxy, $C_1$-$C_6$ haloalkoxy or hydroxy-substituted $C_1$-$C_6$ alkyl; and $R^8$ is H, F, Cl, Br, I, —CN, —$NO_2$, —$NH_2$, —OH, —SH, —COOH, —C(═O)$NH_2$, —C(═O)$NHCH_3$, —C(═O)N($CH_3$)$_2$, —C(═O)—($C_1$-$C_6$ alkyl), —C(═O)—($C_1$-$C_6$ alkoxy), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl or 5-10 membered heteroaryl.

2. The compound of claim 1, wherein $R^1$ is $C_1$-$C_4$ alkyl, $C_3$-$C_6$ cycloalkyl, 3-6 membered heterocyclyl, $C_6$-$C_{10}$ aryl or 5-10 membered heteroaryl, wherein $R^1$ is optionally substituted with 1, 2, 3, 4 or 5 substituents independently selected from $R^{1a}$, $R^{1b}$, $R^{1c}$, $R^{1d}$ and $R^{1e}$;

each $R^{1a}$, $R^{1b}$, $R^{1c}$, $R^{1d}$ and $R^{1e}$ is independently H, F, Cl, Br, I, —CN, —$NO_2$, —$NH_2$, —OH, —SH, —COOH, —C(═O)$NH_2$, —C(═O)$NHCH_3$, —C(═O)N($CH_3$)$_2$, —C(═O)—($C_1$-$C_4$ alkyl), —C(═O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl.

3. The compound of claim 1, wherein $R^1$ is phenyl, indenyl, naphthyl, pyrrolyl, pyrazolyl, imidazolyl, triazolyl, tetrazolyl, furyl, thienyl, thiazolyl, oxazolyl, pyridyl, pyrimidinyl, pyrazinyl, pyridazinyl, benzimidazolyl, indolyl or quinolyl, wherein $R^1$ is optionally substituted with 1, 2, 3, 4 or 5 substituents independently selected from $R^{1a}$, $R^{1b}$, $R^{1c}$, $R^{1d}$ and $R^{1e}$;

each $R^{1a}$, $R^{1b}$, $R^{1c}$, $R^{1d}$ and $R^{1e}$ is independently H, F, Cl, Br, I, —CN, —$NO_2$, —$NH_2$, —OH, —SH, —COOH, —C(═O)$NH_2$, —C(═O)$NHCH_3$, —C(═O)N($CH_3$)$_2$, —C(═O)—$CH_3$, —C(═O)—$OCH_3$, methyl, ethyl, n-propyl, i-propyl, allyl, propenyl, propargyl, propinyl, —$CHF_2$, -$CF_3$, —$CHFCH_2F$, —$CF_2CHF_2$, —$CH_2CF_3$, —$CH_2CF_2CHF_2$, methoxy, ethoxy, n-propoxy, i-propoxy, —$OCHF_2$, —$OCF_3$, —$OCHFCH_2F$, —$OCF_2CHF_2$, —$OCH_2CF_3$, —$OCH_2CF_2CHF_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl.

4. The compound of claim 1, wherein $R^2$ is H, F, Cl, Br, I, —CN, —NO2, —NH2, —OH, —COOH, —C(═O)$NH_2$, $C_1$-$C_4$ alkyl, $C_1$-$C_4$ haloalkyl, $C_1$-$C_4$ alkoxy, $C_1$-$C_4$ haloalkoxy or hydroxy-substituted $C_1$-$C_4$ alkyl;

each of $R^3$, $R^4$ and $R^5$ is independently H, F, Cl, Br, I, —CN, —$NO_2$, —$NH_2$, —OH, —COOH, —C(═O) $NH_2$, $C_1$-$C_4$ alkyl, $C_1$-$C_4$ haloalkyl, $C_1$-$C_4$ alkoxy, $C_1$-$C_4$ haloalkoxy or hydroxy-substituted $C_1$-$C_4$ alkyl;

$R^7$ is H, F, Cl, Br, I, —CN, —$NO_2$, —$NH_2$, —OH, —COOH, —C(═O)$NH_2$, $C_1$-$C_4$ alkyl, $C_1$-$C_4$ haloalkyl, $C_1$-$C_4$ alkoxy, $C_1$-$C_4$ haloalkoxy or hydroxy-substituted $C_1$-$C_4$ alkyl.

5. The compound of claim 1, wherein $R^2$ is H, F, Cl, Br, I, —CN, —$NO_2$, —$NH_2$, —OH, —COOH, —C(═O)$NH_2$, methyl, ethyl, n-propyl, i-propyl, $-CF_3$, $-CH_2CF_3$, methoxy, ethoxy, n-propoxy or i-propoxy;

each of $R^3$, $R^4$ and $R^5$ is independently H, F, Cl, Br, I, —CN, $-NO_2$, $-NH_2$, —OH, —COOH, —C(═O)$NH_2$, methyl, ethyl, n-propyl, i-propyl, $-CF_3$, $-CH_2CF_3$, methoxy, ethoxy, n-propoxy or i-propoxy;

$R^7$ is H, F, Cl, Br, I, —CN, $-NO_2$, $-NH_2$, —OH, —COOH, —C(═O)$NH_2$, methyl, ethyl, n-propyl, i-propyl, $-CF_3$, $-CH_2CF_3$, methoxy, ethoxy, n-propoxy or i-propoxy.

6. The compound of claim 1, wherein $R^8$ is H, F, Cl, Br, I, —CN, $-NO_2$, $-NH_2$, —OH, —SH, —COOH, —C(═O)$NH_2$, —C(═O)$NHCH_3$, —C(═O)$N(CH_3)_2$, —C(═O)—($C_1$-$C_4$ alkyl), —C(═O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl.

7. The compound of claim 1, wherein $R^8$ is H, F, Cl, Br, I, —CN, $-NO_2$, $-NH_2$, —OH, —SH, —COOH, —C(═O)$NH_2$, —C(═O)$NHCH_3$, —C(═O)$N(CH_3)_2$, —C(═O)—$CH_3$, —C(═O)—$OCH_3$, methyl, ethyl, n-propyl, i-propyl, allyl, propenyl, propargyl, propinyl, $-CHF_2$, $-CF_3$, $-CHFCH_2F$, $-CF_2CHF_2$, $-CH_2CHF_2$, $-CH_2CF_3$, $-CH_2CF_2CHF_2$, methoxy, ethoxy, n-propoxy, i-propoxy, $-OCHF_2$, $-OCF_3$, $-OCHFCH_2F$, $-OCF_2CHF_2$, $-OCH_2CF_3$, $-OCH_2CF_2CHF_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl.

8. The compound of claim 1 having Formula (II), or a stereoisomer, a tautomer, an N-oxide, a hydrate, a solvate, a pharmaceutically acceptable salt or a prodrug thereof, (II)

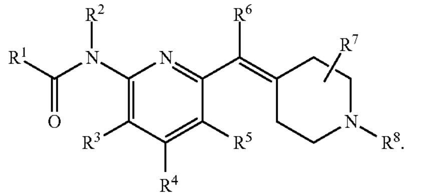

9. The compound of claim 1 having Formula (III), or a stereoisomer, a tautomer, an N-oxide, a hydrate, a solvate, a pharmaceutically acceptable salt or a prodrug thereof, (III)

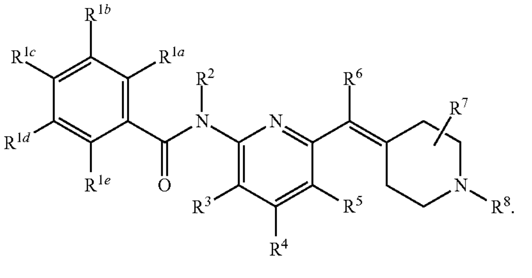

10. The compound of claim 1 having Formula (IVa), (IVb) or (IVc), or a stereoisomer, a tautomer, an N-oxide, a hydrate, a solvate, a pharmaceutically acceptable salt or a prodrug thereof, (IVa)

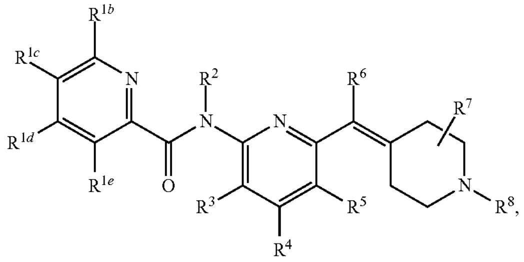

(IVb)

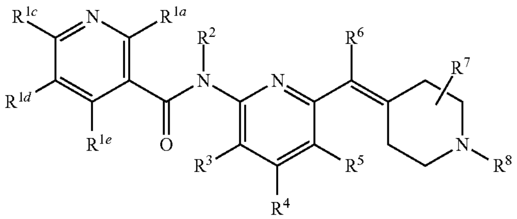

or (IVc)

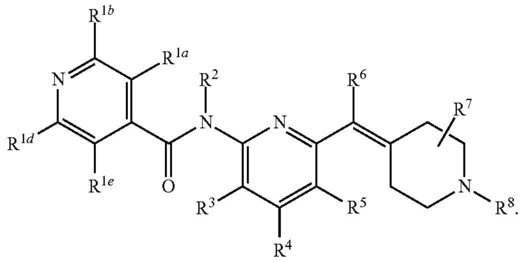

11. The compound of claim 1 having Formula (V), or a stereoisomer, a tautomer, an N-oxide, a hydrate, a solvate, a pharmaceutically acceptable salt or a prodrug thereof, (V)

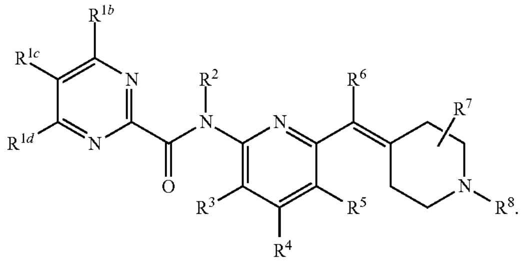

12. The compound according to claim 1 having one of the following structures or a stereoisomer, a tautomer, an N-oxide, a hydrate, a solvate, a pharmaceutically acceptable salt or a prodrug thereof:

-continued
(1)
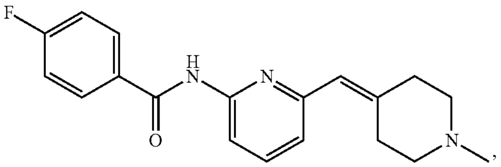
(2)
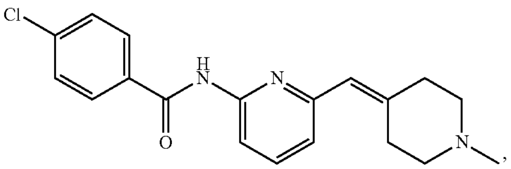
(3)
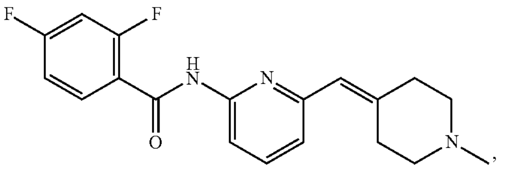
(4)
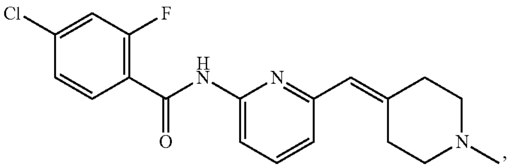
(5)
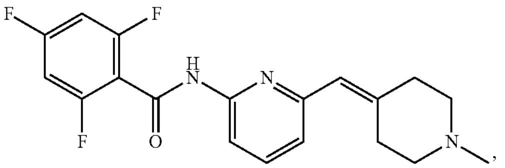
(6)
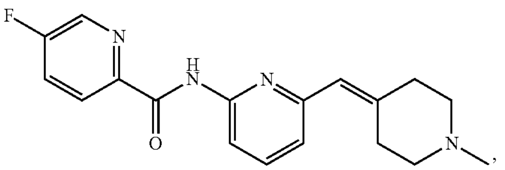
(7)
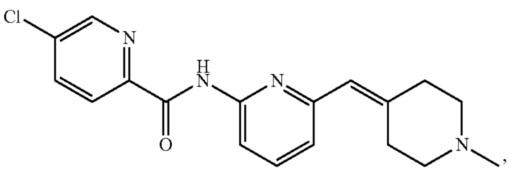
(8)
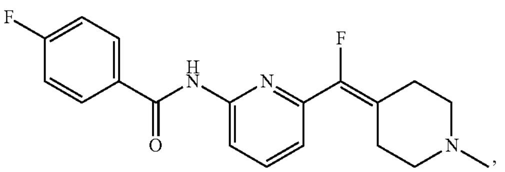
(9)
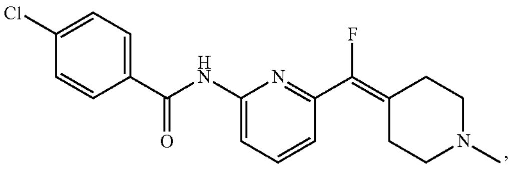
(10)
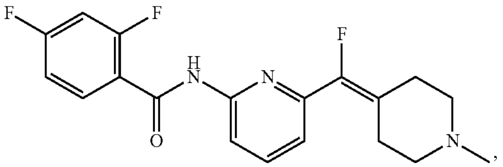
(11)
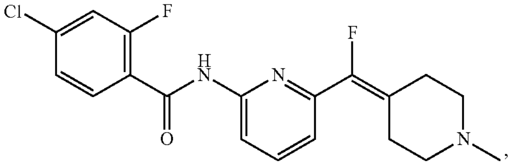
(12)
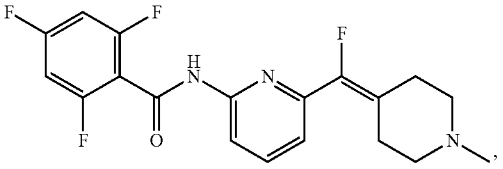
(13)
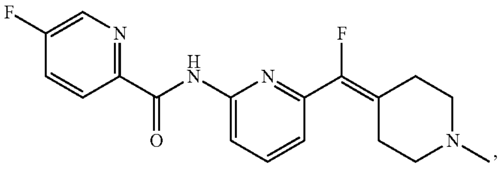
(14)
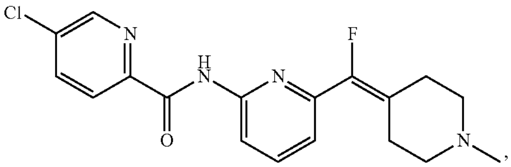
(15)
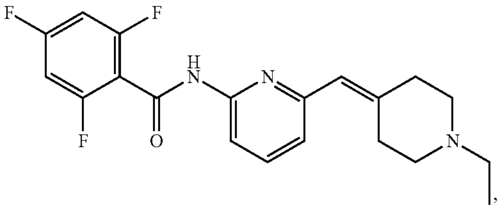
(16)
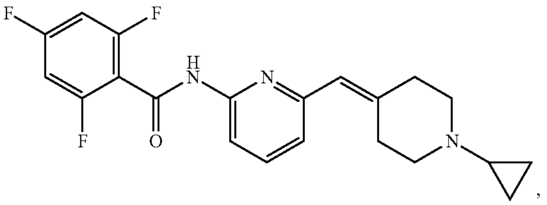

-continued (17)

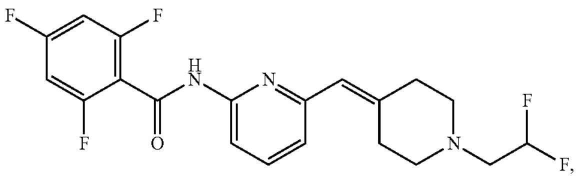

(18)

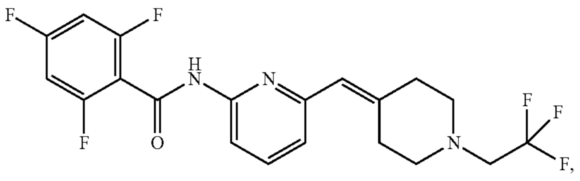

(19)

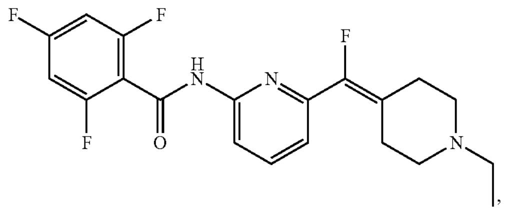

(20)

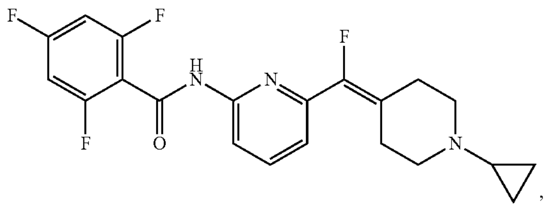

(21)

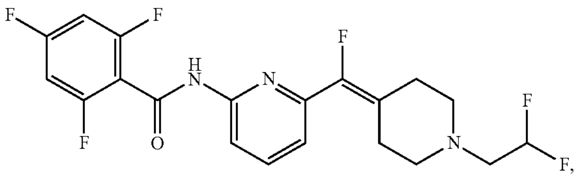

(22)

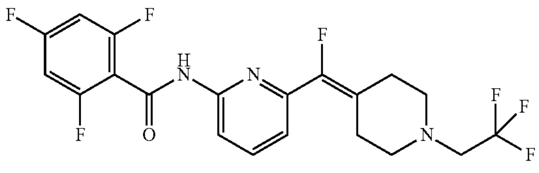

or (23)

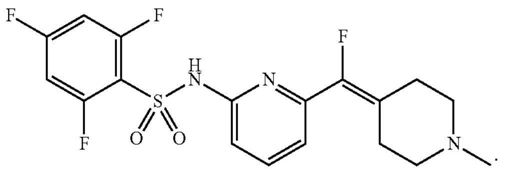

13. A pharmaceutical composition comprising the compound of claim 1; and wherein the pharmaceutical composition optionally further comprises a pharmaceutically acceptable excipient, carrier, or adjuvant or a combination thereof.

14. A method of treating or lessening a 5-$HT_{1F}$ receptor-related disease in a subject, comprising administering a therapeutically effective amount of the compound of claim 1 or a pharmaceutical composition comprising the compound, and wherein the pharmaceutical composition optionally further comprises a pharmaceutically acceptable excipient, carrier, or adjuvant or a combination thereof.

15. The method of claim 14, wherein the 5-$HT_{1F}$ receptor-related disease is migraine, general pain, trigeminal neuralgia, dental pain or temperomandibular joint dysfunction pain, autism, obsession, phobia, depression, social phobia, anxiety, general anxiety disorder, disorders of sleep, post-traumatic syndrome, chronic fatigue syndrome, premenstrual syndrome or late luteal phase syndrome, borderline personality disorder, disruptive behavior disorders, impulse control disorders, attention deficit hyperactivity disorder, alcoholism, tobacco abuse, mutism, trichotillomania, bulimia, anorexia nervosa, premature ejaculation, erectile dysfunction, memory loss or dementia.

16. A method of activating 5-$HT_{1F}$ receptor in a subject, comprising administering a therapeutically effective amount of the compound of claim 1 or a pharmaceutical composition comprising the compound, and wherein the pharmaceutical composition optionally further comprises a pharmaceutically acceptable excipient, carrier, or adjuvant or a combination thereof.

17. A method of treating or lessening a 5-$HT_{1F}$ receptor-related disease in a subject, comprising administering a therapeutically effective amount of the pharmaceutical composition of claim 13 to the subject.

18. The method of claim 17, wherein the 5-$HT_{1F}$ receptor-related disease is migraine, general pain, trigeminal neuralgia, dental pain or temperomandibular joint dysfunction pain, autism, obsession, phobia, depression, social phobia, anxiety, general anxiety disorder, disorders of sleep, post-traumatic syndrome, chronic fatigue syndrome, premenstrual syndrome or late luteal phase syndrome, borderline personality disorder, disruptive behavior disorders, impulse control disorders, attention deficit hyperactivity disorder, alcoholism, tobacco abuse, mutism, trichotillomania, bulimia, anorexia nervosa, premature ejaculation, erectile dysfunction, memory loss or dementia.

19. A method of activating 5-$HT_{1F}$ receptor in a subject, comprising administering a therapeutically effective amount of the pharmaceutical composition of claim 13 to the subject.

* * * * *